(12) United States Patent
Bäck

(10) Patent No.: US 8,764,927 B2
(45) Date of Patent: *Jul. 1, 2014

(54) METHOD AND APPARATUS FOR PROVIDING A DIAPER

(75) Inventor: Lucas Bäck, Billdal (SE)

(73) Assignee: SCA Hygiene Products AB, Gothenburg (SE)

(*) Notice: Subject to any disclaimer, the term of this patent is extended or adjusted under 35 U.S.C. 154(b) by 312 days.

This patent is subject to a terminal disclaimer.

(21) Appl. No.: 13/318,060

(22) PCT Filed: Apr. 30, 2009

(86) PCT No.: PCT/SE2009/050468
§ 371 (c)(1),
(2), (4) Date: Nov. 15, 2011

(87) PCT Pub. No.: WO2010/126415
PCT Pub. Date: Nov. 4, 2010

(65) Prior Publication Data
US 2012/0055613 A1    Mar. 8, 2012

(51) Int. Cl.
*A61F 13/15*    (2006.01)
(52) U.S. Cl.
CPC ..... *A61F 13/15601* (2013.01); *A61F 13/15609* (2013.01); *A61F 13/15804* (2013.01)
USPC .......... 156/177; 156/179; 156/181; 156/204; 156/267; 156/438; 156/440

(58) Field of Classification Search
None
See application file for complete search history.

(56) References Cited

U.S. PATENT DOCUMENTS

| 4,379,016 A | 4/1983 | Stemmler et al. |
| 4,578,133 A | 3/1986 | Oshefsky et al. |
| 4,675,068 A | 6/1987 | Lundmark |

(Continued)

FOREIGN PATENT DOCUMENTS

| CN | 1319384 A | 10/2001 |
| JP | 2006-519666 | 8/2006 |

(Continued)

OTHER PUBLICATIONS

Search Report issued Jun. 20, 2013 in Chinese patent application No. 200980160182.6 (and English translation thereof) (14 pages).

(Continued)

*Primary Examiner* — Barbara J Musser
(74) *Attorney, Agent, or Firm* — Drinker Biddle & Reath LLP

(57) ABSTRACT

A method for manufacturing elasticated webs including discontinous elastic threads, and methods for manufacturing articles from such elasticated webs. Apparatus for carrying out the methods. Further, elasticated webs and articles which can be manufactured using the methods.

24 Claims, 22 Drawing Sheets

(56) References Cited

U.S. PATENT DOCUMENTS

| | | | |
|---|---|---|---|
| 4,786,346 | A | 11/1988 | Ales et al. |
| 4,813,946 | A | 3/1989 | Sabee |
| 5,643,396 | A | 7/1997 | Rajala et al. |
| 5,660,657 | A | 8/1997 | Rajala et al. |
| 5,660,664 | A * | 8/1997 | Herrmann ............ 156/161 |
| 6,179,946 | B1 | 1/2001 | Ward et al. |
| 6,482,278 | B1 | 11/2002 | McCabe et al. |
| 6,521,320 | B2 | 2/2003 | McCabe et al. |
| 6,551,431 | B2 * | 4/2003 | Lee ............ 156/226 |
| 6,623,468 | B2 | 9/2003 | Shimoe |
| 2002/0193775 | A1 | 12/2002 | Shimoe |
| 2003/0077008 | A1 | 4/2003 | Plourde et al. |
| 2005/0000628 | A1 | 1/2005 | Norrby |
| 2006/0064069 | A1 | 3/2006 | Rajala et al. |
| 2006/0243373 | A1 | 11/2006 | Krueger et al. |

FOREIGN PATENT DOCUMENTS

| | | |
|---|---|---|
| JP | 2007-044295 | 2/2007 |
| WO | 97/00654 | 1/1997 |
| WO | 98/25767 | 6/1998 |
| WO | WO-2004/078083 | 9/2004 |
| WO | 2009/002235 | 12/2008 |

OTHER PUBLICATIONS

Office Action issued by the Russian Patent Office in Russian patent application No. 2011148587 dated Apr. 3, 2013 (and English translation thereof) (22 pages).

English translation of Japanese Office Action mailed May 21, 2013 in corresponding Japanese patent application No. 2012-508423 (3 pages).

* cited by examiner

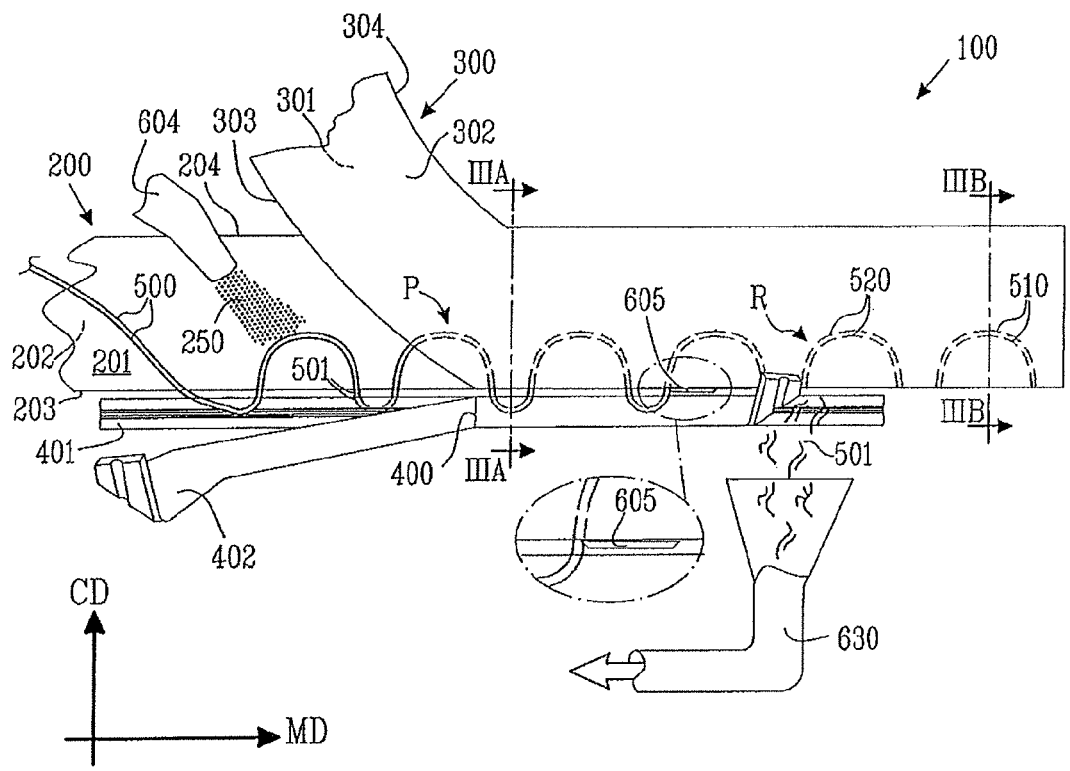
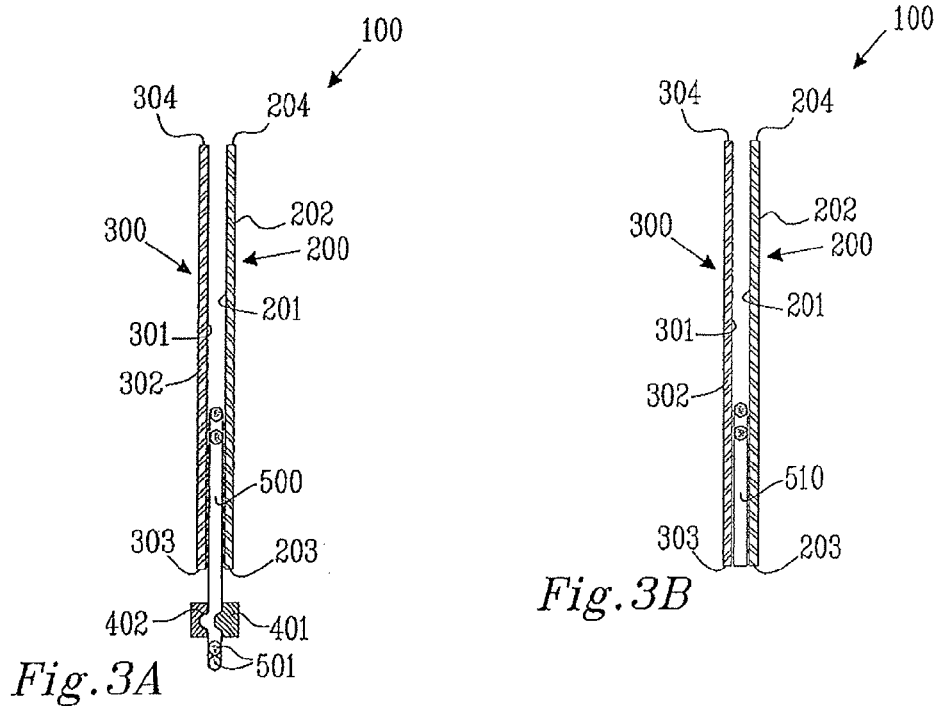
Fig.3
Fig.3A
Fig.3B

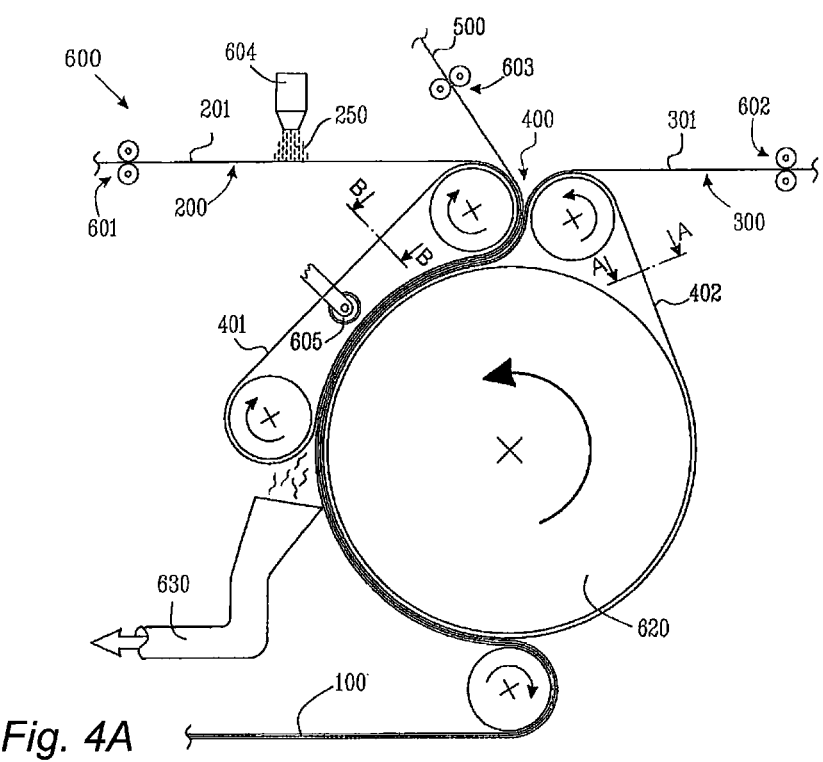
Fig. 4A
Fig. 4B

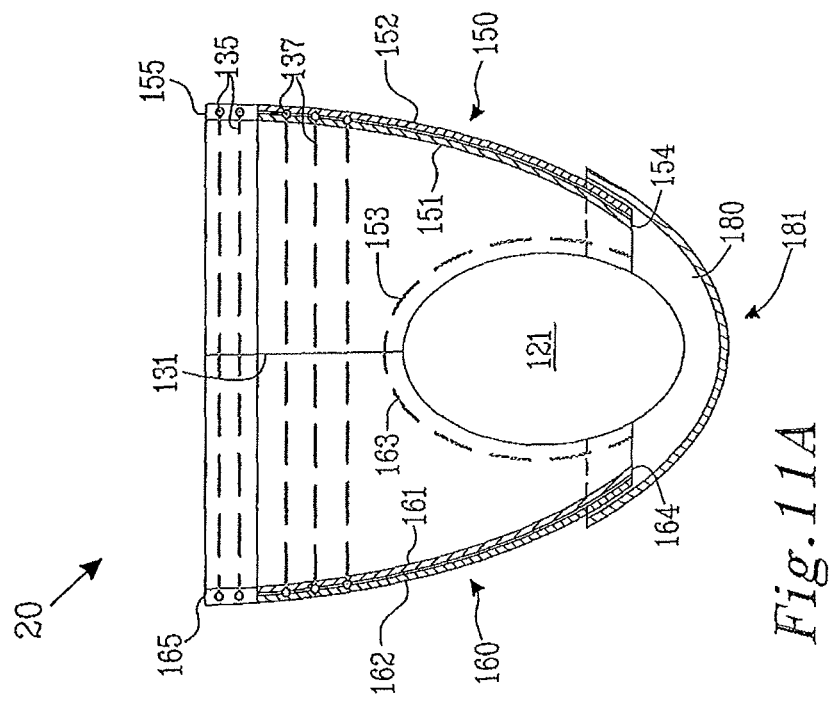
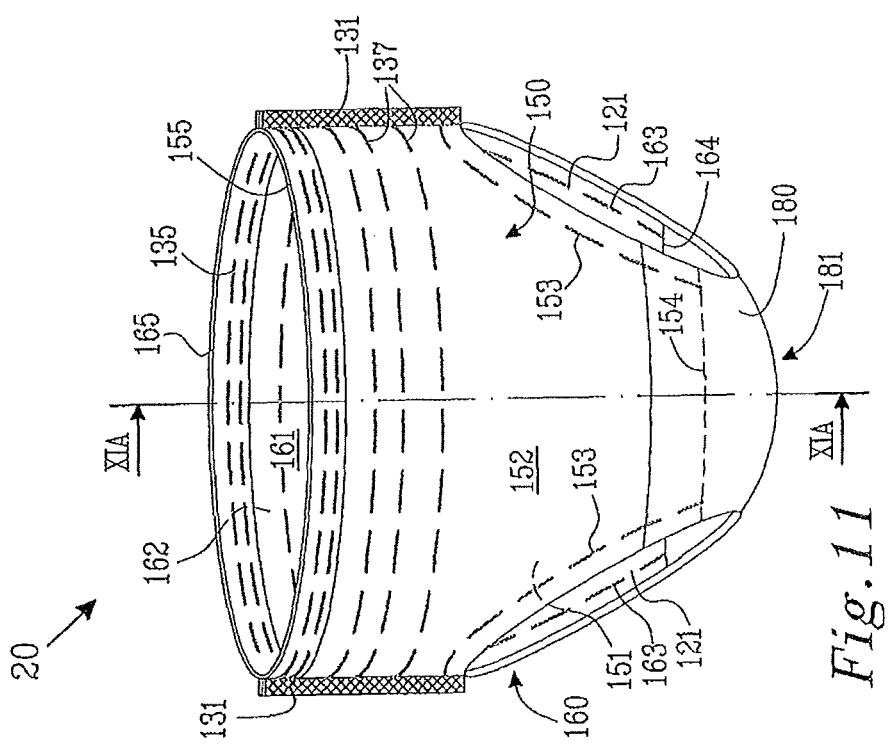
Fig. 11A
Fig. 11

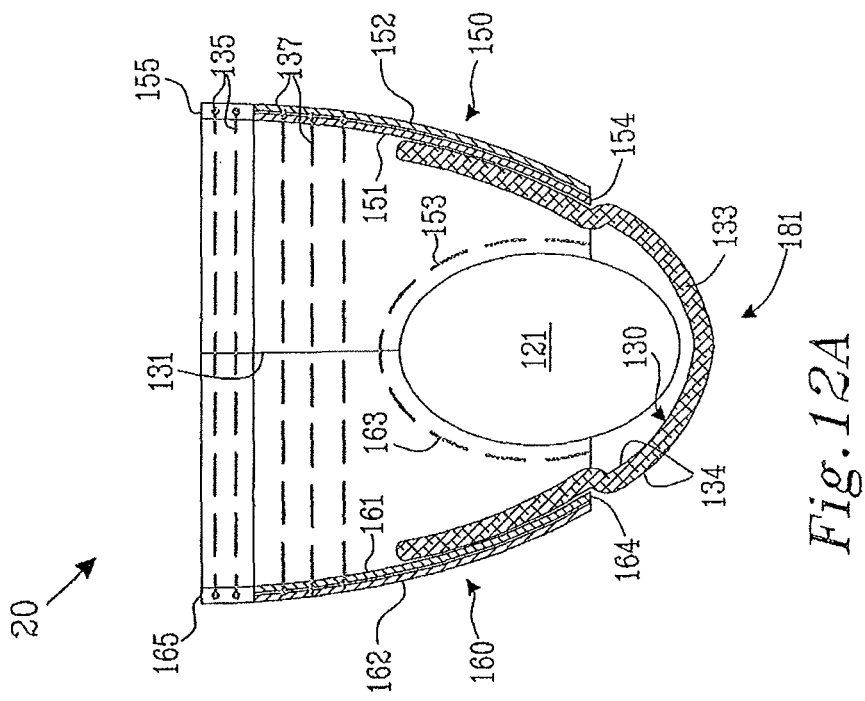
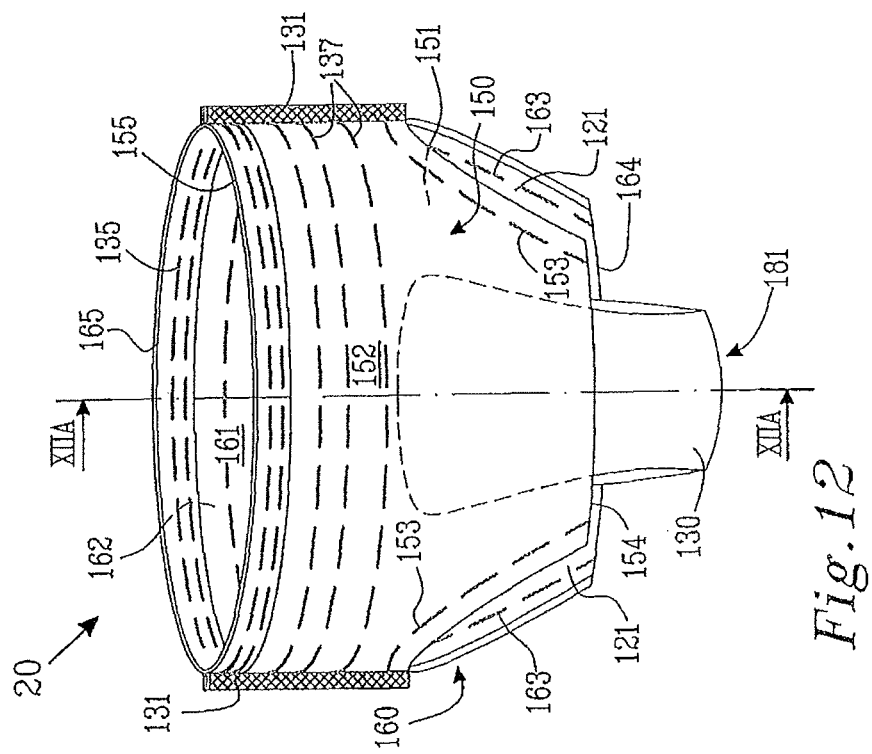

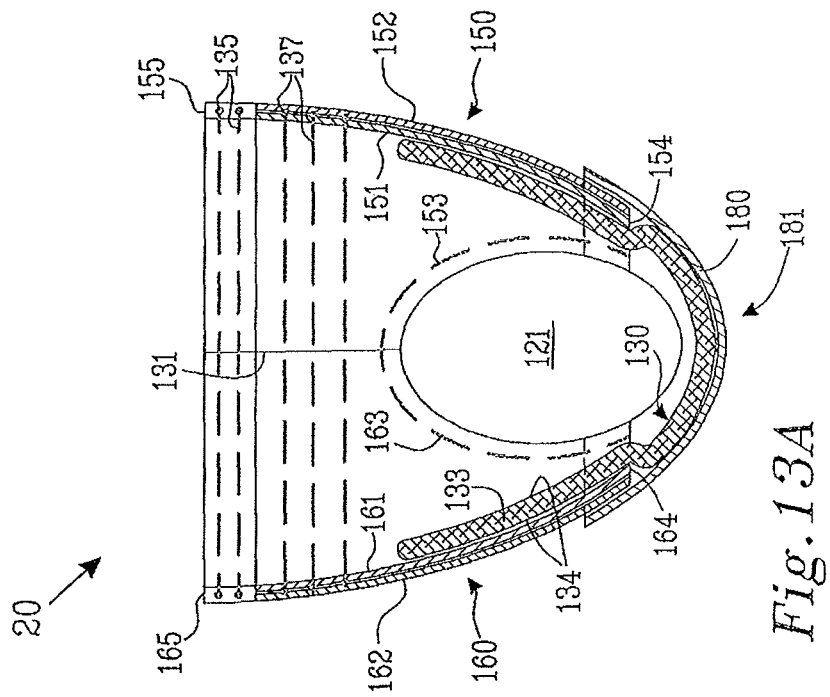
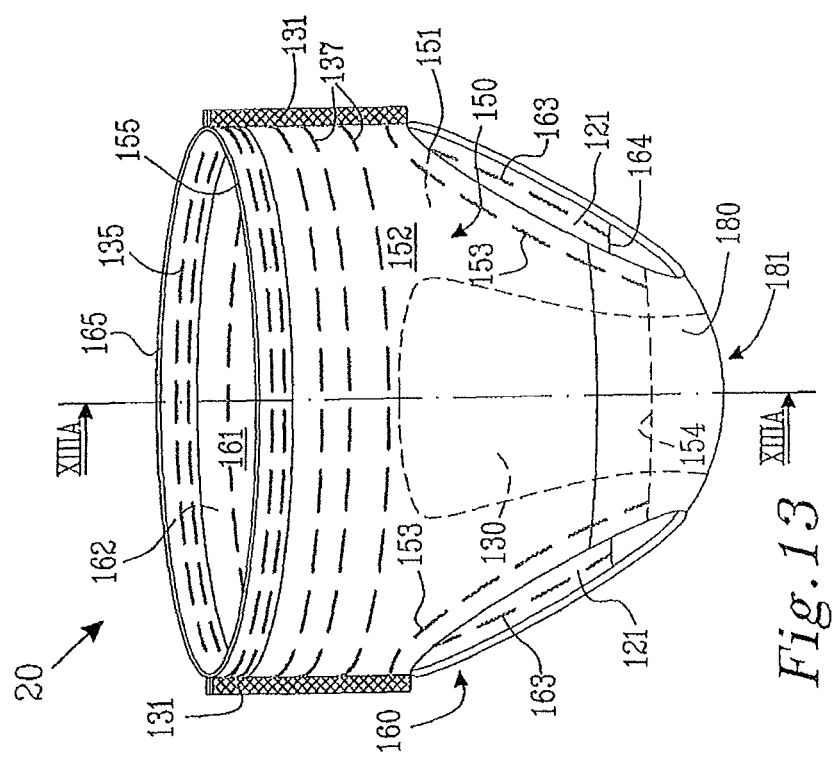
Fig. 13A
Fig. 13

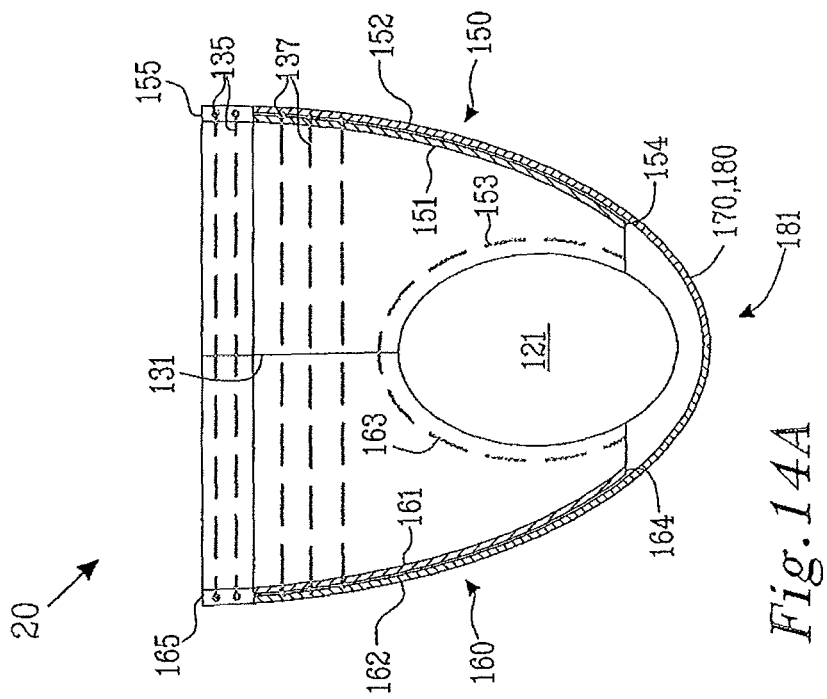
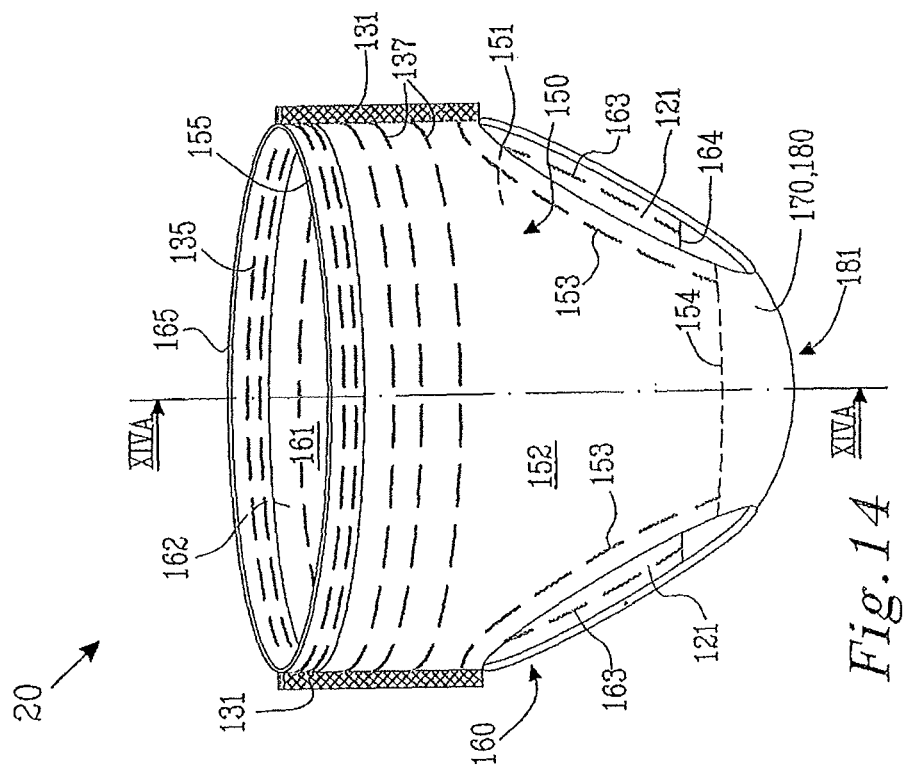

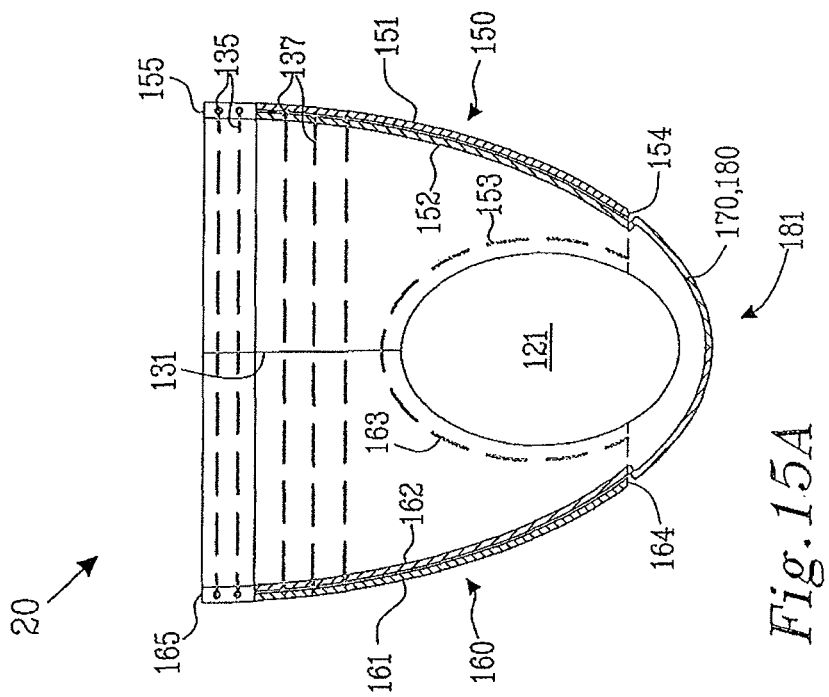
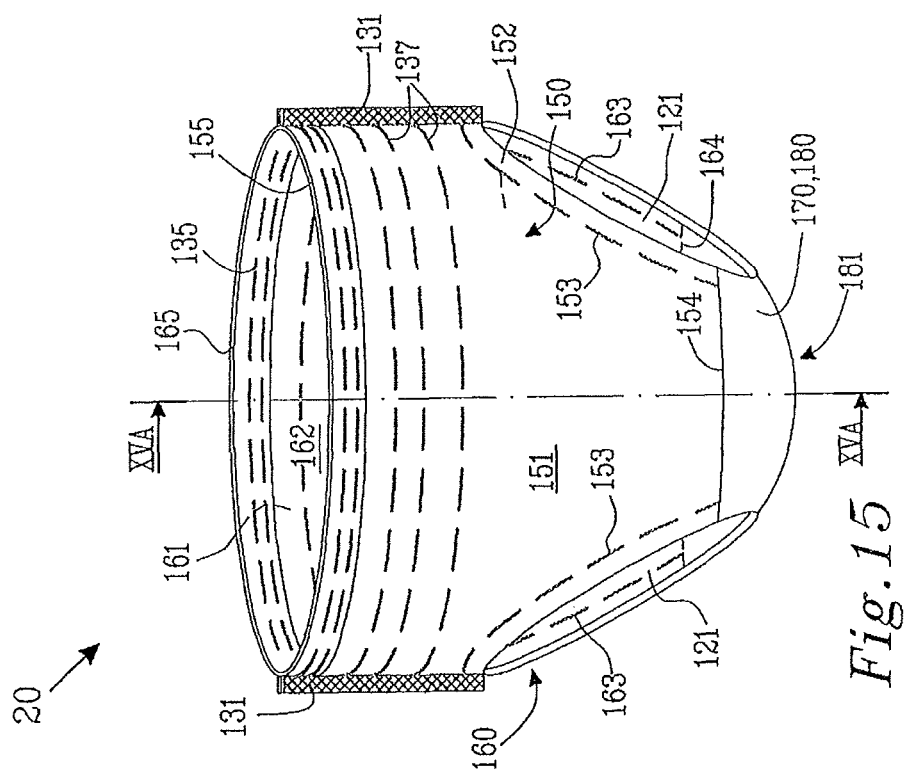
Fig. 15
Fig. 15A

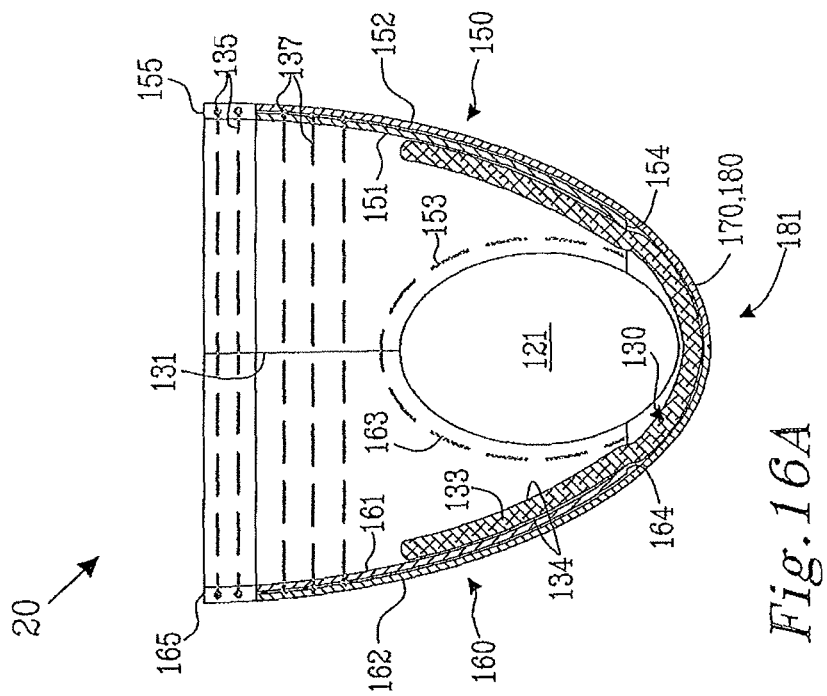
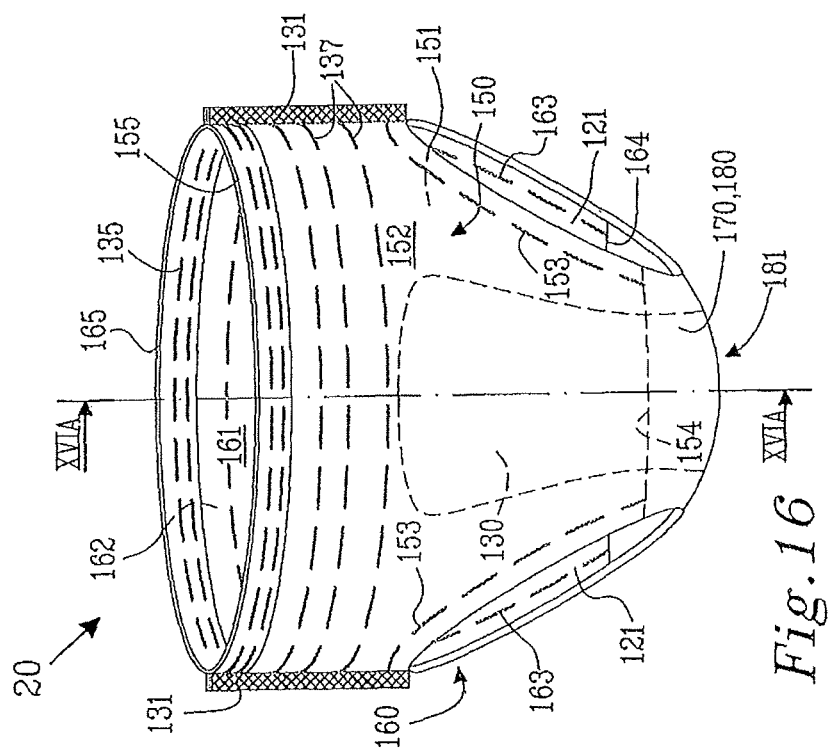

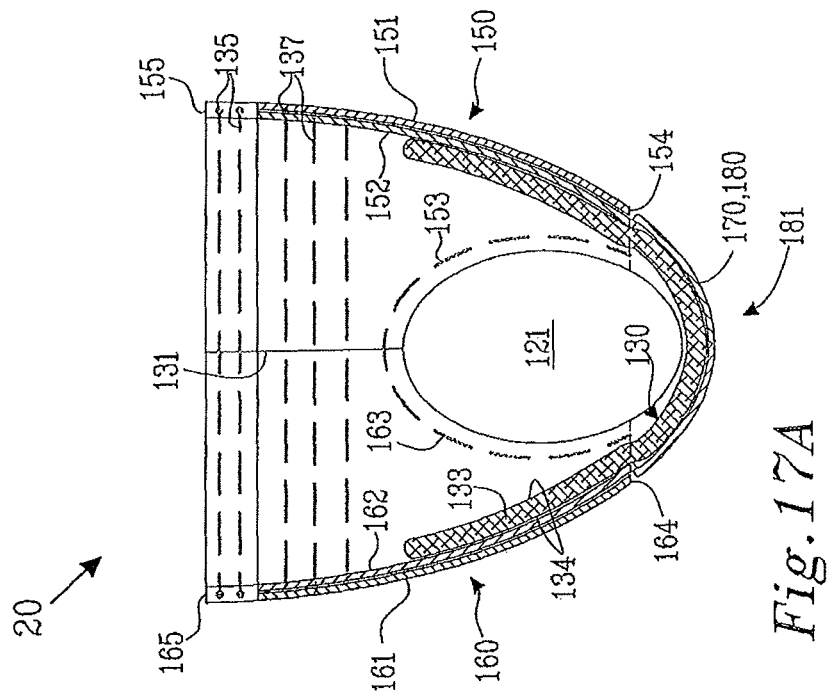
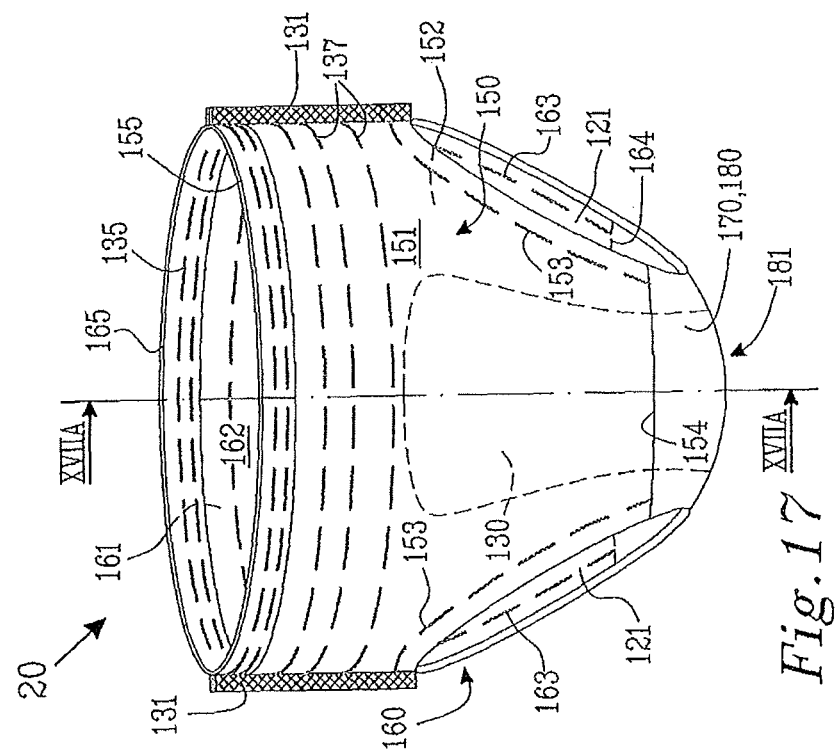

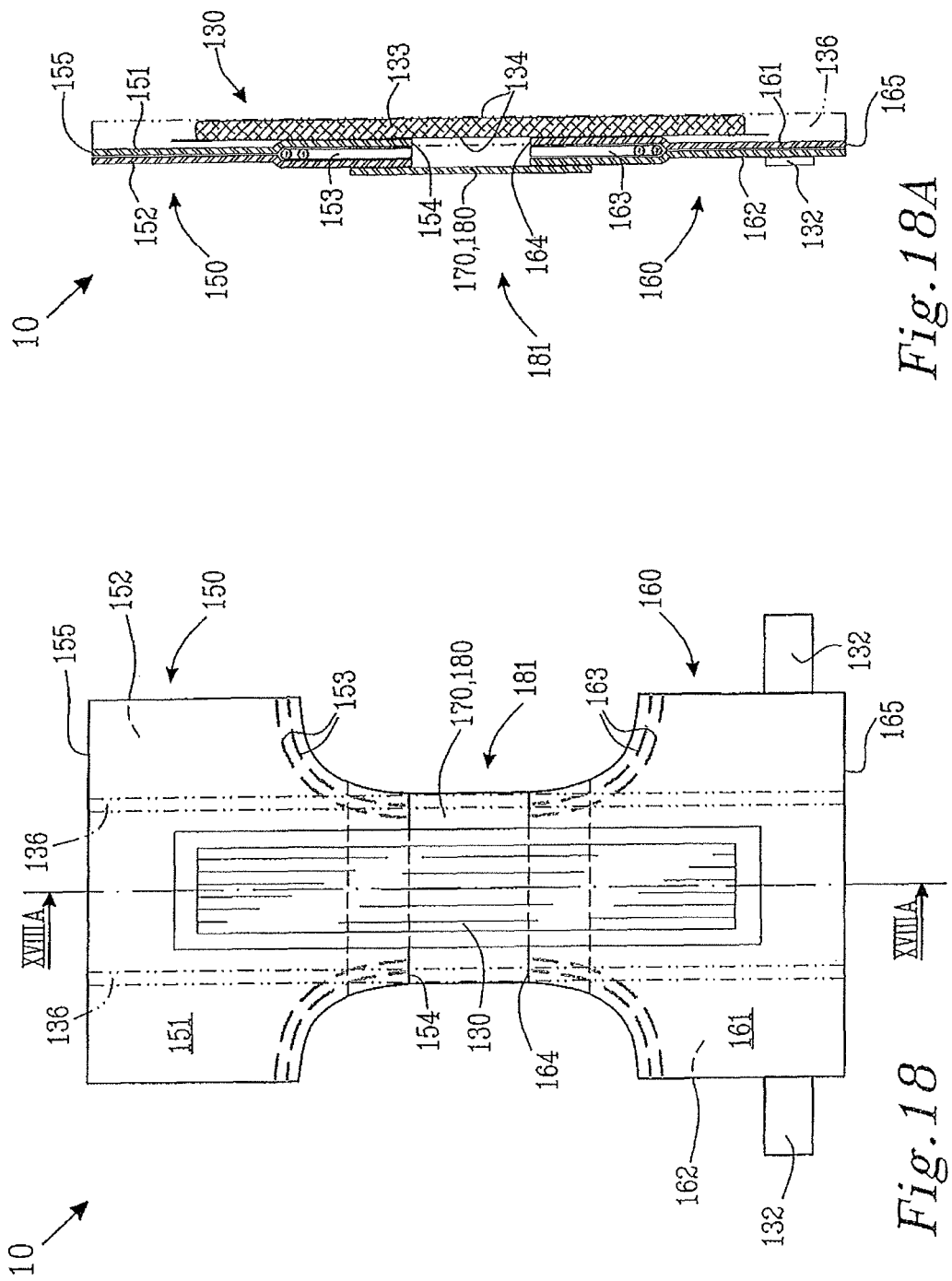

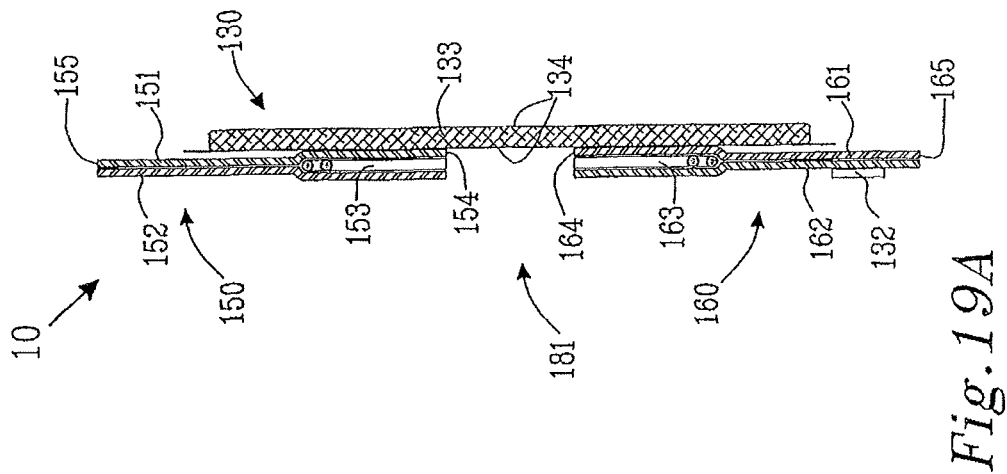
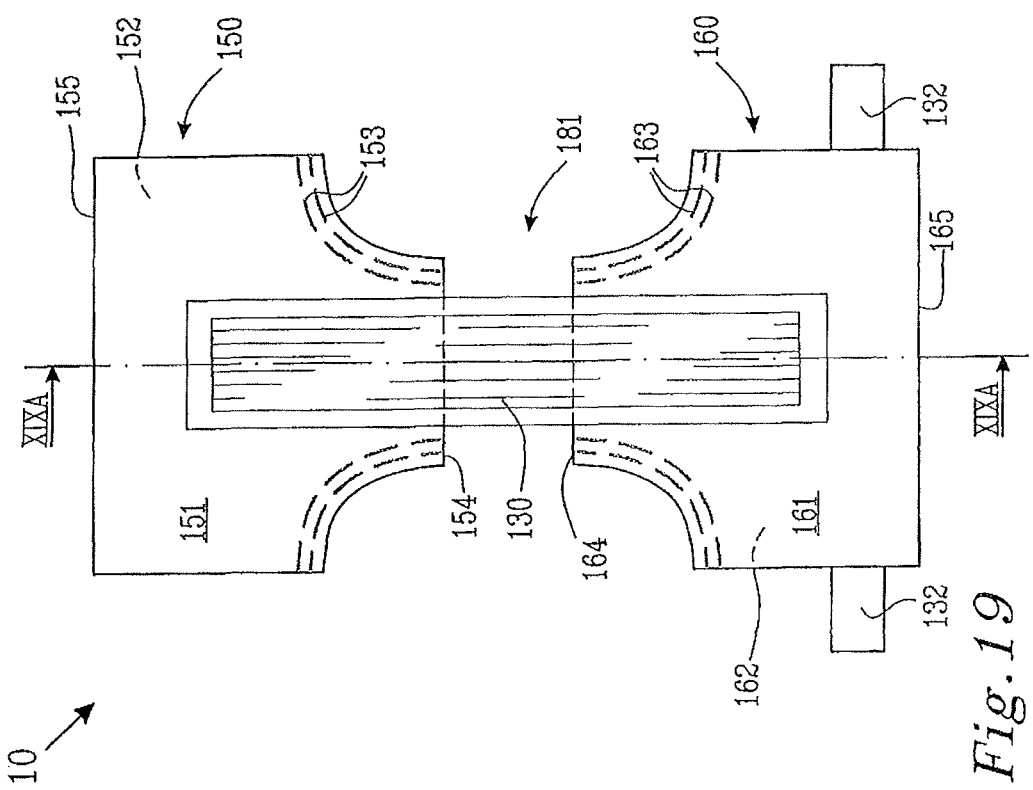
Fig.19A
Fig.19

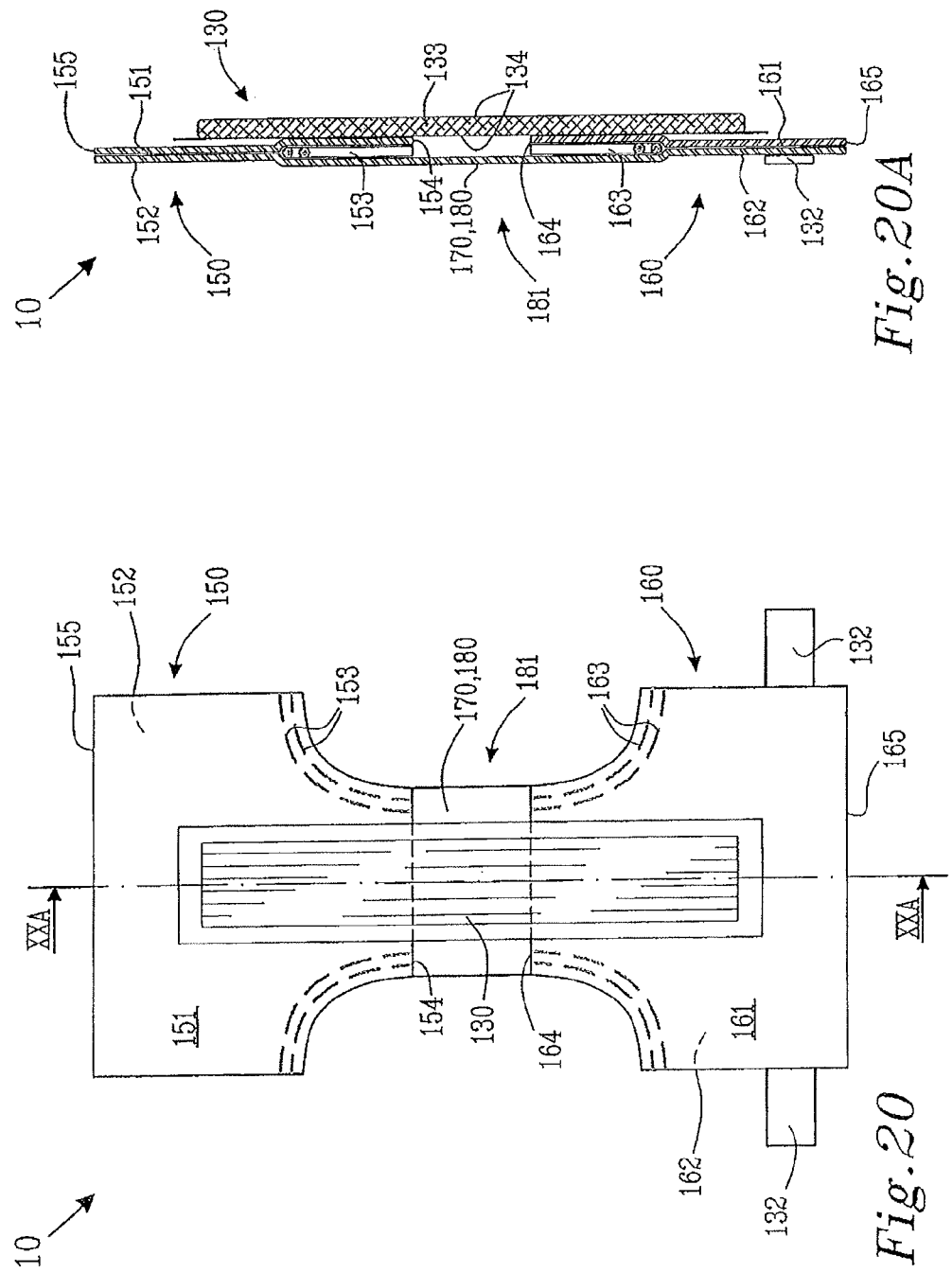

METHOD AND APPARATUS FOR PROVIDING A DIAPER

CROSS-REFERENCE TO PRIOR APPLICATION

This application is a §371 National Stage Application of PCT International Application No. PCT/SE2009/050468 filed Apr. 30, 2009, which is incorporated herein in its entirety.

TECHNICAL FIELD

The present disclosure relates to methods for manufacturing an elasticated web. The disclosure further relates to an apparatus for forming said elasticated web. The disclosure also relates to methods for manufacturing an absorbent article. The disclosure also relates to elasticated webs and absorbent articles which can be manufactured using the methods.

BACKGROUND

Absorbent articles, such as diapers or incontinence guards, are articles which are worn adjacent the body, and used for the containment and absorption of bodily exudates, such as urine, blood, faeces and sweat. Such articles are usually supplied with elastic members (commonly in the form of one or more elastic threads). In the interests of manufacturing efficiency and economy, the elastic members are located in selected regions of the article, such as leg openings, waist openings, standing gathers etc. Elastic members have a number of functions—they inter alia help to maintain the article in place on the wearer, they provide the article with a suitable three-dimensional form and they help to seal portions of the article against the skin of the wearer, thus reducing the risk of leakage.

Absorbent articles are manufactured in high volumes, at high speeds. Methods are therefore required which allow the incorporation of elastic members (e.g. in the form of one or more elastic threads) into or onto other components of an absorbent article during manufacture. Elastic members are usually only located in regions of the absorbent article, but are often supplied in continuous form (e.g. on a roll), so one or more steps of cutting the elastic members is usually required. This in turn leads to difficulties in maintaining the correct tension in the elastic members, and may cause crumpling, foreshortening or wrinkling of the elasticated components.

A particular issue is found with elastic members located in the crotch portion of absorbent articles—i.e. that portion which is located between the wearer's legs when the article is worn. It is generally undesirable that elastic members are located in the crotch portion, as they can cause chafing/rubbing in this sensitive area. In addition, elastic members which are arranged across an absorbent core can cause the core to deform. This in turn causes problems in terms of appearance (due to bunching) and liquid handling (due to undesired compression of the absorbent core causing liquid-channelling creases).

U.S. Pat. Nos. 5,660,657 and 5,643,396 disclose methods for constructing garments comprising stretched elastic. U.S. Pat. No. 4,379,016 describes a method and device for applying elastic strips in sections onto a web of material. U.S. Pat. No. 6,179,946 describes a process for making a composite sheet. U.S. Pat. No. 6,482,278 and U.S. Pat. No. 6,521,320 disclose pant-type diapers, and methods for their manufacture.

SUMMARY

The present disclosure aims to address the shortcomings associated with the prior art. In particular, the present disclosure aims to provide a method for providing an elasticated web having discontinuous elastic threads, in which the tension in the elastic threads can be readily controlled, in which cutting of the elastic threads can be accurately controlled, and in which material wastage is minimised. The process should occur without having to remove or add any non-elastic material. In addition, it is advantageous to be able to control the fate of waste material, particularly at the disposal stage. Desirably, the method can be implemented on known or commercially-available machinery without substantial changes to said machinery. These, and further advantages will be apparent from the following description and claims.

In a first aspect, a method for manufacturing an elasticated web is provided having discontinuous elastic threads. The method includes the steps of:

a. providing a first web, said first web having a primary extension in the machine direction, first and second faces and a first edge and a second edge, said first and second edges extending in the machine direction;

b. providing a second web, said second web also having a primary extension in the machine direction, first and second faces and a first edge and a second edge, said first and second edges extending in the machine direction;

c. applying a first adhesive to at least a portion of the first face of said first web;

d. applying at least one elastic thread on at least the portion of said first face of said first web which includes said first adhesive; wherein said at least one thread is applied in a pattern, said pattern oscillating in the cross-direction and extending in the machine direction, such that the pattern extends over the first edge of the first web to form loops in said elastic thread which project in the cross-direction from said first edge of said first web;

e. securing the loops in a loop retaining means which is located adjacent the first edge of said first web;

f. applying the first face of said second web on the first face of said first web, and fixing said first and second webs together such that said at least one elastic thread is partly sandwiched between the first faces of said respective first and second webs;

g. cutting the elastic thread substantially at each point at which the elastic thread crosses the first edge of said first web such that the loops become detached from the first web; so as to thereby provide an elasticated web having discontinuous elastic threads.

Steps d., e., and f. of the method may occur substantially simultaneously in a single nip. In a particular embodiment, the loop retaining means includes at least one first and at least one second resilient belt which are located adjacent the first edge of said first web. Suitably, the second web is applied to the first web such that the first edge of the second web is substantially aligned with the first edge of the first web.

A method for manufacturing pant-type articles from the elasticated web is also provided. This method includes the steps of;

a. carrying out the method above, so to provide an elasticated web, said elasticated web having first and second edges extending in the machine direction; said elasticated web also having discontinuous elastic threads, said discontinuous elastic threads being sandwiched between the first faces of respective first and second webs and extending to the first edge of said elasticated web;

b. arranging first and second such elasticated webs adjacent one another and in a spaced relationship such that first edges of each of said elasticated webs are located closest to one another and aligned substantially parallel to one another; said first and second elasticated webs being synchronised such that each discontinuous elastic thread in the first elasticated web is located opposite a corresponding discontinuous elastic thread in the second elasticated web;

c. placing a fourth web and/or an absorbent packet so as to overlie at least a portion of the first and/or second elasticated webs, and fixing at least one of said fourth web and/or said absorbent packet to both first and second elasticated webs;

d. cutting out leg regions of one or both elasticated webs and—if present—said fourth web; each leg region being defined substantially within said elasticated webs by discontinuous elastic threads;

e. folding the co-joined elasticated webs along a fold-line, so that second edges of each elasticated web become arranged substantially adjacent one another and substantially parallel, with the fourth web located on the outside of the fold and/or the absorbent packet located on the inside of the fold;

f. joining the first and second elasticated webs to each other along cutting lines, said cutting lines extending substantially in the cross direction from the second edges of each elasticated web to the fold-line, said cutting lines being located substantially at the point at which the at least one discontinuous elastic thread is located furthest from the first edge of each elasticated web; to form side-seams;

g. cutting each elasticated web, and—if present—the fourth web, along cutting lines such that first and second elasticated webs remain joined on either side of the cut, so as to provide pant-type articles.

A method for manufacturing absorbent articles from the elasticated web is also provided. This method includes the steps of;

a. carrying out the method above, so to provide an elasticated web, said elasticated web having first and second edges extending in the machine direction; said elasticated web also having discontinuous elastic threads in which discontinuous elastic threads are sandwiched between the first faces of respective first and second webs and extend to the first edge of said elasticated web;

b. arranging first and second such elasticated webs adjacent one another and in a spaced relationship such that first edges of each of said elasticated webs are located closest to one another and aligned substantially parallel to one another; said first and second elasticated webs being synchronised such that each discontinuous elastic thread in the first elasticated web is located opposite a corresponding discontinuous elastic thread in the second elasticated web;

c. placing an absorbent packet so as to overlie at least a portion of the first and/or second elasticated webs;

d. optionally, placing a fourth web so as to overlie the first edges of the first and second elasticated webs, and fixing at least one of said fourth web and/or said absorbent packet to both first and second elasticated webs;

e. cutting out leg regions of said fourth web and optionally said first and/or second elasticated webs; each leg region being defined substantially within said elasticated webs by discontinuous elastic threads;

f. cutting the co-joined elasticated webs and—if present—the fourth web along cutting lines, said cutting lines extending substantially in the cross direction from the second edge of one elasticated web to the second edge of the other elasticated web, said cutting lines being located substantially at the point at which the at least one discontinuous elastic thread is located furthest from the first edge of each elasticated web;

g. providing fastening means on at least one of said first and second elasticated webs; so as to provide absorbent articles.

The disclosure also provides a method for manufacturing an elasticated web having discontinuous elastic threads. The method includes the steps of:

providing a first web, said first web having a primary extension in the machine direction, first and second faces and a first edge and a second edge, said first and second edges extending in the machine direction;

providing a second web, said second web also having a primary extension in the machine direction, first and second faces and a first edge and a second edge, said first and second edges extending in the machine direction;

providing a third web said third web having a primary extension in the machine direction, first and second faces and a first edge and a second edge, said first and second edges extending in the machine direction;

arranging said third web to lie adjacent and substantially parallel with said first web, in a spaced arrangement with the first faces of said webs facing the same direction, such that the first edges of respective first and third webs are adjacent;

applying a first adhesive to at least a portion of the first face of said first web or to at least a portion of the first face of the second web;

applying a second adhesive to at least a portion of the first face of said third web or to at least a portion of the first face of the second web;

applying at least one first elastic thread on at least the portion of said first face of said first web or on at least the portion of said first face of said second web which includes said first adhesive; wherein said at least one first thread is applied in a first pattern, said first pattern oscillating in the cross-direction and extending in the machine direction, applying at least one second elastic thread on at least the portion of said first face of said third web or to at least the portion of said first face of said second web which includes said second adhesive; wherein said at least one second elastic thread is applied in a second pattern, said second pattern oscillating in the cross-direction and extending in the machine direction, applying a portion of the first face of said second web on the first face of said first web, and fixing said first and second webs together such that said at least one first elastic thread is partly sandwiched between the first faces of respective first and second webs; such that the first pattern extends over the first edge of the first web to form first loops in said first elastic thread which project in the cross-direction from said first edge of said first web;

applying a portion of the first face of said second web on the first face of said third web, and fixing said third and second webs together such that said at least one second elastic thread is partly sandwiched between the first faces of respective second and third webs; such that the second pattern extends over the first edge of the third web to form second loops in said second elastic thread which project in the cross-direction from said first edge of said third web; and such that said first and second patterns are synchronised such that the point in the machine direction at which the first elastic threads are located furthest from the first edge of the first web corresponds substantially to the point in the machine direction at which the second elastic threads are located furthest from the first edge of the third web;

securing the first loops of said first elastic threads in a first loop retaining means located adjacent the first edge of said first web;

securing the second loops of said second elastic threads in a second loop retaining means located adjacent the first edge of said third web;

cutting all the first elastic threads substantially at the point at which each first elastic thread crosses the first edge of said first web such that the loops become detached from the first web;

cutting all the second elastic threads substantially at the point at which each second elastic thread crosses the first edge of said third web such that the loops become detached from the third web;

Step d. can take place at any point in the process before step i. so as to provide an elasticated web having discontinuous elastic threads.

Steps e.-l. of this method may occur substantially simultaneously in a single nip.

In a particular embodiment, the first loop retaining means includes at least one first and at least one second resilient belt which are located adjacent the first edge of said first web. Similarly the second loop retaining means may include at least one third and at least one fourth resilient belt which are located adjacent the first edge of said third web. As a further option, a single wide resilient belt may include the third resilient belt and the first resilient belt, and a single wide resilient belt may include the fourth resilient belt and the second resilient belt.

The disclosure also provides a method for manufacturing pant-type articles from the elasticated web. This method includes the steps of:
  a. carrying out the method above, so to provide an elasticated web having discontinuous elastic threads in which at least one first discontinuous elastic thread is sandwiched between the first faces of respective first and second webs; and at least one second discontinuous elastic thread is sandwiched between the first faces of respective third and second webs;
  b. cutting out a leg region of the elasticated web defined substantially between discontinuous elastic threads of the first and third webs so as to form leg openings;
  c. folding the elasticated web along a fold-line, so that first and second edges of the elasticated web become arranged substantially adjacent one another and substantially parallel;
  d. joining the folded elasticated web along cutting lines, said cutting lines extending substantially in the cross direction from the first and second edges of the elasticated web to the fold-line, said cutting lines being located substantially at the point at which the discontinuous elastic threads are located furthest from the fold-line; to form side-seams;
  e. cutting the elasticated web along cutting lines such that the elasticated web remain joined on either side of the cut;

Steps b. and c. can take place in any order, so as to thereby provide pant-type articles.

This method may include the additional step of: placing an absorbent packet so as to overlie at least a portion of the first web, second and/or the third web, and fixing said absorbent packet to at least one of said first, second and/or third webs; after step a., but before step c.

The disclosure also provides a method for manufacturing absorbent articles from the elasticated web. The method includes the steps of
  a. carrying out the method above, so to provide an elasticated web having discontinuous elastic threads in which at least one first discontinuous elastic thread is sandwiched between the first faces of respective first and second webs; and at least one second discontinuous elastic thread is sandwiched between the first faces of respective third and second webs;
  b. placing an absorbent packet so as to overlie at least a portion of the first web, second and/or the third web, and fixing said absorbent packet to at least one of said first, second and/or third webs;
  c. cutting out a region of the elasticated web defined substantially between discontinuous elastic threads of the first and third webs, so as to form leg openings;
  d. providing fastening means on said elasticated web;
  e. cutting the elasticated web along cutting lines said cutting lines extending substantially in the cross direction from the first edge to the second edge of the elasticated web, said cutting lines being located substantially at the point at which the discontinuous elastic threads are located furthest from the first edges of the first and third webs; so as to provide absorbent articles.

The disclosure also provides an elasticated web having discontinuous elastic threads. The elasticated web includes:
  a. a first web, said first web having a primary extension in the machine direction, first and second faces and a first edge and a second edge, said first and second edges extending in the machine direction;
  b. a second web, said second web also having a primary extension in the machine direction, first and second faces and a first edge and a second edge, said first and second edges extending in the machine direction;
  c. a first adhesive arranged on at least a portion of the first face of said first web; and
  d. at least one discontinuous elastic thread arranged on at least the portion of said first face of said first web which includes said first adhesive.

The first face of said second web overlies the first face of said first web; said first and second webs being fixed together such that said at least one discontinuous elastic thread is sandwiched between the first faces of said respective first and second webs.

At least one discontinuous thread is present in a pattern, said pattern forming loops which extend from the first edge of the first web and back to said first edge of the first web; so that the discontinuous elastic threads terminate at each point at which they meet the first edge of said first web.

Furthermore, the disclosure provides an elasticated web having discontinuous elastic threads. This elasticated web includes:
  a. a first web, said first web having a primary extension in the machine direction, first and second faces and a first edge and a second edge, said first and second edges extending in the machine direction;
  b. a second web, said second web having a primary extension in the machine direction, first and second faces and a first edge and a second edge, said first and second edges extending in the machine direction;
  c. a third web, said third web having a primary extension in the machine direction, first and second faces and a first edge and a second edge, said first and second edges extending in the machine direction;

d. a first adhesive arranged on at least a portion of the first face of said first web or on at least a portion of the first face of said second web;
e. at least one discontinuous elastic thread arranged on at least the portion of said first face of said first web or on at least the portion of the first face of said second web which includes said first adhesive;
f. a second adhesive arranged on at least a portion of the first face of said third web or on at least a portion of the first face of said second web;
g. at least one discontinuous elastic thread arranged on at least the portion of said first face of said third web or on at least the portion of the first face of said second web which includes said second adhesive;
h. said third web lying adjacent and substantially parallel with said first web, in a spaced arrangement with the first faces of said webs facing the same direction, such that the first edges of respective first and third webs are adjacent;

The first face of said second web overlies the first face of said first web; said first and second webs being fixed together such that said at least one discontinuous elastic thread is sandwiched between the first faces of said respective first and second webs;

The first face of said second web also overlies the first face of said third web; said third and second webs being fixed together such that said at least one discontinuous elastic thread is sandwiched between the first faces of said respective third and second webs.

The at least one discontinuous elastic thread is present in a first pattern, said first pattern forming loops which extend from the first edge of the first web and back to said first edge of the first web; so that the discontinuous elastic threads terminate at each point at which they meet the first edge of said first web. In addition, the at least one discontinuous thread is present in a second pattern, said second pattern forming loops which extend from the first edge of the third web and back to said third edge of the third web; so that the discontinuous elastic threads terminate at each point at which they meet the first edge of said third web.

The disclosure also provides a pant-type article, including:
a front panel,
a rear panel;
a crotch panel, said crotch panel extending between said front panel and said rear panel in the longitudinal direction of the pant-type article and being joined to said front and rear panels.

The crotch panel includes a crotch layer, and/or an absorbent packet.

The front and rear panels are joined at side seams at the transverse edges thereof.

At least said front panel includes a first front layer, a second front layer and at least two first leg elastics located between said first and second front layers; wherein said at least two first leg elastics are located on either side of a longitudinal centre line of the pant-type article.

The first front layer is defined by first and second edges which extend substantially in the transverse direction of the pant-type article; said first edge being that which is located closest to the crotch panel of the pant-type article.

The rear panel 160 also includes a first rear layer, a second rear layer and at least two second leg elastics located between said first and second rear layers; wherein said at least two second leg elastics are located on either side of longitudinal centre line of the pant-type article;

The first rear layer is defined by first and second edges which extend substantially in the transverse direction of the pant-type article; said first edge being that which is located closest to the crotch panel of the pant-type article.

The first leg elastics in said front panel terminate at the point at which they meet the first edge of said first front layer and the second leg elastics in said rear panel terminate at the point at which they meet the first edge of said first rear layer.

In the above pant-type article, said at least two first leg elastics and said at least two second leg elastics may be located on either side of the absorbent packet of the pant-type article in the transverse direction. Additionally, a single second layer may include the second front layer, the second rear layer and the crotch layer.

In addition, the disclosure provides an absorbent article, including:
a front panel,
a rear panel;
a crotch panel, said crotch panel extending between said front panel and said rear panel in the longitudinal direction of the absorbent article and being joined to said front and rear panels.

The crotch panel includes an absorbent packet, and optionally, a crotch layer.

At least one of said front and rear panels includes fastening means.

At least said front panel includes a first front layer, a second front layer and at least two first leg elastics located between said first and second front layers; wherein said at least two first leg elastics are located on either side of a longitudinal centre line of the absorbent article.

The first front layer is defined by first and second edges which extend substantially in the transverse direction of the absorbent article; said first edge being that which is located closest to the crotch panel of the absorbent article.

The rear panel also includes a first rear layer, a second rear layer and at least two second leg elastics located between said first and second rear layers; wherein said at least two second leg elastics are located on either side of longitudinal centre line of the absorbent article.

The first rear layer is defined by first and second edges which extend substantially in the transverse direction of the absorbent article; said first edge being that which is located closest to the crotch panel of the absorbent article.

The first leg elastics in said front panel terminate at the point at which they meet the first edge of said first front layer and the second leg elastics in said rear panel terminate at the point at which they meet the first edge of said first rear layer.

In the absorbent article above, said at least two first leg elastics and said at least two second leg elastics are located on either side of the absorbent packet of the absorbent article in the transverse direction. A single second layer may include the second front layer, the second rear layer and the crotch layer.

The disclosure provides an apparatus for carrying out the first method. The apparatus includes:
first web supply means, for supplying said first web;
second web supply means, for supplying said second web;
elastic thread supply means for supplying said at least one elastic thread;
adhesive supply means for supplying said first adhesive;
elastic cutting means for cutting said at least one elastic thread The adhesive supply means is arranged so as to apply a first adhesive to at least a portion of the first face of said first web.

The elastic thread supply means is arranged so as to apply at least one elastic thread on at least the portion of said first face of said first web which includes said first adhesive; wherein said at least one thread is applied in a pattern, said pattern oscillating in the cross-direction and extending in the machine direction, such that the pattern extends over the first edge of the first web to form loops in said elastic threads which project in the cross-direction from said first edge of said first web.

The second web supply means is arranged so as to apply the first face of said second web on the first face of said first web, and fix said first and second webs together such that said at least one elastic thread is partly sandwiched between the first faces of respective first and second webs.

The elastic cutting means arranged so as to cut all the elastic threads substantially at the point at which each elastic thread crosses the first edge of said first web such that the loops become detached from the first web.

The apparatus additionally includes loop retaining means located adjacent the first edge of said first web and which is adapted so as to secure the loops in said loop retaining means.

The first and second webs may be fixed together in a single nip. The loop retaining means suitably includes at least one first and at least one second resilient belt which are located adjacent the first edge of said first web; and which are adapted so as to secure the loops in a nip between said at least one first and said at least one second resilient belt.

Additionally,
first web supply means;
second web supply means;
elastic thread supply means for supplying at least one elastic thread;
adhesive supply means;
cutting means; and
loop retaining means
may be arranged peripherally about a single central cylinder.

The disclosure also provides an apparatus, for manufacturing pant-type articles, said apparatus additionally including;
elasticated web supply means; for supply of first and second elasticated web;
fourth web supply means, for supply of fourth web and/or absorbent packet supply means, for supply of absorbent packets;
leg region cutting means, for cutting out leg regions;
folding means for folding the co-joined elasticated webs;
joining means for joining the first and second elasticated webs;
elasticated web cutting means, for cutting elasticated webs and—if present—the fourth web.

The elasticated web supply means is arranged so as to provide first and second elasticated webs adjacent one another and in a spaced relationship such that the first edges of each of said elasticated webs are located closest to one another and aligned substantially parallel to one another; said first and second elasticated webs being synchronised such that each discontinuous elastic thread in the first elasticated web is located opposite a corresponding discontinuous elastic thread in the second elasticated web.

The fourth web supply means, for supply of fourth web is arranged so as to place a fourth web so as to overlie the first edges of the first and second elasticated webs, and to fix said fourth web to both first and second elasticated webs.

The absorbent packet supply means is arranged so as to place an absorbent packet so as to overlie at least a portion of the first or second elasticated webs, and to fix said absorbent packet to at least one of said first and second elasticated webs; such that at least one of said fourth web and/or said absorbent packet is fixed to both first and second elasticated webs.

The leg region cutting means is arranged so as to cut out a leg region of one or both elasticated webs and—if present—said fourth web; each leg region being defined substantially by discontinuous elastic threads so as to form leg openings.

The folding means is arranged so as to fold the co-joined elasticated webs along a fold-line, so that second edges of each elasticated web become arranged substantially adjacent one another and substantially parallel, with the fourth web located on the outside of the fold and/or the absorbent packet located on the inside of the fold.

The joining means being arranged so as to join the first and second elasticated webs to each other along cutting lines, said cutting lines extending substantially in the cross direction from the second edges of each elasticated web to the fold-line, said cutting lines being located substantially at the point at which the at least one discontinuous elastic thread is located furthest from the first edge of each elasticated web; to form side-seams.

The elasticated web cutting means is arranged so as to cut each elasticated web and—if present—the fourth web, along cutting lines such that first and second elasticated webs remain joined on either side of the cut.

Additionally, an apparatus is provided, for manufacturing absorbent articles in the form of open diapers. This apparatus additionally includes;
elasticated web supply means; for supply of first and second elasticated web;
absorbent packet supply means, for supply of absorbent packets;
optionally, fourth web supply means, for supply of fourth web;
leg region cutting means, for cutting out leg regions;
elasticated web cutting means, for cutting elasticated webs and—if present—the fourth web; and
fastening supply means, for supply of fastening means.

The elasticated web supply means is arranged so as to provide first and second elasticated webs adjacent one another and in a spaced relationship such that the first edges of each of said elasticated webs are located closest to one another and aligned substantially parallel to one another. The first and second elasticated webs are synchronised such that each discontinuous elastic thread in the first elasticated web is located opposite a corresponding discontinuous elastic thread in the second elasticated web.

The absorbent packet supply means is arranged so as to place an absorbent packet so as to overlie at least a portion of the first or second elasticated webs.

The fourth web supply means, for supply of fourth web is arranged so as to place a fourth web so as to overlie the first edges of the first and second elasticated webs, and fixing at least one of said fourth web and/or said absorbent packet to both first and second elasticated webs.

The leg region cutting means is arranged so as to cut out a leg region of one or both elasticated webs and—if present—said fourth web; each leg region being defined substantially by discontinuous elastic threads so as to form leg openings.

The elasticated web cutting means is arranged to cut the co-joined elasticated webs and—if present—the fourth web along cutting lines, said cutting lines extending substantially in the cross direction from the second edge of one elasticated web to the second edge of the other elasticated web. The cutting lines are located substantially at the point at which the at least one discontinuous elastic thread is located furthest from the first edge of each elasticated web.

The fastening supply means is arranged so as to provide fastening means on at least one of said first and second elasticated webs 100.

An apparatus is also provided for manufacturing the elasticated web. Said apparatus includes:

first web supply means, for supplying said first web;
second web supply means, for supplying said second web;
third web supply means, for supplying said third web;
first elastic thread supply means for supplying said at least one first elastic thread;
second elastic thread supply means for supplying said at least one second elastic thread;
first adhesive supply means for supplying said first adhesive;
second adhesive supply means for supplying said second adhesive; and
cutting means for cutting said first and second elastic threads.

The first adhesive supply means is arranged so as to apply a first adhesive to at least a portion of the first face of said first web or to at least a portion of the first face of the second web.

The first elastic thread supply means is arranged so as to apply at least one first elastic thread on at least the portion of said first face of said first web or on at least the portion of said first face of said second web which includes said first adhesive; wherein said at least one first elastic thread is applied in a first pattern, said first pattern oscillating in the cross-direction and extending in the machine direction.

The second adhesive supply means is arranged so as to apply a second adhesive to at least a portion of the first face of the third web or to at least a portion of the first face of the second web.

The second elastic thread supply means is arranged so as to apply at least one second elastic thread on at least the portion of said first face of said third web or on at least the portion of said first face of said second web which includes said second adhesive; wherein said at least one second elastic thread is applied in a second pattern, said second pattern oscillating in the cross-direction and extending in the machine direction.

The second web supply means is arranged so as to apply the first face of said second web on the first face of said first web and the first face of said third web, and fix said first and second webs together; and said third and said second webs together; such that said at least one first elastic thread is partly sandwiched between the first faces of respective first and second webs; and said at least one second elastic thread is partly sandwiched between the first faces of respective third and second webs.

The first pattern extends over the first edge of the first web to form first loops in said first elastic threads which project in the cross-direction from said first edge of said first web.

The second pattern extends over the first edge of the third web to form second loops in said second elastic threads which project in the cross-direction from said first edge of said third web.

The first and second patterns are synchronised such that the point in the machine direction at which the first elastic threads are located furthest from the first edge of the first web corresponds substantially to the point in the machine direction at which the second elastic threads are located furthest from the first edge of the third web.

The cutting means is arranged so as to cut all the elastic threads substantially at the point at which each first elastic thread crosses the first edge of said first web such that the first loops become detached from the first web; and at the point at which each second elastic thread crosses the first edge of said third web; such that the second loops become detached from the third web.

The apparatus includes first loop retaining means located adjacent the first edge of said first web and which is adapted so as to secure the first loops in said first loop retaining means and second loop retaining means located adjacent the first edge of said third web and which is adapted so as to secure the second loops in said second loop retaining means.

The first loop retaining means may include at least one first and at least one second resilient belt which are located adjacent the first edge of said first web; and which are adapted so as to secure the first loops of the first elastic thread in a nip between said at least one first and said at least one second resilient belt.

Similarly, the second loop retaining means includes at least one third and at least one fourth resilient belt which are located adjacent the first edge of said third web; and which are adapted so as to secure the second loops of the second elastic thread in a nip between said at least one third and said at least one fourth resilient belt. Optionally, a single wide resilient belt may include the third resilient belt and the first resilient belt, and a single wide resilient belt includes the fourth resilient belt and the second resilient belt.

First, second and third webs may be fixed together in a single nip in the above apparatus.

In the apparatus above;
first web supply means, for supplying said first web;
second web supply means, for supplying said second web;
third web supply means, for supplying said third web;
first elastic thread supply means for supplying said at least one first elastic thread;
second elastic thread supply means for supplying said at least one second elastic thread;
first adhesive supply means for supplying said first adhesive;
second adhesive supply means for supplying said second adhesive;
cutting means for cutting said first and second elastic threads; and
first and second loop retaining means;
may be arranged peripherally about a single central cylinder.

An apparatus is also provided, for manufacturing pant-type articles from elasticated web. This apparatus additionally includes;
elasticated web supply means; for supply of said elasticated web;
optionally, absorbent packet supply means, for supply of absorbent packets;
leg region cutting means, for cutting out leg regions;
folding means for folding the elasticated web;
joining means for joining the elasticated web; and
elasticated web cutting means, for cutting elasticated web.

The elasticated web supply means is arranged so as to provide an elasticated web having discontinuous elastic threads in which at least one first discontinuous elastic thread is sandwiched between the first faces of respective first and second webs; and at least one second discontinuous elastic thread is sandwiched between the first faces of respective third and second webs.

The absorbent packet supply means is arranged so as to place an absorbent packet so as to overlie at least a portion of the first web, second web and/or the third web, and to fix said absorbent packet to at least one of said first, second and third webs.

The leg region cutting means is arranged so as to cut out a region of the elasticated web defined substantially between discontinuous elastic threads of the first and third webs 200, 700, so as to form leg openings.

The folding means is arranged so as to fold the elasticated web along a fold-line, so that first and second edges of the elasticated web become arranged substantially adjacent one another and substantially parallel.

The joining means is arranged so as to join the folded elasticated web along cutting lines, said cutting lines extending substantially in the cross direction from the first and second edges of the elasticated web to the fold-line, said cutting lines being located substantially at the point at which the discontinuous elastic threads are located furthest from the fold-line; to form side-seams.

The elasticated web cutting means is arranged so as to cut the elasticated web along cutting lines such that the elasticated web remain joined on either side of the cut.

An apparatus is also provided, for manufacturing absorbent articles in the form of open diapers from elasticated web. This apparatus additionally includes;
 elasticated web supply means; for supply of said elasticated web;
 absorbent packet supply means, for supply of absorbent packets;
 leg region cutting means, for cutting out leg regions;
 elasticated web cutting means, for cutting elasticated web; and
 fastening supply means for supply of fastening means.

The elasticated web supply means is arranged so as to provide an elasticated web having discontinuous elastic threads in which at least one first discontinuous elastic thread is sandwiched between the first faces of respective first and second webs; and at least one second discontinuous elastic thread is sandwiched between the first faces of respective third and second webs.

The absorbent packet supply means is arranged so as to place an absorbent packet so as to overlie at least a portion of the first web, second web and/or the third web, and to fix said absorbent packet to at least one of said first, second and third webs.

The leg region cutting means is arranged so as to cut out a region of the elasticated web defined substantially between discontinuous elastic threads of the first and third webs, so as to form leg openings.

The fastening supply means arranged so as to provide fastening means on said elasticated web.

The elasticated web cutting means is arranged so as to cut the elasticated web along cutting lines, said cutting lines extending substantially in the cross direction from the first edge to the second edge of the elasticated web, said cutting lines being located substantially at the point at which the discontinuous elastic threads are located furthest from the first edges of the first and third webs.

DEFINITIONS

The "machine-direction" should be understood to mean the principal direction of travel of the components in an automated process. The "cross-direction" should be understood to mean the direction perpendicular to the machine direction, in the plane of the components.

The term "absorbent article" refers to products that are placed against the skin of the wearer to absorb and contain body exudates, like urine, faeces and menstrual fluid. The disclosure mainly refers to disposable absorbent articles, which means articles that are not intended to be laundered or otherwise restored or reused as an absorbent article after use. The term includes diapers (both open diapers and pant diapers) and incontinence guards.

BRIEF DESCRIPTION OF THE DRAWINGS

Embodiments of the invention will now be more closely described with reference to the enclosed schematic figures, in which:

FIG. 3 is a simplified view of the first embodiment, with a different loop fastening means FIG. 3A is an expanded cross-sectional view along the line IIIA-IIIA in FIG. 3

FIG. 3B is an expanded cross-sectional view along the line IIIB-IIIB in FIG. 3

FIG. 4A is a cross-sectional view of an apparatus suitable for providing the elasticated web of the first embodiment.

FIG. 4B is an expanded cross-sectional view along lines A-A and B-B in FIG. 4A.

FIG. 11 shows an embodiment of a pant-type article

FIG. 11A is a cross-sectional view along line XIA-XIA of FIG. 11

FIG. 12 shows an embodiment of a pant-type article

FIG. 12A is a cross-sectional view along line XIIA-XIIA of FIG. 12

FIG. 13 shows an embodiment of a pant-type article

FIG. 13A is a cross-sectional view along line XIIIA-XIIIA of FIG. 13

FIG. 14 shows an embodiment of a pant-type article

FIG. 14A is a cross-sectional view along line XIVA-XIVA of FIG. 14

FIG. 15 shows an embodiment of a pant-type article

FIG. 15A is a cross-sectional view along line XVA-XVA of FIG. 15

FIG. 16 shows an embodiment of a pant-type article

FIG. 16A is a cross-sectional view along line XVIA-XVIA of FIG. 16

FIG. 17 shows an embodiment of a pant-type article

FIG. 17A is a cross-sectional view along line XVIIA-XVIIA of FIG. 17

FIG. 18 shows an embodiment of an open diaper

FIG. 18A is a cross-sectional view along line XVIIIA-XVIIIA of FIG. 18

FIG. 19 shows an embodiment of an open diaper

FIG. 19A is a cross-sectional view along line XIXA-XIXA of FIG. 18

FIG. 20 shows an embodiment of an open diaper

FIG. 20A is a cross-sectional view along line XXA-XXA of FIG. 20

DETAILED DESCRIPTION OF PREFERRED EMBODIMENTS

Figure 1:
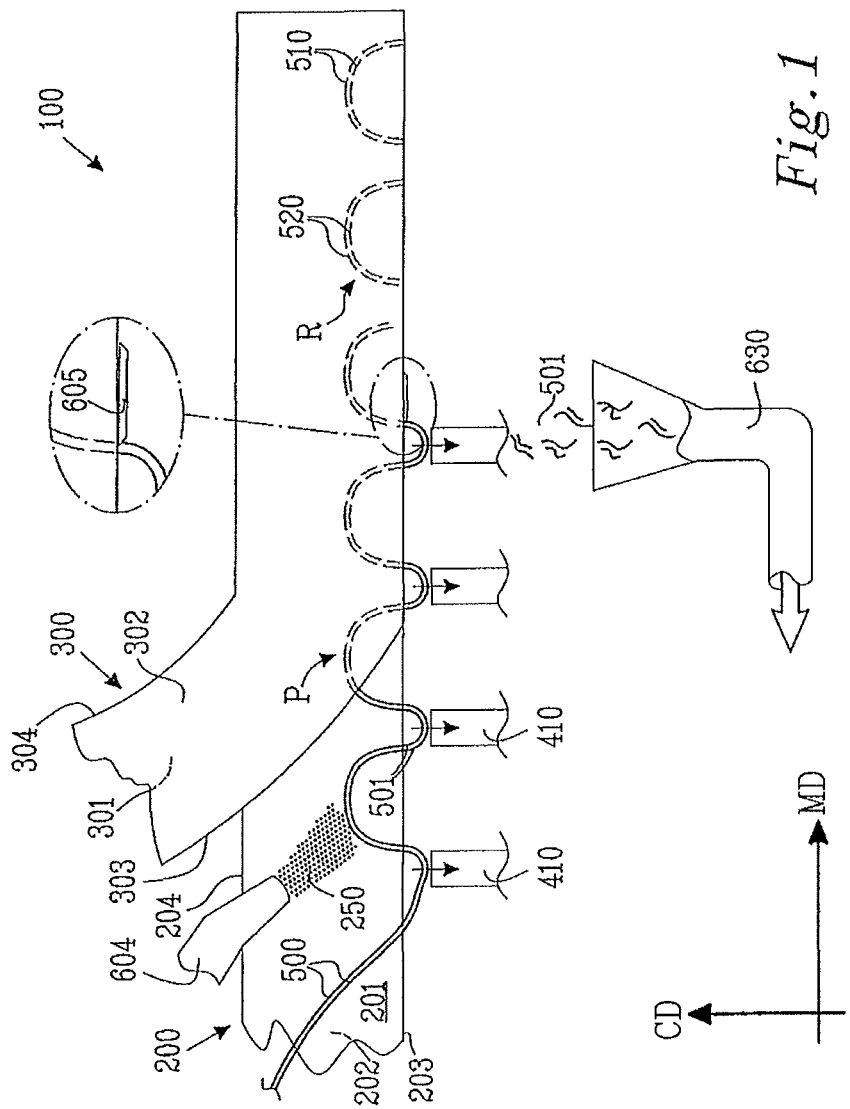
FIG. 1 is a simplified view of a first embodiment of a method for manufacturing an elasticated web.

A simplified view of one embodiment is shown in FIG. 1. The illustrated method allows an elasticated web 100 having discontinuous elastic threads 510 to be manufactured. The elasticated web 100 is essentially a laminate of first 200 and second 300 webs, with discontinuous elastic threads 510 sandwiched between said first 200 and second 300 webs.

In a first step, a first web 200 is provided. The first web 200 may include a nonwoven material (e.g. spunbond, meltblown, carded, hydroentangled, wetlaid etc). The fibres of the nonwoven material may be natural (e.g. rayon or cellulose fibres) or artificial (e.g. polymeric fibres such as polyolefin fibres, e.g. polyethylene or polypropylene fibres). The first web 200 may alternatively include a plastic film, e.g. a polyolefin film such as polyethylene or polypropylene. The first web 200 may even include a laminate of two or more nonwoven layers, or a laminate of one or more nonwoven layers with one or more plastic films. Suitably, the first web 200 has a basis weight of between 10-40 $g/m^2$. The first web 200 should suitably be air-permeable.

The first web 200 has a primary extension in the machine direction (MD), first 201 and second 202 faces and a first edge 203 and a second edge 204. The first and second edges 203, 204 extend in the machine direction (MD). First 203 and second 204 edges of the first web 200 are typically straight and parallel to one another. The first web 200 is transported essentially continuously in the machine direction from e.g. a roll. Typically, the first web 200 has an extension in the cross direction (CD) of between 10 and 25 cm for a baby diaper and 20-50 cm for an adult incontinence pant, particularly between 13-20 cm for a baby diaper and 30-43 cm for an adult incontinence pant.

A second web 300 is also provided. The second web 300 may include one or more nonwoven materials, plastic films, or laminates of two such materials, in the same way as described for the first web 200, above. The first 200 and second 300 webs may be the same, or may be different. In a similar way to the first web 200, the second web 300 also has a primary extension in the machine direction (MD), first 301 and second 302 faces and a first edge 303 and a second edge 304, said first and second edges 303, 304 extending in the machine direction (MD). First 303 and second 304 edges of the second web 300 are typically straight and parallel to one another. The second web 300 may have the same dimensions as the first web 200, as shown in FIG. 1. However, it may be possible that the second web 300 has an extension in the cross-direction (CD) which is greater than or less than that of the first web 200. Suitably, the second web 300 has a basis weight of between 10-40 $g/m^2$. The second web 300 should be air-permeable.

A first adhesive 250 is applied to at least a portion of the first face 201 of the first web 200. The first adhesive 250 may be sprayed on the first face 201 of the first web 200, as shown in FIG. 1, but other methods of application may also be used, e.g. slot-coating, multi-bead coating, extrusion or rolling. A particular method of applying adhesive is slot-coating. The first adhesive 250 is typically applied to the first web 200 in amounts between 5 and 30 gsm, particularly between 5 and 15 gsm.

Suitable adhesives for the first adhesive 250 may be e.g. H4281RF from Bostik, NW1002 from HB Fuller GmbH or Dispomelt 5482 from National S&C.

The first adhesive 250 may be applied to the entire first face 201 of the first web 200. However, in the interests of economy, in certain embodiments, the first adhesive 250 is only applied to a portion of the first face 201 of the first web 200. The first adhesive 250 may be applied to the first web 200 in a substantially uniform manner, but particularly, the first adhesive 250 is applied to the first web 200 in a pattern (P) which corresponds to the pattern (P) in which the elastic threads 500 are applied to the first web 200 (see below).

At least one elastic thread 500 is applied on at least the portion of said first face 201 of said first web 200 which includes said first adhesive 250. The elastic threads 500 will eventually form the leg elastics of a pant-type article 20, or an absorbent article 10 of the open-diaper type. Suitable elastic threads 500 include e.g. C17A from Plymouth SA (synthetic elastic, profile 0.2 mm×2 mm×6 ends to be split up in the process) or XA T-262P 1A216 from Invista (1100 dtex single thread on spool, circular profile). Although the term "thread" is used in the present specification, the term is to be interpreted as including narrow bands of elastic material (e.g. with a width of less than 1 cm). The elastic threads 500 are supplied in a continuous manner from e.g. a roll. It may be possible that only one elastic thread 500 is applied to the first web 200, although more than one, e.g. 2, 3 or even 4 elastic threads 500 may be applied. In the case a plurality of elastic threads 500 is used, all elastic threads 500 should be applied substantially in parallel.

The at least one thread 500 is applied in a pattern (P), as shown in FIG. 1. The pattern (P) corresponds to the form of the leg elastics of an absorbent article. The pattern (P) oscillates in the cross-direction (CD) and extends in the machine direction (MD) of the first web 200. The pattern (P) is aligned such that it extends over the first edge 203 of the first web 200, as shown in FIG. 1. Loops 501 are thus formed in said elastic thread 500 which project in the cross-direction (CD) from the first edge 203 of said first web 200. FIG. 1 shows a wavy pattern (P); however, the pattern (P) can take a variety of oscillating forms, and may include one or more straight (linear) sections, a zig-zag form, a sinusoidal form or variations on such patterns (P).

As the elastic threads 500 are applied to the first web 200, the loops 501 which project in the cross-direction (CD) from the first edge 203 of said first web 200 are secured in a loop retaining means 410 which is located adjacent the first edge 203 of said first web 200. Suitably, the loop retaining means 410 is spaced from the first edge 203, so as to allow the subsequent cutting step(s) to take place.

Loop retaining means 410 acts to secure the loops 501. It is important that loops 501 are secured, so that—when the leading edge of each loop 501 is cut in the following steps—the loop 501 does not simply retract completely, but instead, tension is maintained between the following edge of each loop and the loop retaining means 410.

The loop retaining means 410 can take various forms. FIG. 1 shows loop retaining means 410 in the form of a vacuum member. The loops 501 are essentially sucked onto the vacuum member and secured thereto by suction. After cutting the loops 501, the vacuum is stopped, and the loops 501 are released.

Figure 2:
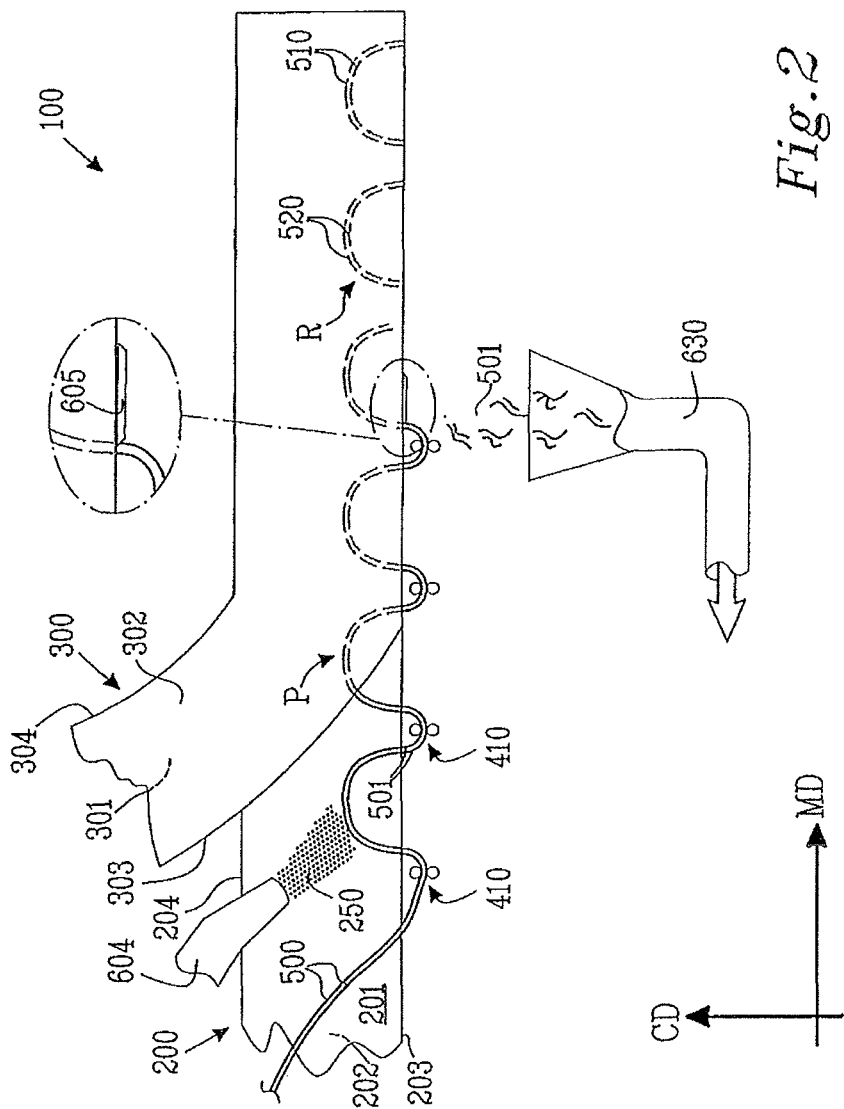
FIG. 2 is a simplified view of the first embodiment, with a different loop fastening means

FIG. 2 shows loop retaining means 410 in the form of two members, between which the loops 501 are secured. Loop retaining means 410 can equally include three or more members, between which the loops 501 are secured. The loops 501 are essentially pinched between the members of the loop retaining means 410, and then, after the loops 501 are cut, the members are separated, and the loops 501 are released.

In the embodiment illustrated in FIG. 3, the loop retaining means 410 includes at least one first 401 and at least one second 402 resilient belt which are located adjacent the first edge 203 of said first web 200. The loops 501 are therefore secured in a nip 400 between at least one first 401 and at least one second 402 resilient belt. The resilient belts 401, 402 may be made of rubber, or any other suitable resilient material. As shown in FIGS. 3, 3A and 4, one resilient belt 401 may have a cross-section such that it can engage with one or more recesses in the other resilient belt 402. To this effect, one resilient belt 401 may include one or more protrusions which can engage with one or more recesses in the other resilient belt 402, as illustrated. Alternatively, one resilient belt 401 may have a cross-section which is e.g. circular, semi-circular, oval, triangular or square and which can engage with one or more recesses in the other resilient belt 402. This profiled arrangement allows close contact between the belts 401, 402, and allows the loops 501 of the elastic thread 500 to be tightly secured between the resilient belts 401, 402. Alternatively, or additionally, to having recesses/protrusions, the belts 401, 402 may include high-friction surfaces which grip the loops 501 securely.

As shown in FIGS. 1-3, the first face 301 of the second web 300 is applied on the first face 201 of the first web 200. First 200 and second 300 webs are fixed together such that said at least one elastic thread 500 is partly sandwiched between the first faces 201, 301 of the respective first and second webs 200, 300. First and second webs 200, 300 may be fixed together by any suitable means, e.g. thermal welding, ultrasonic welding or adhesion. Adhesion can be the most preferred. Suitably, the first adhesive 250 which is used to secure the at least one elastic thread 500 to the first web 200 can also be used to secure the first 200 and second 300 webs together. Additional adhesive as required may be applied to the first face 301 of the second web 300 and/or the first face 201 of the first web 200. First 200 and second 300 webs are suitably fixed to one another across substantially their entire area of overlap.

The dimensions of the second web 300 are essentially independent of the dimensions of the first web 200. Similarly, the amount with which the second web 300 overlaps the first web 200 may be selected appropriately by the skilled person. Particularly, the dimensions of the second web 300, and the amount of overlap between first 200 and second webs 300, are such that the second web 300 overlaps the first web 200 in the entire region of the first web 200 in which elastic threads 500 are located.

Suitably (as shown in FIGS. 1-3) the first face 301 of the second web 300 is applied on the first face 201 of the first web 200 such that the first edge 303 of the second web 300 is substantially aligned with the first edge 203 of the first web 200. Additionally, but not necessarily, the first and second webs 200, 300 may have substantially the same width, such that both first 303 and second 304 edges of the second web 300 are substantially aligned with first 203 and second 204 edges of the first web 200, respectively. It may be possible that the second web 300 has an extension in the cross-direction (CD) which is greater than or less than that of the first web 200.

It may also be possible that the second web 300 is applied to the first web 200 so that the first edge 303 of the second web 300 is not substantially aligned with the first edge 203 of the first web 200; i.e. that the first edge 303 of the second web 300 is offset in the cross-direction (CD) from the first edge 203 of the first web 200. Thus, the second web 300 may extend in the cross-direction out from the first edge 203 of the first web 200, and may even completely overlap with the loops 501 of elastic thread 500. Depending on the extent to which the first edge 303 of the second web 300 is offset from the first edge 203 of the first web 200, it may be possible, or even necessary, that the second web 300 is also secured in the nip 400 between at least one first 401 and at least one second 402 resilient belts.

Suitably, and as shown in FIG. 4, the steps of:
applying at least one elastic thread 500 on at least the portion of the first face 201 of the first web 200 which includes said first adhesive 250
securing the loops 501 in a nip 400 between at least one first 401 and at least one second 402 resilient belt, and
applying the first face 301 of said second web 300 on the first face 201 of said first web 200 and fixing said first 200 and second 300 webs together;
may occur substantially simultaneously in a single nip 400.

While the elastic threads 500 are still held in the loop retaining means nip 410, (e.g. in a nip 400 between first 401 and second 402 resilient belts) the elastic threads 500 are cut by cutting means 605 substantially at each point at which the elastic thread 500 crosses the first edge 203 of the first web 200. The loops 501 therefore become detached from the first web 200. As shown in FIG. 3, the resilient belts 401, 402 are separated from one another, and loops 501 removed from the remainder of the elasticated web 100. Suitably, vacuum means 630 is used to remove the loops 501 from the process.

Cutting the elastic threads 500 may take place in an essentially continuous manner. If the first edge 303 of the second web 300 is substantially aligned with the first edge 203 of the first web 200, as described above, continuous cutting can be preferred, as only the loops 501 in the elastic threads 500 will be cut. Continuous cutting may also be used if the second web 300 extends further in the cross-direction than the first edge 203 of the first web 200; in this case, a strip of the second web 300 will also be cut from the elasticated web 100.

Intermittent cutting may also be used to cut the elastic threads 500. In this embodiment, cuts are only made substantially at each point at which the elastic thread 500 crosses the first edge 203 of the first web 200. If the second web 300 extends further in the cross-direction (CD) than the first edge 203 of the first web 200, intermittent cutting will allow the entire width of the second web 300 in the cross-direction (CD) to be maintained in the elasticated web 100. The second web 300 may therefore include small cuts at each point at which the elastic thread 500 crosses the first edge 203 of the first web 200.

After cutting, the elasticated web 100 having discontinuous elastic threads 510 is provided. This elasticated web 100 may be rolled up and stored, or used directly to produce pant-type articles 20 or absorbent articles 10 of the open-diaper type. In that loop retaining means 410 (such as resilient belts 401, 402) is used to retain the elastic threads 500 in the production of the elasticated web 100, undesired pieces of elastic are captured, controlled and safely disposed of during the process. In addition, the tension in the discontinuous elastic threads 510 can be controlled, and cutting of the elastic threads 500 can be performed accurately, as the elastic threads 500 are held in tension by the loop retaining means 410.

The disclosure therefore relates to an elasticated web 100 produced according to the methods described herein, and the elasticated web 100 per se. The elasticated web 100 is illustrated in FIGS. 1-3, and shown in cross-section in FIG. 3B. The elasticated web 100 has discontinuous elastic threads 510 and includes:
a first web 200, said first web 200 having a primary extension in the machine direction (MD), first 201 and second 202 faces and a first edge 203 and a second edge 204, said first and second edges 203, 204 extending in the machine direction (MD); and a second web 300, said second web 300 also having a primary extension in the machine direction (MD), first 301 and second 302 faces and a first edge 303 and a second edge 304, said first and second edges 303, 304 extending in the machine direction (MD).

A first adhesive 250 is arranged on at least a portion of the first face 201 of said first web 200. At least one discontinuous elastic thread 510 arranged on at least the portion of the first face 201 of the first web 200 which includes said first adhesive 250.

The first face 301 of said second web 300 overlies the first face 201 of said first web 200, to form a laminate. The first 200 and second webs 300 are fixed together such that the at least one discontinuous elastic thread 510 is sandwiched between the first faces 201, 301 of said respective first and second webs 200, 300.

The at least one discontinuous thread 510 is present between the first and second webs 200, 300 in a pattern (R), as per FIGS. 1-3. Pattern (R) corresponds to the portion of pattern (P), described above, which is located on the first web 200. The pattern (R) thus forms loops 520 which extend from the first edge 203 of the first web 200 and back to the first edge 203 of the first web 200; so that the discontinuous elastic threads 510 terminate at each point at which they meet the first edge 203 of said first web 200. The curves of the pattern (R) may be curved; however, the pattern (R) can take a variety of forms, and may include one or more straight (linear) sections or variations on such patterns (R). The loops 520 of the pattern (R) should have an axis of symmetry lying in the cross-direction (CD), in order for each absorbent article 10, or pant-type article 20 to have an axis of symmetry.

The method according to the present disclosure allows the elasticated web 100 to be formed, which is not possible with the methods of the prior art. In particular—in that the elastic threads 500 are secured by loop retaining means 410—elastic threads 500 are in tension, which allows accurate cutting of the elastic threads 500 to be carried out. In turn, this means that discontinuous elastic threads 510 can terminate at each point at which they meet the first edge 203 of said first web 200.

FIG. 3A is an expanded cross-sectional view of the nascent elasticated web 100 along the line IIIA-IIIA in FIG. 3, i.e. prior to cutting the elastic threads 500. It shows the first web 200, the second web 300 and the elastic threads 500 (which project in the cross-direction (CD) from the first edge 203 of said first web 200) secured between the first 401 and second 402 resilient belt. In addition, FIG. 3A shows the resilient belts 401, 402 having a particular profile which promotes a secure grip on the elastic threads.

FIG. 3B is an expanded cross-sectional view of the elasticated web 100 along the line IIIB-IIIB in FIG. 3; i.e. after cutting the elastic threads 500. It shows the first web 200, the second web 300 and the discontinuous elastic threads 510 laminated between first 200 and second 300 webs.

Figure 5:
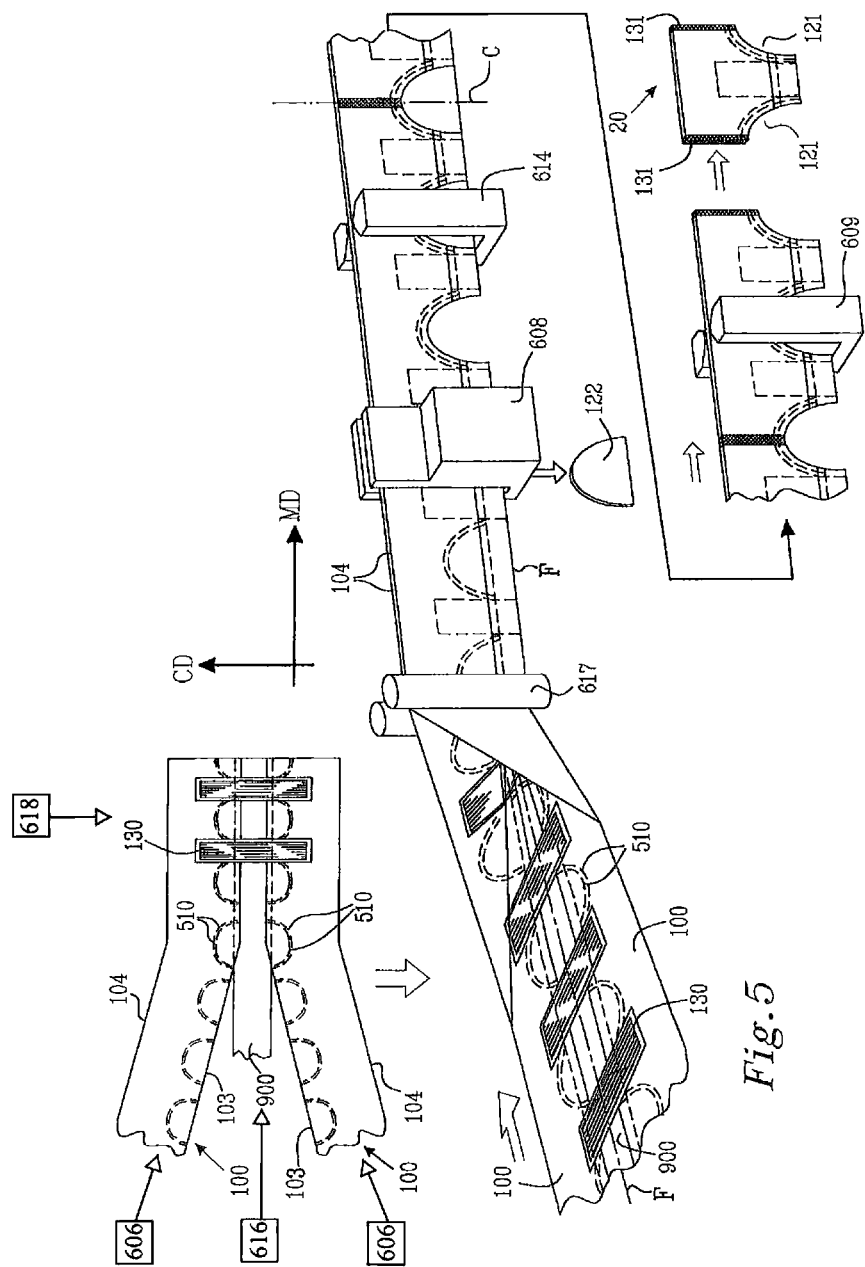
FIG. 5 shows how a pant-type article may be produced from two elasticated webs of FIG. 3.

The disclosure also provides a method for manufacturing pant-type articles 20, as illustrated in FIG. 5. Firstly, elasticated webs 100 having discontinuous elastic threads 510 are provided according to the method in FIGS. 1-3. The elasticated web 100 has first and second edges 103, 104 extending in the machine direction (MD), and also has discontinuous elastic threads 510. The discontinuous elastic threads 510 are sandwiched between the first faces 201, 301 of respective first and second webs 200, 300 and extend to the first edge 103 of said elasticated web 100.

First and second such elasticated webs 100 are arranged adjacent one another and in a spaced relationship such that the first edges 103 of each of said elasticated webs 100 are located closest to one another and aligned substantially parallel to one another. The first edge 103 of the elasticated web 100 is that edge which includes the first edge 203 of the first 200 and/or second 300 web. The first and second elasticated webs 100 are synchronised such that each discontinuous elastic thread 510 in the first elasticated web 100 is located opposite a corresponding discontinuous elastic thread 510 in the second elasticated web 100. This is shown in FIG. 5.

First and second elasticated webs 100 may be produced in parallel according to the embodiment of FIG. 1-3, particularly FIG. 3. In this case, the process illustrated in FIGS. 1-3 is carried out to produce first and second elasticated webs 100 in a side-by-side fashion immediately prior to manufacturing pant-type articles 20. Alternatively, first and second elasticated webs 100 may be produced independently, and then arranged adjacent one another prior to manufacturing pant-type articles 20.

The first and second elasticated webs 100 are bridged with a third component. Bridging may take place in a number of ways, depending on the nature of the pant-type article which is desired.

A first option is to join the first and second elasticated webs 100 by means of a fourth web 900. A fourth web 900 is thus placed so as to overlie the first edges 103 of the first and second elasticated webs 100, and is fixed to both first and second elasticated webs 100. Fixing of the fourth web 900 may be carried out using any known method, such as e.g. thermal welding, ultrasonic welding or adhesion. Adhesion can be the most preferred, and any suitable adhesive such as that used as the first adhesive 250 may be used. This option is used to manufacture pant-type articles 20 having a crotch layer 180, but which do not contain absorbent packets 130, which articles 20 are discussed further in relation to FIG. 11, below.

A second option is to join the first and second elasticated webs 100 by means of an absorbent packet 130. The absorbent packet 130 generally includes an absorbent core 133 covered by one or more cover layers 134.

The absorbent core 133 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. The thin absorbent bodies, which are common in for example baby diapers and incontinence guards, often include a compressed mixed or layered structure of cellulosic fluff pulp and superabsorbent. The size and absorbent capacity of the absorbent core may be varied to be suited for different uses such as for infants or for incontinent adults. The absorbent core 133 may include one or more layers which may be selected to improve the handling of bodily waste. Such layers are designed to receive a large amount of liquid in a short space of time and distribute it evenly across the absorbent core 133. They may include so-called transfer, distribution, surge or acquisition layers.

Cover layers 134 surround the absorbent core 133, and act to maintain the integrity and shape of the absorbent core 133, and to provide good attachment to the elasticated webs 100. Cover layers 134 may also provide the absorbent core 133 with appropriate liquid-handling properties, and are therefore suitably different on each face of the absorbent core 133. For example, the face of the absorbent core 133 which is to face the wearer may include a cover layer 134 which exhibits rapid liquid intake, while the cover layer 134 of the absorbent core 133 which is to face the wearer's garment may exhibit liquid-barrier properties.

Absorbent packets 130 are thus placed so as to overlie the first edges 103 of the first and second elasticated webs 100, and fixed to both first and second elasticated webs 100. The absorbent packet 130 may be applied in such a way that the side edges of the packet are located adjacent the ends of the discontinuous threads 510. Fixing of the absorbent packet may be carried out using any known method, such as e.g. thermal welding, ultrasonic welding or adhesion. Adhesion can be the most preferred, and any suitable adhesive such as that used as the first adhesive 250 may be used.

Depending on the design of the absorbent packet 130, and its purpose, the packet 130 can overlap first and second elasticated webs 100 to the same extent, or it may overlap one elasticated web 100 to a greater extent that the other. The absorbent packet 130 is fixed in a position located equidistant from two adjacent discontinuous elastic threads 510 in the transverse direction. Particularly, the absorbent packet 130 does not overlap with the discontinuous elastic threads 510, but it may do so.

This option is used to manufacture pant-type articles containing absorbent packets 130, which do not contain a crotch layer 180. Such articles are discussed further in relation to FIG. 12, below.

A third option is to join the first and second elasticated webs 100 by means of both a fourth web 900 and an absorbent packet 130. Fourth web 900 and absorbent packets 130 are placed so as to overlie the first edges 103 of the first and second elasticated webs 100, and at least one of said fourth web 900 and/or said absorbent packet 130 is fixed to both first and second elasticated webs 100, so as to bridge the first and second elasticated webs 100. Suitably, both the fourth web 900 and the absorbent packet 130 are fixed to both first and second elasticated webs 100. However, it is possible in certain embodiments that the absorbent packet is only fixed to the fourth web 900, or to one of the first and second elasticated webs 100. This third option is used to manufacture pant-type articles containing absorbent packets 130 and a crotch layer 180. Such articles are discussed further in relation to FIG. 13, below.

An optional—yet preferred—step is to cut a leg region 122 out of one or both elasticated webs 100 and—if present—said fourth web 900, as shown in FIG. 5. Indeed, if a fourth web is present, it is essential to cut a leg region out of at least this fourth web 900. Each leg region 122 is defined substantially by discontinuous elastic thread 510 so as to form leg openings 121. Cutting the leg region 122 is shown in FIG. 5 as occurring after fixing the absorbent packets 130; however, it may take place before absorbent packets 130 are fixed to the elasticated webs 100. Cutting the leg region 122 out may take place through mechanical means (e.g. blades or punches) or methods such as laser, water cutting jet, ultrasonic or thermal cutting, or combinations thereof. Use of a rotary die cutter (RDC) can be a preferred technique.

The next step in FIG. 5 is that the co-joined elasticated webs 100 are folded along a fold-line (F), so that second edges 104 of each elasticated web 100 become arranged substantially adjacent one another and substantially parallel, with the fourth web 900 located on the outside of the fold and/or the absorbent packet 130 located on the inside of the fold.

The first and second elasticated webs 100, in their folded configuration, are then joined to each other along lines (C), said lines (C) extending substantially in the cross direction (CD) from the second edges 104 of each elasticated web 100 to the fold-line (F). The lines (C) are located substantially at the point at which the at least one discontinuous elastic thread 510 is located furthest from the first edge 103 of each elasticated web 100. The join which is thus made will eventually form side-seams 131. Joining can take place by adhesion, thermal or ultrasonic welding or any common method known in the art.

Each elasticated web 100 and—if present—the fourth web 900 is then cut along lines (C) such that first and second elasticated webs 100 remain joined on either side of the cut. Cutting along lines (C) extending substantially in the cross direction (CD) separates the individual pant-type articles 20 from each other in the elasticated web 100. Pant-type articles 20 are thereby produced.

Additional material layers may be added to the pant-type articles 20 at any point during the above-described manufacturing process. For example, a topsheet including a nonwoven or nonwoven laminate may be added to the pant-type articles 20 on the side which is intended to face the wearer's skin. A liquid-impermeable backsheet may be added to the pant-type articles 20 on the side which is intended to face the wearer's garments.

The pant-type articles 20 of the disclosure may include additional components such as waist elastics 135, body elastics 137 and standing gathers. Suitable methods for applying such components will be known to the skilled person.

Figure 6:
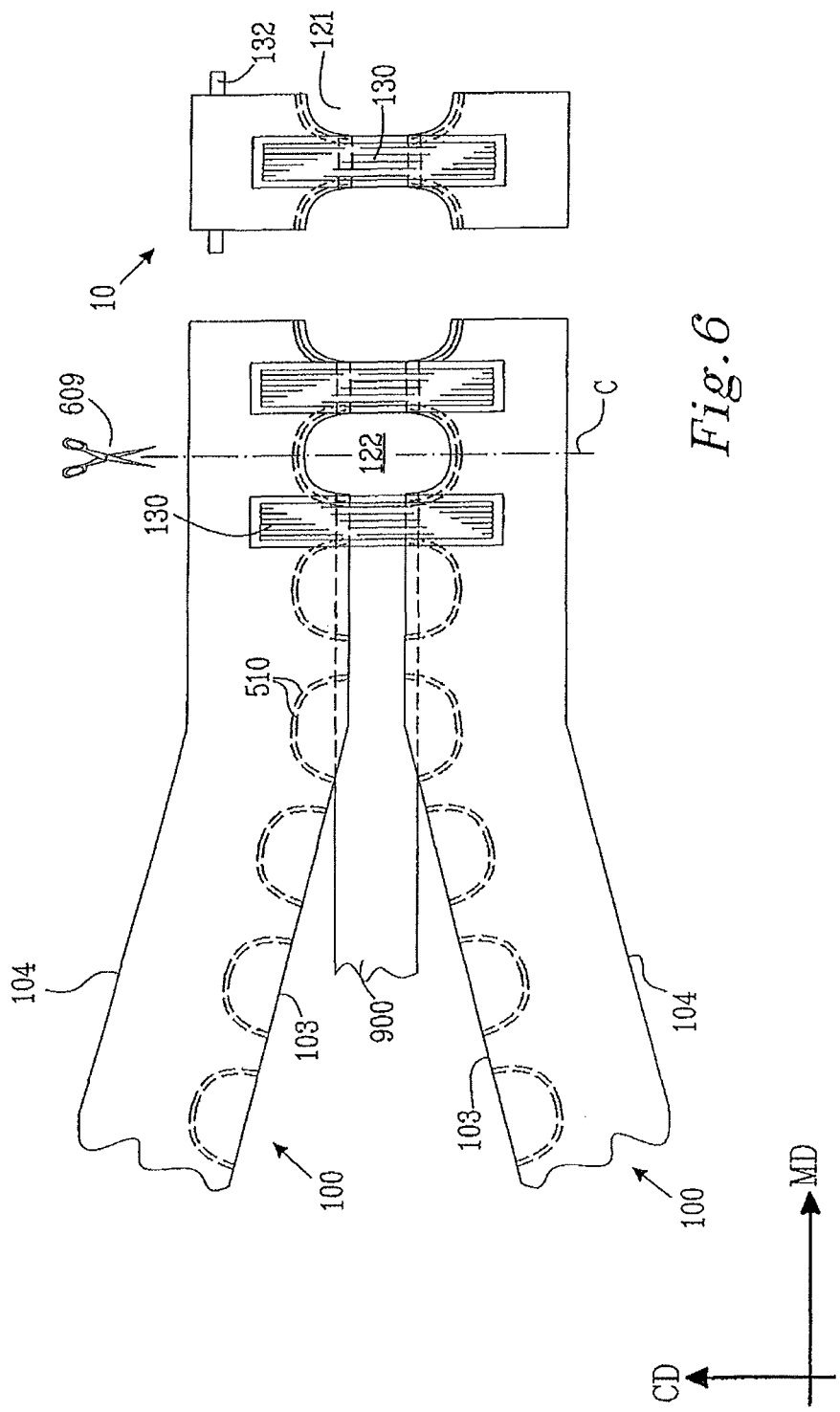
FIG. 6 shows how an open diaper may be produced from two elasticated webs of FIG. 3.

The present disclosure also relates to a method for manufacturing absorbent articles 10, in the form of open diapers, so-called "all-in-one" diapers. This method is illustrated in FIG. 6.

As above, for the pant-type article 20, the first step of the method for manufacturing absorbent articles 10 is providing an elasticated web 100, said elasticated web 100 having first and second edges 103, 104 extending in the machine direction (MD); said elasticated web 100 also having discontinuous elastic threads 510 in which discontinuous elastic threads 510 are sandwiched between the first faces 201, 301 of respective first and second webs 200, 300 and extend to the first edge 103 of said elasticated web 100.

First and second such elasticated webs 100 are arranged adjacent one another and in a spaced relationship such that first edges 103 of each of said elasticated webs 100 are located closest to one another and aligned substantially parallel to one another. The first and second elasticated webs 100 are synchronised such that each discontinuous elastic thread 510 in the first elasticated web 100 is located opposite a corresponding discontinuous elastic thread 510 in the second elasticated web 100. This is illustrated in FIG. 6.

First and second elasticated webs 100 may be produced in parallel according to the embodiment of FIGS. 1-3, particularly FIG. 3. In this case, the process illustrated in FIGS. 1-3 is carried out to produce first and second elasticated webs 100 in a side-by-side fashion immediately prior to manufacturing absorbent articles 10. Alternatively, first and second elasticated webs 100 may be produced independently, and then arranged adjacent one another prior to manufacturing absorbent articles 10.

An absorbent packet 130 is placed so as to overlie at least a portion of the first and/or second elasticated webs 100. The absorbent packet 130 may be fixed to both first and second elasticated webs 100, or only one of said elasticated webs 100. If no fourth web 900 is present, the absorbent packet 130 should be fixed to both first and second elasticated webs 100, so as to bridge them. Fixing of the absorbent packet may be carried out using any known method, such as e.g. thermal welding, ultrasonic welding or adhesion. Adhesion can be the most preferred, and any suitable adhesive such as that used as the first adhesive 250 may be used. The nature and form of the absorbent packet 130 is as described above.

If desired, a fourth web 900 is also placed so as to overlie the first edges 103 of the first and second elasticated webs 100. At least one of said fourth web 900 and/or said absorbent packet 130 is fixed to both first and second elasticated webs 100. Both fourth web 900 and absorbent packet 130 may be fixed to both first and second elasticated webs 100. It can be preferred that at least the fourth web 900 is fixed to both first and second elasticated webs 100. If a fourth web is present, absorbent articles 10 are produced which have a crotch layer 180, as shown in FIG. 18. Such articles are discussed further in relation to FIG. 18, below. If no fourth web 900 is present, absorbent articles 10 are produced which do not have a crotch layer 180, as shown in FIG. 19. Such articles are discussed further in relation to FIG. 19, below.

Leg regions 122 of said fourth web 900, and optionally said first and/or second elasticated webs 100, are then cut out. Each leg region 122 is defined substantially within said elasticated webs 100 by discontinuous elastic threads 510.

The co-joined elasticated webs 100 and—if present—the fourth web 900 are then cut along lines (C), said lines (C) extending substantially in the cross direction (CD) from the second edge 104 of one elasticated web 100 to the second edge 104 of the other elasticated web 100. As before, for the pant-type article, lines (C) are located substantially at the point at which the at least one discontinuous elastic thread 510 is located furthest from the first edge 103 of each elasticated web 100.

Fastening means 132 are then provided on at least one of said first and second elasticated webs 100. The fastening means 132 are suitably located on the outside face of the absorbent article 10. Fastening means 132 may include a hook-and-loop fastening means or adhesive fastening means. One component of the fastening means 132 (e.g. a hook component) may be provided on the first elasticated web 100, while the corresponding component (e.g. a loop component) may be provided on the second elasticated web 100. Alternatively, it may be possible to attach the fastening means 132 to the elasticated web 100 itself (e.g. a hook fastening means may attach to a nonwoven material which constitutes the elasticated web 100, or an adhesive fastening means may attach to a plastic film which constitutes the elasticated web 100). In this embodiment, it may be sufficient that fastening means 132 is only provided on one elasticated web 100. The nature of the fastening means 132, their location in the diaper and suitable methods for their provision are known to the skilled person.

The absorbent articles 10 of the disclosure may include additional components such as waist elastics 135, body elastics 137 and standing gathers. Suitable methods for applying such components will be known to the skilled person.

The disclosure also provides an apparatus 600 for manufacturing an elasticated web 100 having discontinuous elastic threads 510 according to the embodiment illustrated in FIG. 1-3.

The apparatus 600 is illustrated schematically in FIG. 4, and includes:
- first web supply means 601, for supplying said first web 200;
- second web supply means 602, for supplying said second web 300;
- elastic thread supply means 603 for supplying said at least one elastic thread 500;
- adhesive supply means 604 for supplying said first adhesive 250; and
- elastic cutting means 605 for cutting said at least one elastic thread 500.

The first web supply means 601 typically includes a supply of first web 200 (e.g. a roll) and means adapted for feeding said first web 200 in the machine direction. The first web supply means 601 may include any suitable combination of cylinders, belts, rods tensioning means or the like. Similarly, the second web supply means 602 typically includes a supply of second web 300 (e.g. a roll) and means adapted for feeding said second web 300 in the machine direction. The second web supply means 602 may include any suitable combination of cylinders, belts, rods, tensioning means or the like.

The adhesive supply means 604 is arranged so as to apply a first adhesive 250 to at least a portion of the first face 201 of said first web 200. The adhesive supply means 604 typically includes a slot coater, roller, sprayer or similar. The adhesive supply means 604 can reciprocate in the cross-direction, so as to be able to apply the first adhesive 250 to the first face 201 of the first web 200 in a pattern (P). It can also be divided into several crosswise sections so as to be able to apply adhesive in a pattern.

The elastic thread supply means 603 is arranged so as to apply at least one elastic thread 500 on at least the portion of the first face 201 of the first web 200 which includes said first adhesive 250. Guide fingers are suitable elastic thread supply means, and include elongated members which can reciprocate in the cross-direction.

The elastic thread supply means 603 applies the at least one thread 500 in a pattern (P). The pattern (P) oscillates in the cross-direction (CD) and extends in the machine direction (MD). The pattern (P) extends over the first edge 203 of the first web 200 to form loops 501 in the elastic threads 500 which project in the cross-direction (CD) from said first edge 203 of said first web 200, as per FIGS. 1-3.

The second web supply means 602 is arranged so as to apply the first face 301 of the second web 300 on the first face 201 of said first web 200, and fix said first 200 and second webs 300 together such that said at least one elastic thread 500 is partly sandwiched between the first faces 201, 301 of respective first and second webs 200, 300 (see FIG. 4).

The elastic cutting means 605 is illustrated in FIG. 4 as a rotating circular blade, although other types of cutting means may be suitable (e.g. a fixed blade, laser cutting, ultrasonic cutting). As described above, cutting may be continuous, or intermittent. Continuous cutting may be performed by a rotating circular blade (as per FIG. 4), or a fixed blade. Intermittent cutting may be carried out by a rotating circular blade, or a fixed blade, which is moved intermittently towards and away from the elastic threads 500. Alternatively, intermittent cutting may be carried out by a rotating blade having raised cutting portions and recessed non-cutting portions. For intermittent cutting processes, it is important that the cutting action is synchronised, so that cutting only takes place substantially at the points at which elastic threads 500 are present.

The elastic cutting means 605 is arranged so as to cut all the elastic threads 500 substantially at the point at which each elastic thread 500 crosses the first edge 203 of said first web 200. In this way, the loops 501 become detached from the first web 200.

The apparatus 600 additionally includes loop retaining means 410 located adjacent the first edge 203 of said first web 200 and which is adapted so as to secure the loops 501 in said loop retaining means 410. Suitably, the loop retaining means 410 is spaced from the first edge 203, so as to allow the subsequent cutting step(s) to take place. The loop retaining means 410 may be any loop retaining means described above in relation to FIGS. 1-3.

In the embodiment shown in FIG. 4, loop retaining means 410 includes at least one first 401 and at least one second 402 resilient belt which are located adjacent (i.e. outside) the first edge 203 of said first web 200. Combinations of various numbers of resilient belts 401, 402 may be used. The resilient belts 401, 402 may be made of rubber, or any other suitable resilient material. Suitable belts having the profile shown for the second belt 402 in FIG. 4, can be obtained from Abatron AB, Bromma, Sweden with the tradename Correx, Beige or Polythan Grün. Suitable belts having a circular profile can be obtained from Habasit AB, Hindås, Sweden, under the tradename Polycord R8. Resilient belts 401, 402 are typically located a distance of between 1 and 10 cm from the first edge 203 of the first web 200.

The resilient belts 401, 402 are adapted so as to secure the loops 501 in a nip 400 between said at least one first 401 and said at least one second 402 resilient belt. This may occur in that the loops 501 are secured between substantially flat faces of resilient belts 401, 402 and held in place by friction. However, as shown in FIGS. 3 and 4, the resilient belts 401, 402 may be profiled such that one resilient belt engages with one or more recesses in the other resilient belt. This profiled arrangement allows close contact between the belts 401, 402, and allows the loops 501 of the elastic thread 500 to be tightly secured between the resilient belts 401, 402. Although a simple profiled arrangement is shown in FIGS. 3 and 4, consisting of one protrusion on one resilient belt which engages with one recess in the other resilient belt, variations in the profile of each resilient belt may be made by the skilled person (e.g. two protrusions on one belt which engage with two recesses in the other belt, or a belt which has a cross-section (e.g. circular, semi-circular, triangular etc.), allowing it to engage with a recess in the other resilient belt). Alternatively, or additionally, to having recesses/protrusions, the belts 401, 402 may include high-friction surfaces which grip the loops 501 securely.

As shown in FIG. 4, the first web 200 and second web 300 may be fixed together in a single nip 400. The nip 400 is formed between two cylinders of the web supply means 601, 602. First web 200, second web 300, elastic threads 500 and resilient belts 401, 402 are brought together in this nip 400, thereby fixing these components together in a convenient and effective manner.

As is also illustrated in FIG. 4, first web supply means 601, second web supply means 602, elastic thread supply means 603 for supplying at least one elastic thread 500, adhesive supply means 604, cutting means 605 and at least one first 401 and at least one second 402 resilient belts are suitably arranged peripherally about a single central cylinder 620. However, other arrangements of these components are possible (e.g. linear).

The apparatus 600 described above may include additional components, making it suitable for manufacturing pant-type articles 20. The apparatus for manufacturing the pant-type articles 20 is illustrated schematically in FIG. 5. In this case, the apparatus 600 additionally includes;
  a. elasticated web supply means 606; for supply of first and second elasticated web 100
  b. fourth web supply means 616, for supply of fourth web 900 and/or absorbent packet supply means 618, for supply of absorbent packets 130
  c. leg region cutting means 608, for cutting out leg regions 122
  d. folding means 617 for folding the co-joined elasticated webs 100
  e. joining means 614 for joining the first and second elasticated webs 100
  f. elasticated web cutting means 609, for cutting elasticated webs 100 and—if present—the fourth web 900

The elasticated web supply means 606 is arranged so as to provide first and second elasticated webs 100 adjacent one another and in a spaced relationship such that the first edges 103 of each of said elasticated webs 100 are located closest to one another and aligned substantially parallel to one another. The elasticated web supply means 606 typically includes a supply of first and second elasticated webs 100 (e.g. rolls) and means adapted for feeding said webs 100 in a machine direction. The elasticated web supply means 606 may include any suitable combination of cylinders, belts, rods, web tensioners or the like. The first and second elasticated webs 100 are synchronised such that each discontinuous elastic thread 510 in the first elasticated web 100 is located opposite a corresponding discontinuous elastic thread 510 in the second elasticated web 100.

First and second elasticated webs 100 may be produced in parallel. In this case, the process illustrated in FIGS. 1-3 is carried out to produce first and second elasticated webs 100 in a side-by-side fashion immediately prior to manufacturing pant-type articles 20. Alternatively, first and second elasticated webs 100 may be produced independently, and then arranged adjacent one another prior to manufacturing pant-type articles 20. First and second elasticated webs 100 need not be identical—they may differ in their width in the cross-direction (CD) or in their arrangement of the discontinuous elastic threads 510.

If the pant-type article 20 is to include a crotch layer 180, the apparatus 600 includes a fourth web supply means 616. The fourth web supply means 616 is arranged so as to place a fourth web 900 so as to overlie the first edges 103 of the first and second elasticated webs 100, and to fix said fourth web 900 to both first and second elasticated webs 100. The fourth web supply means 616 typically includes a supply of fourth web 900 (e.g. a roll of this web) and means adapted for feeding said web 900 in a machine direction. The fourth web supply means 616 may include any suitable combination of cylinders, belts, rods, web tensioners or the like.

If the pant-type article 20 is to include an absorbent packet 130, the apparatus 600 includes absorbent packet supply means 618. The absorbent packet supply means 618 is arranged so as to place an absorbent packet 130 so as to overlie the first edges 103 of the first and second elasticated webs 100, and to fix said absorbent packet 130 to at least one of the first or second elasticated webs 100. In this way, at least one of the fourth web 900 and/or the absorbent packet 130 is fixed to both first and second elasticated webs 100, so as to bridge them. The absorbent packet supply means 618 typically includes a supply of absorbent packets 130 (e.g. a stack or roll) any suitable combination of cylinders, belts, rods or the like arranged so as to feed the absorbent packets 130 onto the first and second elasticated webs 100.

The absorbent packet 130 is suitably fixed to both first and second elasticated webs 100, although—if a fourth web 900 is present to bridge the elasticated webs 100—it may only be fixed to one of the elasticated webs 100, or only the fourth web 900. Fixing of the absorbent packet may be carried out using any known method, such as e.g. thermal welding, ultrasonic welding or adhesion. Adhesion can be the most preferred, and any suitable adhesive such as that used as the first adhesive 250 may be used. The absorbent packet supply means 618 therefore includes means for fixing the absorbent packets 130 to the elasticated webs 100.

The leg region cutting means 608 shown in FIG. 5 is arranged so as to cut out a leg region 122 of one or both elasticated webs 100 and—if present—said fourth web 900. Each leg region 122 is defined substantially by discontinuous elastic threads 510 in each of the elasticated webs 100, so as to form leg openings 121. Leg region cutting means 608 may include mechanical means (e.g. blades or punches) or other cutting means such as lasers, ultrasonic or thermal cutting means, rotary die cutters or combinations thereof. Leg region cutting means 608 may be arranged before or after absorbent packet supply means 618 in the apparatus 600. Equally, leg region cutting means 608 may be arranged before or after folding means 617.

The folding means 617 shown in FIG. 5 is arranged so as to fold the co-joined elasticated webs 100 along a fold-line (F), so that second edges 104 of each elasticated web 100 become arranged substantially adjacent one another and substantially parallel. The absorbent packet 130 is located on the inside of the fold. Folding means 617 may include any suitable combination of reciprocating or rotating members (e.g. arms or drums) webguides (e.g. metal sheets or rods), belts or the like.

The joining means 614 shown in FIG. 5 is arranged so as to join the first and second elasticated webs 100 to each other along lines (C). The lines (C) extend substantially in the cross direction (CD) from the second edges 104 of each elasticated web 100 to the fold-line (F), and are located substantially at the point at which the at least one discontinuous elastic thread 510 is located furthest from the first edge 103 of each elasticated web 100. Joining along lines (C) forms side-seams 131 in the nascent pant-type article 20. Joining can take place by adhesion, thermal or ultrasonic welding or any common method known in the art.

An elasticated web cutting means 609 is arranged in FIG. 5 so as to cut each elasticated web 100 and—if present—the fourth web 900, along lines (C) such that first and second elasticated webs 100 remain joined on either side of the cut. If the line (C) crosses the fourth web 900, the fourth web 900 may also be cut. Individual pant-type articles 20 are thus produced.

The pant-type articles 20 of the disclosure may include additional components such as waist elastics 135, body elastics 137 and standing gathers. Suitable methods for applying such components will be known to the skilled person.

In order to manufacture absorbent articles 10 in the form of open diapers, as illustrated in FIG. 6, the apparatus 600 includes;
a. elasticated web supply means 606; for supply of first and second elasticated web 100
b. absorbent packet supply means 618, for supply of absorbent packets 130
c. optionally, fourth web supply means 616, for supply of fourth web 900
d. leg region cutting means 608, for cutting out leg regions 122
e. elasticated web cutting means 609, for cutting elasticated webs 100, and—if present—the fourth web 900 and
f. fastening supply means 615, for supply of fastening means 132.

As before, the elasticated web supply means 606 is arranged so as to provide first and second elasticated webs 100 adjacent one another and in a spaced relationship such that the first edges 103 of each of said elasticated webs 100 are located closest to one another and aligned substantially parallel to one another. The first and second elasticated webs 100 are synchronised such that each discontinuous elastic thread 510 in the first elasticated web 100 is located opposite a corresponding discontinuous elastic thread 510 in the second elasticated web 100.

The absorbent packet supply means 618 is arranged so as to place an absorbent packet 130 so as to overlie at least a portion of the first and second elasticated webs 100. The absorbent packet supply means 618 is also adapted to fix the absorbent packet 130 to at least one of said first and second elasticated webs 100, or to the fourth web 900 if present.

If the absorbent article 10 is to include a crotch layer 180, the apparatus 600 includes a fourth web supply means 616. The fourth web supply means 616 is arranged so as to place a fourth web 900 so as to overlie the first edges 103 of the first and second elasticated webs 100, At least one of said fourth web 900 and/or said absorbent packet 130 are fixed to both first and second elasticated webs 100, so as to bridge the first and second elasticated webs 100.

The leg region cutting means 608 is arranged so as to cut out a leg region 122 of one or both elasticated webs 100 and—if present—said fourth web 900. Each leg region 122 is defined substantially by discontinuous elastic threads 510 in each of the elasticated webs 100, so as to form leg openings 121.

An elasticated web cutting means 609 is arranged so as to cut the co-joined elasticated webs 100 and—if present—the fourth web 900 along lines (C). The lines (C) extend substantially in the cross direction CD from the second edge 104 of one elasticated web 100 to the second edge 104 of the other elasticated web 100, and are located substantially at the point at which the at least one discontinuous elastic thread 510 is located furthest from the first edge 103 of each elasticated web 100.

Fastening supply means 615 is arranged so as to provide fastening means 132 on at least one of said first and second elasticated webs 100. Fastening supply means 615 includes a supply of fastening means 132 (e.g. a roll or stack) and means for feeding them to the nascent absorbent article 10 (e.g. nips, cylinders or belts) and means for joining the fastening means 615 to the article 10. Fastening means 132 may be joined to the absorbent article 10 by means of welding or gluing. Fastening means 132 are discussed in more detail above.

The absorbent articles 10 may include additional components such as waist elastics 135, body elastics 137 and standing gathers. Suitable methods for applying such components will be known to the skilled person.

Figure 7:
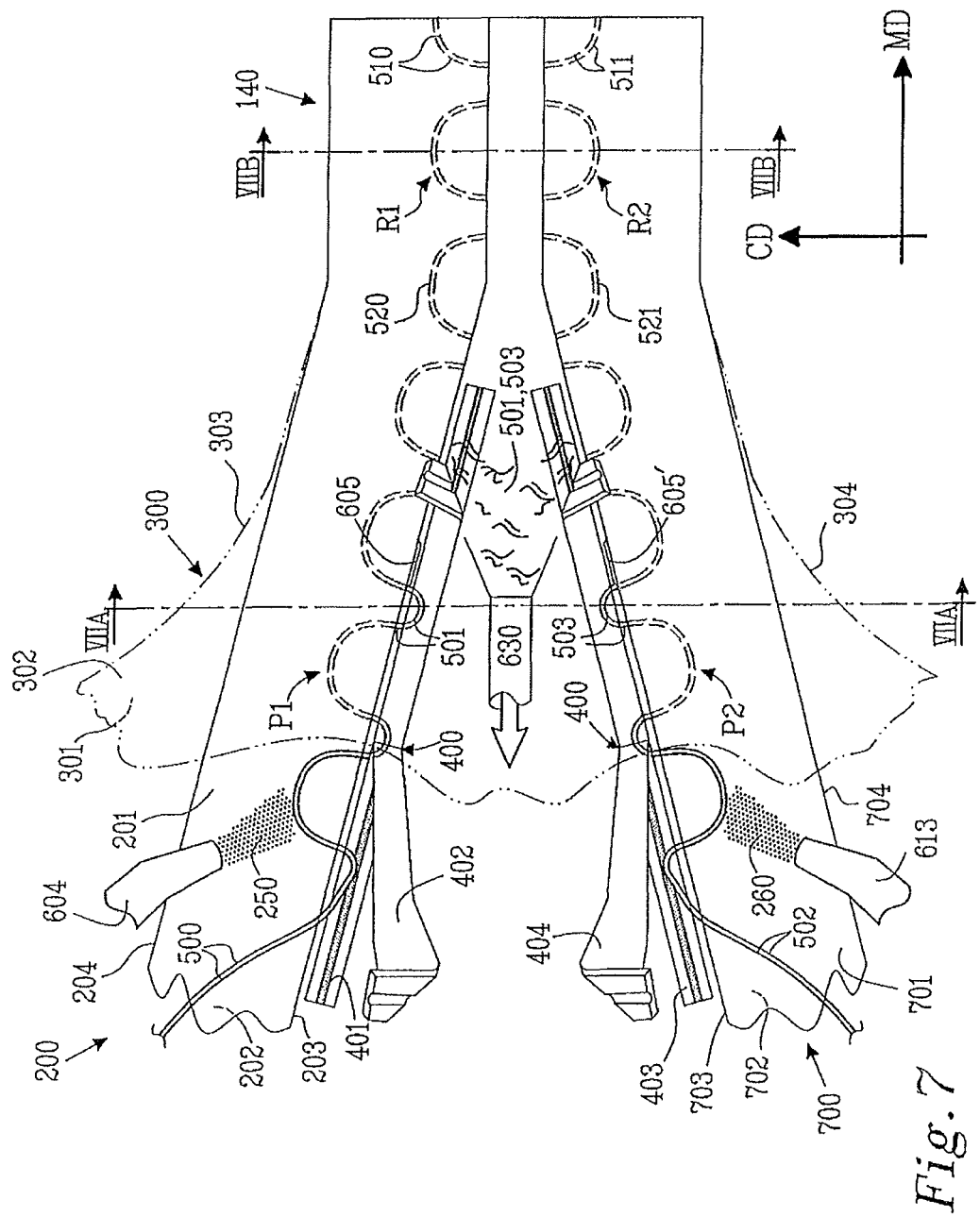
FIG. 7 is a simplified view of a second embodiment of a method for manufacturing an elasticated web.

In a second embodiment, illustrated in FIG. 7, the present disclosure provides a method for manufacturing an elasticated web 140 having discontinuous elastic threads 510, 511. In this second embodiment, the elasticated web 140 includes a laminate of first 200 and second 300 webs, with discontinuous elastic threads 510 sandwiched between said first 200 and second 300 webs, as per the first embodiment. On a different portion of the second web 300, a third web 700 is laminated, with discontinuous elastic threads 511 sandwiched between said third 700 and second 300 webs.

A first web 200 is provided, said first web 200 having a primary extension in the machine direction (MD), first 201 and second 202 faces and a first edge 203 and a second edge 204, said first and second edges 203, 204 extending in the machine direction (MD). A second web 300 is also provided, said second web 300 also having a primary extension in the machine direction (MD), first 301 and second 302 faces and a first edge 303 and a second edge 304, said first and second edges 303, 304 extending in the machine direction (MD).

A third web 700 is also provided said third web 700 having a primary extension in the machine direction (MD), first 701 and second 702 faces and a first edge 703 and a second edge 704, said first and second edges 703, 704 extending in the machine direction (MD). The second web 300 typically (but not necessarily) has an extension in the cross-direction (CD) which is equal to or greater than the combined extension of the first 200 and third 700 webs in the cross-direction (CD). FIG. 7 shows that the second web 300 has an extension in the cross-direction (CD) which is substantially equal to the combined extension of the first 200 and third 700 webs in the cross-direction (CD), plus the spacing between said first 200 and third webs 700 (i.e. the "crotch gap").

The material of the first 200 and third 700 webs may be selected from any material given for the first web 200, above. Similarly, the material of the second web 300 may be selected from any material given for the second web 300, above. It may be possible that the first 200 and third 700 webs originate from the same web which has been split into first 200 and third 700 webs.

The third web 700 is arranged to lie adjacent and substantially parallel with said first web 200, in a spaced arrangement with the first faces 201, 701 of said webs 200, 700 facing the same direction, such that the first edges 203, 703 of respective first 200 and third 700 webs are adjacent. This can be achieved by arranging first 200 and third webs 700 in parallel prior to applying adhesive and/or elastic threads. In effect, first 200 and third 700 webs may be processed in parallel through the same apparatus. First 200 and third 700 webs may even originate from the same single web (not shown), which is split in the machine direction to provide parallel first and third webs 200, 700, Alternatively, first 200 and third 700 webs may be processed separately up to this point, and aligned in the appropriate manner just prior to the second web 300 being applied in the following steps.

Figure 8A:
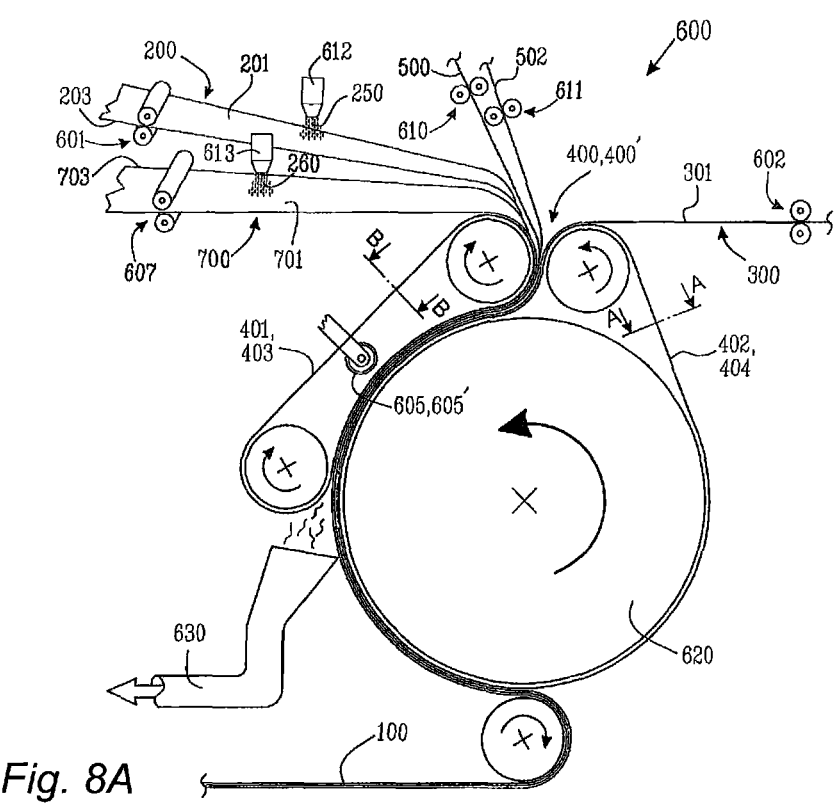
FIG. 8A is a cross-sectional view of an apparatus suitable for providing the elasticated web of the second embodiment.
Figure 8B:
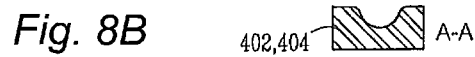
FIG. 8B is an expanded cross-sectional view along lines A-A and B-B in FIG. 8A.

In that first 200 and third 700 webs are arranged to lie adjacent and substantially parallel, they do not overlap when fixed to the second web 300. In effect, the second web 300 bridges the space between the first 200 and third 700 webs in the cross-direction (CD), thereby creating the elasticated web 140. The second web 300 may therefore be secured in the nip 400 between first 401, second 402, third 403 and fourth 404 resilient belts (see. FIG. 8).

In a similar way to the first embodiment, a first adhesive 250 is applied to at least a portion of the first face 201 of said first web 200. Alternatively, the first adhesive 250 is applied to at least a portion of the first face 301 of the second web 300.

Likewise, a second adhesive 260 is applied to at least a portion of the first face 701 of said third web 700. Alternatively, the second adhesive 260 is applied to at least a portion of the first face 301 of the second web 300. Should first and second adhesives 250, 260 both be applied to the second web 300, they should suitably be applied in different areas thereof, in a non-overlapping manner. The first and second adhesive 250, 260 are particularly applied to the second web 300 adjacent to one another in the cross-direction CD. First 250 and second 260 adhesives may be selected from any of the adhesives given for the first adhesive 250, above, and may include the same adhesive. Application means for said adhesives 250, 260 may also be selected from any means described above.

At least one first elastic thread 500 is applied on at least the portion of said first face 201 of said first web 200 or on at least the portion of said first face 301 of said second web 300 which includes said first adhesive 250. The nature and features of the first elastic thread 500 correspond to those of the elastic thread 500 given above in relation to the first embodiment. It may be possible in certain embodiments that only one elastic thread 500 is applied to the first web 200, although more than one, e.g. 2, 3 or even 4 elastic threads 500 may be applied. In the case a plurality of elastic threads 500 is used, all elastic threads 500 should be applied substantially in parallel. The at least one first thread 500 is applied in a first pattern (P1), said first pattern (P1) oscillating in the cross-direction (CD) and extending in the machine direction (MD)

In the same way as for the first web 200, at least one second elastic thread 502 is applied on at least the portion of said first face 701 of said third web 700 or on at least the portion of said first face 301 of said second web 300 which includes said second adhesive 260. The second elastic thread 502 may even be applied to the second web 300 before the nip (or in the nip). The at least one second elastic thread 502 is applied in a second pattern (P2), said second pattern (P2) oscillating in the cross-direction (CD) and extending in the machine direction (MD).

A portion of the first face 301 of the second web 300 is applied on the first face 201 of the first web 200, and the first 200 and second webs 300 are fixed together such that the at least one first elastic thread 500 is partly sandwiched between the first faces 201, 301 of respective first and second webs 200, 300, such that the first pattern (P1) extends over the first edge 203 of the first web 200 to form first loops 501 in said first elastic thread 500 which project in the cross-direction (CD) from said first edge 203 of said first web 200, see FIG. 7. FIG. 7 shows a wavy pattern (P1); however, the first pattern (P1) can take a variety of oscillating forms, and may include one or more straight (linear) sections, a zig-zag form, a sinusoidal form or variations on such patterns.

Similarly a portion of the first face 301 of the second web 300 is applied on the first face 701 of the third web 700, and the third 700 and second webs 300 are fixed together such that the at least one second elastic thread 502 is partly sandwiched between the first faces 301, 701 of respective second and third webs 300, 700 such that the second pattern (P2) extends over the first edge 703 of the third web 700 to form second loops 503 in said second elastic thread 502 which project in the cross-direction (CD) from said first edge 703 of said third web 700, see FIG. 7. FIG. 7 shows an essentially a wavy pattern (P2); however, the second pattern (P2) can take a variety of oscillating forms, and may include one or more straight (linear) sections, a zig-zag form, a sinusoidal form or variations on such patterns. The second pattern (P1) may take the same form as the first pattern (P1); however, it can be preferred that the second pattern (P2) is different to the first pattern (P1).

The first and second patterns (P1, P2) which the elastic threads 500, 502 make on the first 200 and third 700 webs are synchronised as shown in FIG. 7. Synchronisation occurs such that the point in the machine direction (MD) at which the first elastic threads 500 are located furthest from the first edge 203 of the first web 200 corresponds substantially to the point in the machine direction (MD) at which the second elastic threads 502 are located furthest from the first edge 703 of the third web 700. In other words, the first and second patterns P1, P2 have the same repeat frequency and meet and diverge repeatedly in the machine direction.

The first loops 501 of said first elastic threads 500 are secured in first loop retaining means 410 located adjacent the first edge 203 of said first web 200. First loop retaining means 410 can take any form as discussed above in relation to FIGS. 1-3. However, in FIG. 7, first loop retaining means 410 includes at least one first 401 and at least one second 402 resilient belt which are located adjacent the first edge 203 of said first web 200. The nature and features of the first 401 and second 402 resilient belts correspond to those given above for the first embodiment.

In a similar way to the first loops 501, the second loops 503 are secured in second loop retaining means 411 located adjacent the first edge 203 of said first web 200. Again, and independently of the first loop retaining means 410, second loop retaining means 411 can take any form as discussed above in relation to FIGS. 1-3. However, in FIG. 7, second loop retaining means 411 takes the form of at least one third 403 and at least one fourth 404 resilient belt which are located adjacent the first edge 703 of said third web 700. The nature and features of the third 403 and fourth 404 resilient belts correspond to those given above for the first embodiment. It is even possible that a single wide resilient belt includes the third resilient belt 403 and the first resilient belt 401, while a single wide resilient belt includes the fourth resilient belt 404 and the second resilient belt 402. In other words, a pair of wide resilient belts are used instead of four separate resilient belts, to capture all loops 501, 503. In this case, it is suitable that the wide resilient belts include have profiled arrangements at their cross-directional edges.

All the first elastic threads 500 are cut substantially at the point at which each first elastic thread 500 crosses the first edge 203 of said first web 200 such that the loops 501 become detached from the first web 200. Similarly, all the second elastic threads 502 are cut substantially at the point at which each second elastic thread 502 crosses the first edge 703 of said third web 700 such that the loops 503 become detached from the third web 700. Cutting of first 500 or second 502 elastic threads should be intermittent, so as not to completely remove the second web 300 from the nascent elasticated web 140. Details of the intermittent cutting step given above for the first embodiment are also relevant for this embodiment. An elasticated web 140 having discontinuous elastic threads 510, 511 is thus provided.

Similarly to the method of the first embodiment, the steps of:
- a. applying a first adhesive 250 to at least a portion of the first face 201 of said first web 200 or to at least a portion of the first face 301 of the second web 300;
- b. applying a second adhesive 260 to at least a portion of the first face 701 of said third web 700 or to at least a portion of the first face 301 of the second web 300;
- c. applying at least one first elastic thread 500 on at least the portion of said first face 201 of said first web 200 or on at least the portion of said first face 301 of said second web 300 which includes said first adhesive 250;
- d. applying at least one second elastic thread 502 on at least the portion of said first face 701 of said third web 700 or to at least the portion of said first face 301 of said second web 300 which includes said second adhesive 260;
- e. applying a portion of the first face 301 of said second web 300 on the first face 201 of said first web 200, and fixing said first 200 and second webs 300 together such that said at least one first elastic thread 500 is partly sandwiched between the first faces 201, 301 of respective first and second webs 200, 300; such that the first pattern P1 extends over the first edge 203 of the first web 200 to form first loops 501 in said first elastic thread 500 which project in the cross-direction CD from said first edge 203 of said first web 200;
- f. applying a portion of the first face 301 of said second web 300 on the first face 701 of said third web 700, and fixing said third 700 and second webs 300 together such that said at least one second elastic thread 502 is partly sandwiched between the first faces 301, 701 of respective second and third webs 300, 700; such that the second pattern (P2) extends over the first edge 703 of the third web 700 to form second loops 503 in said second elastic thread 502 which project in the cross-direction (CD) from said first edge 703 of said third web 700; and such that said first and second patterns (P1, P2) are synchronised such that the point in the machine direction (MD) at which the first elastic threads (500) are located furthest from the first edge 203 of the first web (200) corresponds substantially to the point in the machine direction (MD) at which the second elastic threads 502 are located furthest from the first edge 703 of the third web 700;
- g. securing the first loops 501 of said first elastic threads 500 in a first loop retaining means 410 located adjacent the first edge 203 of said first web 200;
- h. securing the second loops 503 of said second elastic threads 502 in a second loop retaining means 411 located adjacent the first edge 703 of said third web 700;

may occur substantially simultaneously in a single nip 400.

After cutting the loops 501, 503, an elasticated web 140 having discontinuous elastic threads 510, 511 is provided. This elasticated web 140 may be rolled up and stored, or used directly to produce pant-type articles 20, or absorbent articles 10 of the open-diaper type. In that first and second loop retaining means 410, 411 (e.g. in the form of resilient belts 401, 402, 403, 404) are used to retain the elastic threads 500, 502 in the production of the elasticated web 140, waste pieces of elastic can be captured and controlled safely during the process. In addition, the tension in the discontinuous elastic threads 510, 511 can be controlled, and cutting of the elastic threads 500, 502 can be performed accurately.

Figures 7A, 7B:
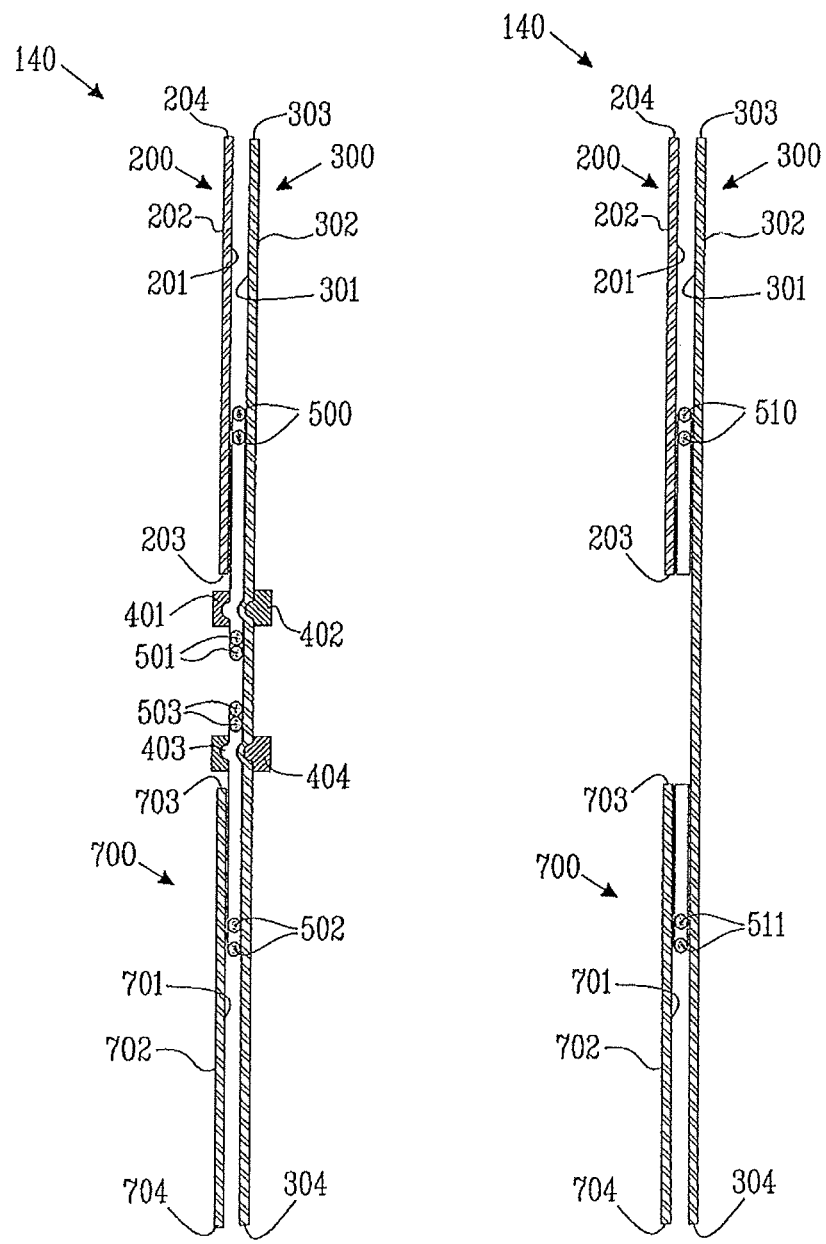
FIG. 7A is an expanded cross-sectional view along the line VIIA-VIIA in FIG. 7
FIG. 7B is an expanded cross-sectional view along the line VIIB-VIIB in FIG. 7

FIG. 7A is an expanded cross-sectional view of the nascent elasticated web 140 along the line VIIA-VIIA in FIG. 7, i.e. prior to cutting the continuous elastic threads 500, 502. It shows the first web 200, the second web 300 and the third web 700. Elastic threads 500 (which project in the cross-direction (CD) from the first edge 203 of said first web 200) are secured between first 401 and second 402 resilient belts. Elastic threads 502 (which project in the cross-direction (CD) from the first edge 703 of the third web 700) are secured between third 403 and fourth 404 resilient belts. In that the second web 300 extends between the first web 200 and the third web 700, it too is secured between the resilient belts 401, 402, 403, 404. In addition, FIG. 7A shows the resilient belts 401, 402, 403, 404 having a particular profile which promotes a secure grip on the elastic threads.

FIG. 7B is an expanded cross-sectional view of the elasticated web 140 along the line VIIB-VIIB in FIG. 7; i.e. after cutting the elastic threads 500, 502. It shows the first web 200, the second web 300 and the discontinuous elastic threads 510 laminated between first 200 and second 300 webs. In a similar way, discontinuous elastic threads 511 are laminated between third 700 and second 300 webs. FIG. 7B shows pairs of elastic threads 510, 511; however, it is also conceivable that a lesser or greater number of elastic threads 510, 511 are included. In particular, it is useful to have more elastic threads in the portion of the elasticated web 140 which is to become the rear portion of a pant-type article 20, or an absorbent article 10.

The disclosure also provides an elasticated web 140 produced according to the methods described herein, as well as the elasticated web 140 per se. The elasticated web 140 is illustrated in FIG. 7, and in cross-section in FIG. 7B. The elasticated web 140 has discontinuous elastic threads 510, 511, and includes:
- a first web 200, said first web 200 having a primary extension in the machine direction (MD), first 201 and second 202 faces and a first edge 203 and a second edge 204, said first and second edges 203, 204 extending in the machine direction (MD);
- a second web 300, said second web 300 having a primary extension in the machine direction (MD), first 301 and second 302 faces and a first edge 303 and a second edge 304, said first and second edges 303, 304 extending in the machine direction (MD); and
- third web 700, said third web 700 having a primary extension in the machine direction (MD), first 701 and second 702 faces and a first edge 703 and a second edge 704, said first and second edges 703, 704 extending in the machine direction (MD).

A first adhesive 250 is arranged on at least a portion of the first face 201 of said first web 200 or on at least the portion of the first face 301 of said second web 300. At least one discontinuous elastic thread 510 is arranged on at least the portion of said first face 201 of said first web 200 or on at least the portion of the first face 301 of said second web 300 which includes said first adhesive 250.

A second adhesive 260 is arranged on at least a portion of the first face 701 of said third web 700 or on at least a portion of the first face 301 of said second web 300. At least one discontinuous elastic thread 511 is arranged on at least the portion of said first face 701 of said third web 700 or on at least the portion of the first face 301 of said second web 300 which includes said second adhesive 260.

The third web 700 lies adjacent and substantially parallel with said first web 200, in a spaced arrangement with the first faces 201, 701 of said webs 200, 700 facing the same direction, such that the first edges 203, 703 of respective first 200 and third 700 webs are adjacent.

The first face 301 of said second web 300 overlies the first face 201 of said first web 200; said first 200 and second webs 300 being fixed together such that said at least one discontinuous elastic thread 510 is sandwiched between the first faces 201, 301 of said respective first and second webs 200, 300.

The first face 301 of said second web 300 also overlies the first face 701 of said third web 700; said third 700 and second webs 300 being fixed together such that said at least one discontinuous elastic thread 511 is sandwiched between the first faces 701, 301 of said respective third and second webs 700, 300.

The at least one discontinuous elastic thread 510 is present in a first pattern (R1). Pattern (R1) corresponds to the portion of pattern (P1), described above, which is located on the first web 200. The first pattern (R1) therefore forms loops 520 which extend from the first edge 203 of the first web 200 and back to said first edge 203 of the first web 200; so that the discontinuous elastic threads 510 terminate at each point at which they meet the first edge 203 of said first web 200.

Similarly, the at least one discontinuous thread 511 is present in a second pattern (R2), Pattern (R2) corresponds to the portion of pattern (P2), described above, which is located on the third web 700. The second pattern (R2) thus forms loops 521 which extend from the first edge 703 of the third web 700 and back to said first edge 703 of the third web 700; so that the discontinuous elastic threads 511 terminate at each point at which they meet the first edge 703 of said third web 700.

As shown in FIG. 7, first and second patterns (R1, R2) are synchronised such that the point in the machine direction (MD) at which the first discontinuous threads 510 are located furthest from the first edge 203 of the first web 200 corresponds substantially to the point in the machine direction (MD) at which the second discontinuous threads 511 are located furthest from the first edge 703 of the third web 700. In other words, the first and second patterns R1, R2 have the same repeat frequency and diverge at essentially the same place in the machine direction.

The method according to the second embodiment (FIG. 7) allows the elasticated web 140 to be formed. In particular, in that the elastic threads 500, 502 are secured between first and second loop retaining means 410, 411 (in particular, between resilient belts 401, 402, 403, 404 as shown in FIG. 7) elastic threads 500, 502 are in tension, which allows accurate cutting of the elastic threads 500, 502 to be carried out, which is not possible with the methods of the prior art. Accordingly, discontinuous elastic threads 510, 511 can terminate at each point at which they meet the first edge 203 of said first web 200, or the first edge 703 of said third web 700, respectively.

The disclosure also provides a method for manufacturing a pant-type article 20 from the elasticated web 140 of the second embodiment. The method for manufacturing pant-type articles 20 according to this second embodiment is illustrated in FIG. 9.

Firstly, an elasticated web 140 is provided, according to the method of FIG. 7. The elasticated web 140 has discontinuous elastic threads 510, 511 in which at least one first discontinuous elastic thread 510 is sandwiched between the first faces 201, 301 of respective first and second webs 200, 300; and at least one second discontinuous elastic thread 511 is sandwiched between the first faces 701, 301 of respective third and second webs 700, 300. The first and second discontinuous elastic threads 510, 511 are synchronised, as described above.

A leg region 122 of the elasticated web 140, defined substantially between discontinuous elastic threads 510, 511 of the first and third webs 200, 700, is cut out, so as to form leg openings 121. Cutting the elasticated web 140 to form leg openings 121 may take place before or after the step of folding the web 140, described below. Cutting the elasticated web 140 takes place in the same manner as described above for the first embodiment.

Figure 9:
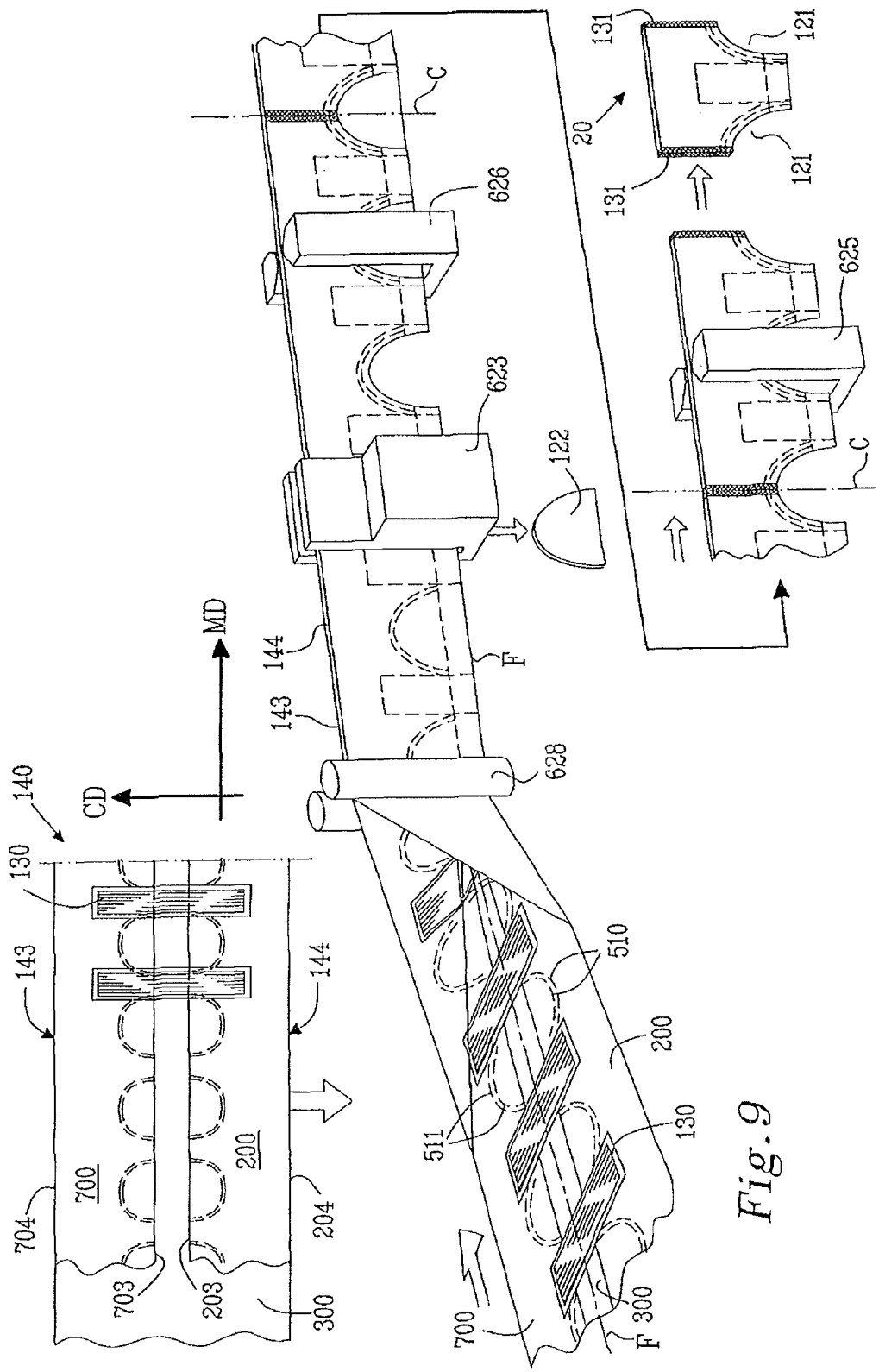
FIG. 9 shows how a pant-type article may be produced from the elasticated web of FIG. 7.

As shown in FIG. 9, the elasticated web 140 is folded along a fold-line (F), so that first and second edges 143, 144 of the elasticated web 140 become arranged substantially adjacent one another and substantially parallel. Suitably, the elasticated web 140 is folded such that the second web 300 is located on the outside of the fold, as shown in FIG. 9. However, the opposite situation is possible, as will become evident in the discussion of FIGS. 15 and 17, below.

The folded elasticated web 140 is then joined along lines (C). Lines (C) extend substantially in the cross direction (CD) from the first and second edges 143, 144 of the elasticated web 140 to the fold-line (F). The lines (C) are located substantially at the point at which the discontinuous elastic threads 510, 511 are located furthest from the fold-line (F). Joining the folded elasticated web 140 in this manner will eventually form side-seams 131 in the finished pant-type article 20. Details of the joining to form side-seams 131 are provided in relation to the first embodiment.

The elasticated web 140 is then cut along lines (C) such that the elasticated web (140) remains joined on either side of the cut. Individual pant-type articles (20) are thereby provided.

If the pant-type article 20 is to include an absorbent packet 130, an absorbent packet 130 is placed so as to overlie at least a portion of the first web 200, second web 300 and/or the third web 700. The absorbent packet 130 is then fixed to at least one of said first, second and/or third webs 200, 300, 700. The absorbent packets 130 are particularly placed on the elasticated web 140 on the face thereof which includes the first 200 and third 700 webs. This will provide pant-type articles 20 according to FIG. 16. Alternatively, the absorbent packets 130 are placed on the elasticated web 140 on the face thereof which includes the second web 300. This will provide pant-type articles 20 according to FIG. 17. Details of the absorbent packet 130 are to be found in relation to the first embodiment, above. Absorbent packets 130 are applied to the elasticated web 140 at any point before the web is folded.

Additional material layers may be added to the pant-type article 20 at any point during the above-described manufacturing process. For example, a topsheet including a nonwoven or nonwoven laminate may be added to the pant-type article 20 on the side which is intended to face the wearer's skin. A liquid-impermeable backsheet may be added to the pant-type article 20 on the side which is intended to face the wearer's garments.

The pant-type articles 20 may include additional components such as waist elastics 135, body elastics 137 and standing gathers. Suitable methods for applying such components will be known to the skilled person.

Figure 10:
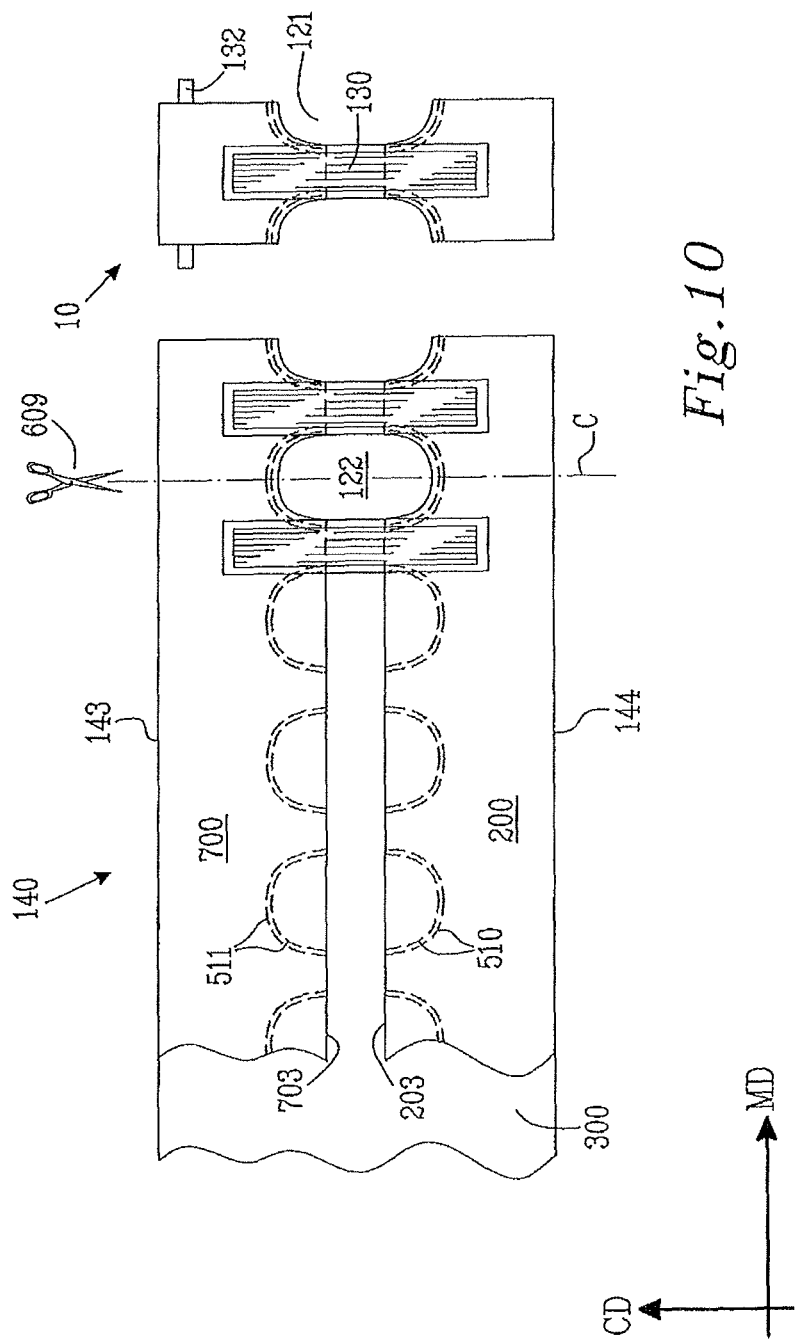
FIG. 10 shows how an open diaper may be produced from the elasticated web of FIG. 7.

The disclosure also provides a method for manufacturing absorbent articles 10 in the form of open diapers from the elasticated web 140 of the second embodiment. This method is illustrated in FIG. 10, and includes the steps of a. providing an elasticated web 140 having discontinuous elastic threads 510, 511 in which at least one first discontinuous elastic thread 510 is sandwiched between the first faces 201, 301 of respective first and second webs 200, 300; and at least one second discontinuous elastic thread 511 is sandwiched between the first faces 701, 301 of respective third and second webs 700, 300;

b. placing an absorbent packet 130 so as to overlie at least a portion of the first web 200, second web 300 and/or the third web 700, and fixing said absorbent packet 130 to at least one of said first, second and/or third webs 200, 300, 700;

c. cutting out a leg region 122 of the elasticated web 140 defined substantially between discontinuous elastic threads 510, 511 of the first and third webs 200, 700, so as to form leg openings 121;

d. providing fastening means 132 on said elasticated web 140; and e. cutting the elasticated web 140 along lines (C), said lines (C) extending substantially in the cross direction (CD) from the first edge 143 to the second edge 144 of the elasticated web 140, said lines (C) being located substantially at the point at which the discontinuous elastic threads 510, 511 are located furthest from the first edges 203, 703 of the first 200 and third 700 webs.

Details of individual steps of this method are the same as those described in relation to FIG. 9, above.

The absorbent articles 10 may include additional components such as waist elastics 135, body elastics 137 and standing gathers. Suitable methods for applying such components will be known to the skilled person.

It is possible that the steps of placing the absorbent packets 130, cutting out leg openings 121 and cutting the elasticated web 140 along lines (C) can take place in any order. However, it can be preferable that the step of cutting the elasticated web 140 along lines (C) takes place last in this series, so that the integrity of the elasticated web 140 is maintained while absorbent packets 130 are fixed to it, and leg openings 121 are cut out.

The disclosure also provides an apparatus 600 for manufacturing an elasticated web 100 having discontinuous elastic threads 510, 511 according to the embodiment illustrated in FIG. 7. The apparatus 600 is illustrated in FIG. 8, and includes:

a. first web supply means 601, for supplying said first web 200;

b. second web supply means 602, for supplying said second web 300;

c. third web supply means 607, for supplying said third web 700;

d. first elastic thread supply means 610 for supplying said at least one first elastic thread 500;

e. second elastic thread supply means 611 for supplying said at least one second elastic thread 502;

f. first adhesive supply means 612 for supplying said first adhesive 250;

g. second adhesive supply means 613 for supplying said second adhesive 260;

h. and cutting means 605, 605' for cutting said first and second elastic threads 500, 502.

The first and second web supply means 601, 602 are as described above for the apparatus of the first embodiment. The third web supply means 607 may also be as described above for the first and second web supply means 601, 602. The first and third web supply means 601, 607 are generally arranged such that first 200 and third 700 webs run in parallel, as shown in FIG. 8.

The first adhesive supply means 612 is arranged so as to apply a first adhesive 250 to at least a portion of the first face 201 of said first web 200 or to at least a portion of the first face 301 of the second web 300. The first elastic thread supply means 610 is arranged so as to apply at least one first elastic thread 500 on at least the portion of said first face 201 of said first web 200 or on at least the portion of said first face 301 of said second web 300 which includes said first adhesive 250. The at least one first elastic thread 500 is applied in a pattern (P), said pattern (P) oscillating in the cross-direction (CD) and extending in the machine direction (MD).

The second adhesive supply means 613 is arranged so as to apply a second adhesive 260 to at least a portion of the first face 701 of the third web 700 or to at least a portion of the first face 301 of the second web 300. The second elastic thread supply means 611 is arranged so as to apply at least one second elastic thread 502 on at least the portion of said first face 701 of said third web 700 or on at least the portion of said first face 301 of said second web 300 which includes said second adhesive 260. The at least one second elastic thread 502 is applied in a pattern (P), said pattern (P) oscillating in the cross-direction (CD) and extending in the machine direction (MD).

Details of the first adhesive supply means 612 and the first elastic thread supply means 610 are given in relation to the apparatus of the first embodiment, above. The second adhesive supply means 613 and second elastic thread supply means 611 may constitute the same means as the first adhesive supply means 612 and the first elastic thread supply means 610, respectively.

The second web supply means 602 is arranged so as to apply the first face 301 of the second web 300 on the first face 201 of the first web 200 and on the first face 701 of the third web 700, as shown in FIGS. 7 and 8. First 200 and second webs 300 are fixed together; and said third 700 and said second 300 webs are fixed together; such that said at least one first elastic thread 500 is partly sandwiched between the first faces 201, 301 of respective first and second webs 200, 300; and said at least one second elastic thread 502 is partly sandwiched between the first faces 701, 301 of respective third and second webs 700, 300. Methods and means for fixing the webs 200, 300, 700 together are provided above in relation to the first embodiment. Notably, the first 250 and second 260 adhesives which are present on the first 200 and third 700 webs may be used to fix these webs to the second web 300.

The pattern (P1) is arranged such that it extends over the first edge 203 of the first web 200 to form first loops 501 in said first elastic threads 500 which project in the cross-direction CD from said first edge 203 of said first web 200. Similarly, pattern (P2) is arranged such that it extends over the first edge 703 of the third web 700 to form second loops 503 in said second elastic threads 502 which project in the cross-direction (CD) from said first edge 703 of said third web 700.

As shown in FIG. 7, first and second patterns (P1, P2) are synchronised such that the point in the machine direction (MD) at which the first elastic threads 500 are located furthest from the first edge 203 of the first web 200 corresponds substantially to the point in the machine direction (MD) at which the second elastic threads 502 are located furthest from the first edge 703 of the third web 700.

The cutting means 605, 605' is arranged so as to cut all the elastic threads 500, 502 substantially at the point at which each first elastic thread 500 crosses the first edge 203 of said first web 200 such that the first loops 501 become detached from the first web 200; and at the point at which each second elastic thread 502 crosses the first edge 703 of said third web 700; such that the second loops 503 become detached from the third web 700. Details of the intermittent cutting means 605, 605' are given above in relation to FIG. 7.

The apparatus 600 includes first loop retaining means 410 located adjacent the first edge 203 of said first web 200 and which is adapted so as to secure the first loops 501 in said first loop retaining means 410. In addition, the apparatus 600 includes second loop retaining means 411 located adjacent the first edge 703 of said third web 700 and which is adapted so as to secure the second loops 503 in said second loop retaining means 411. The first and second loop retaining means 410, 411 may be any loop retaining means described above in relation to FIGS. 1-3.

In the embodiment illustrated in FIG. 8, the first loop retaining means 410 includes at least one first 401 and at least one second 402 resilient belt which are located adjacent the first edge 203 of said first web 200; and which are adapted so as to secure the first loops 501 of the first elastic thread 500 in a nip 400 between said at least one first 401 and said at least one second 402 resilient belt. Similarly, the second loop retaining means 411 includes at least one third 403 and at least one fourth 404 resilient belt which are located adjacent the first edge 703 of said third web 700; and which are adapted so as to secure the second loops 503 of the second elastic thread 502 in a nip 400' between said at least one third 403 and said at least one fourth 404 resilient belt. Details of the first 401, second 402, third 403 and fourth 404 resilient belts are the same as given for the first 401 and second 403 resilient belts, in relation to the first embodiment. In particular, a single wide resilient belt may include the third resilient belt 403 and the first resilient belt 401, and a single wide resilient belt includes the fourth resilient belt 404 and the second resilient belt 402.

In the embodiment illustrated in FIG. 8, first web 200, second web 300, third web 700, elastic threads 500, 502 and resilient belts 401, 402, 403, 404 are brought together in a single nip 400, thereby fixing these components together in a convenient and effective manner.

As is also illustrated in FIG. 8, first web supply means 601, second web supply means 602, third web supply means 607, first elastic thread supply means 610, second elastic thread supply means 611 first adhesive supply means 612, second adhesive supply means 613, cutting means 605, 605', at least one first 401, at least one second 402, at least one third 403 and at least one fourth 404 resilient belts are suitably arranged peripherally about a single central cylinder 620. However, other arrangements of these components are possible.

The apparatus 600 described above may include additional components, making it suitable for manufacturing pant-type articles 20. In this case, the apparatus 600 is illustrated schematically in FIG. 9, and additionally includes;

a. elasticated web supply means 621; for supply of said elasticated web 140;
b. optionally, absorbent packet supply means 622, for supply of absorbent packets 130
c. leg region cutting means 623, for cutting out leg regions 122
d. folding means 628 for folding the elasticated web 140
e. joining means 626 for joining the elasticated web 140.
f. elasticated web cutting means 625, for cutting elasticated web 140

The elasticated web supply means 621 is arranged so as to provide an elasticated web 140 having discontinuous elastic threads 510, 511 in which at least one first discontinuous elastic thread 510 is sandwiched between the first faces 201, 301 of respective first and second webs 200, 300; and at least one second discontinuous elastic thread 511 is sandwiched between the first faces 701, 301 of respective third and second webs 700, 300. The elasticated web supply means 621 may feed elasticated web 140 directly from the apparatus illustrated in FIG. 8; alternatively elasticated web 140 may be fed from another supply e.g. a roll. As for the first web supply means 601 described above, the elasticated web supply means 621 typically includes a supply of elasticated web 140 (e.g. a roll) and means adapted for feeding said elasticated web 140 in a machine direction. The elasticated web supply means 621 may include any suitable combination of cylinders, belts, rods or the like. The elasticated web supply means 621 may include means for controlling forces in the edges 143, 144 of the elasticated web 140, which may arise from the elastic threads 510, 511.

Absorbent packet supply means 622 is arranged so as to place an absorbent packet 130 such that it overlies at least a portion of the first web 200, second web 300 and/or the third web 700. The absorbent packet 130 is then fixed to at least one of said first, second and/or third webs 200, 300, 700. The absorbent packets 130 are placed on the elasticated web 140, particularly on the face thereof which includes first 200 and third 700 webs. Details of the absorbent packet 130 are to be found in relation to the first embodiment, above. Absorbent packets 130 are applied to the elasticated web 140 at any point before the web is folded.

The leg region cutting means 623 is arranged so as to cut out a region of the elasticated web 140 defined substantially between discontinuous elastic threads 510, 511 of the first and third webs 200, 700, so as to form leg openings 121. The skilled person will be able to select a suitable size, location and shape for the leg openings 121 in the elasticated web 140. Further details of the leg region cutting means 623 can be found in relation to the first embodiment, above.

Folding means 628 is arranged so as to fold the elasticated web 140 along a fold-line (F). The fold-line (F) runs in the machine direction of the elasticated web 140. First and second edges 143, 144 of the elasticated web 140 become arranged substantially adjacent one another and substantially parallel. The second web 300 is preferably located on the outside of the fold, but may even be located on the inside of the fold. Details of the folding means 628 and the folding process can be found in relation to the above embodiments.

The joining means 626 are arranged so as to join the folded elasticated web 140 along lines C. Lines C extend substantially in the cross direction CD from the first and second edges 143, 144 of the elasticated web 140 to the fold-line F, said lines C being located substantially at the point at which the discontinuous elastic threads 510, 511 are located furthest from the fold-line F. Joining along lines C will form side-seams 131 in the pant-type article. Details of the joining, and the joining means, to form side-seams 131 are provided in relation to the first embodiment.

Elasticated web cutting means 625 is arranged so as to cut the elasticated web 140 along lines (C) such that the elasticated web 140 remains joined on either side of the cut. In this way, individual pant-type articles 20 are separated from the elasticated web 140.

As described above in relation to the first embodiment, the pant-type articles 20 may include additional components such as waist elastics 135, body elastics 137 and standing gathers. Suitable methods and means for applying such components will be known to the skilled person.

The disclosure also provides an apparatus for manufacturing an absorbent article 10 in the form of an open diaper from the elasticated web 140.

In this case, the apparatus 600 additionally includes;
a. elasticated web supply means 621; for supply of said elasticated web 140;
b. absorbent packet supply means 622, for supply of absorbent packets 130
c. leg region cutting means 623, for cutting out leg regions 122
d. elasticated web cutting means 625, for cutting elasticated web 140 and
e. fastening supply means 627 for supply of fastening means 132.

Details of these components are the same as those described in relation to FIG. 9, above.

As before, the elasticated web supply means 621 is arranged so as to provide an elasticated web 140 having discontinuous elastic threads 510, 511 in which at least one first discontinuous elastic thread 510 is sandwiched between the first faces 201, 301 of respective first and second webs 200, 300; and at least one second discontinuous elastic thread 511 is sandwiched between the first faces 701, 301 of respective third and second webs 700, 300.

The absorbent packet supply means 622 are arranged so as to place an absorbent packet 130 so as to overlie at least a portion of the first web 200, second web 300 and/or the third web 700, and to fix said absorbent packet 130 to at least one of said first, second and third webs 200, 300, 700.

The leg region cutting means 623 is arranged so as to cut out a region of the elasticated web 140 defined substantially between discontinuous elastic threads 510, 511 of the first and third webs 200, 700, so as to form leg openings 121. The elasticated web cutting means 625 is arranged so as to cut the elasticated web 140 along lines C, said lines (C) extending substantially in the cross direction (CD) from the first edge 143 to the second edge 144 of the elasticated web 140, said lines (C) being located substantially at the point at which the discontinuous elastic threads 510, 511 are located furthest from the first edges 203, 703 of the first 200 and third 700 webs. The fastening supply means 627 is arranged so as to provide fastening means 132 on said elasticated web 140. The fastening means 132 are suitably located on the outside face of the absorbent article 10. Details of the fastening means 132 are provided above in the description of the first embodiment.

As described above in relation to the first embodiment, the pant-type articles 20 may include additional components such as waist elastics 135, body elastics 137 and standing gathers. Suitable methods and means for applying such components will be known to the skilled person.

The disclosure also provides various pant-type articles 20 which are produced according to the methods described herein. Embodiments of the pant-type articles 20 are illustrated in FIGS. 11-17. FIGS. 11A-17A are expanded cross-sectional views through the perspective view of FIGS. 11-17 taken along the longitudinal centre line (A-A) in each case.

Each of the pant-type articles 20 illustrated in FIGS. 11-17, include a front panel 150 and a rear panel 160. The front panel is that portion of the article 10 which—when the article is in use—is intended to cover at least a portion of the groin and/or lower belly of the wearer. The rear panel is that portion of the article 20 which—when the article is in use—is intended to cover at least a portion of the buttocks and/or lower back of the wearer.

The illustrated pant-type articles 20 also include a crotch panel 181 which extends between the front panel 150 and the rear panel 160 in the longitudinal direction (L) of the pant-type article 20 and is joined to said front and rear panels 150, 160. The crotch panel 181 is that portion of the article 10 which—when the article is in use—lies substantially between the legs of the wearer.

The crotch panel 181 includes a crotch layer 180 and/or an absorbent packet 130. The pant-type articles of FIGS. 11-17 therefore include various combinations of crotch layer 180 and absorbent packet 130. The crotch layer 180 is that layer of the article 10 which is formed from the fourth web 900 described above. The absorbent packet 130 is as described above, and generally includes an absorbent core 133 covered by one or more cover layers 134.

The pant-type article 20 of FIGS. 11 and 11A includes a crotch layer 180, but no absorbent packet. The crotch layer 180 is separate from the front panel 150 and rear panel 160. It extends between the front panel 150 and the rear panel 160 in the longitudinal direction (L) of the pant-type article 20 and is joined to said front and rear panels 150, 160.

In certain embodiments, the pant-type article 20 of FIGS. 12 and 12A includes an absorbent packet 130, but not a crotch layer. If no crotch layer 180 is present (i.e. the crotch panel 181 only includes core packet 130), the core packet 130 must extend between said front panel 150 and said rear panel 160 and be joined thereto. In this case, it is especially suitable that the cover layer 134 of the absorbent core 133 which is to face the wearer's garment exhibits liquid-barrier properties.

The pant-type article 20 of FIGS. 13 and 13A includes an absorbent packet 130 and a crotch layer 180. The crotch layer 180 extends between the front panel 150 and the rear panel 160 in the longitudinal direction (L) of the pant-type article 20 and is joined to the front and rear panels 150, 160. The absorbent packet 130 may extend between the front panel 150 and the rear panel 160 in the longitudinal direction (L) of the pant-type article 20 and be joined to said front and rear panels 150, 160, as illustrated. However, in certain embodiments, the absorbent packet 130 may only be joined to one of said front and rear panels 150, 160, or solely to the crotch layer 180, as desired. The presence of the crotch layer 180 in the pant-type article 20 of FIGS. 13-13A can add mechanical strength, favourable aesthetic properties and desirable liquid-barrier properties to the article.

The front and rear panels 150, 160 of the pant-type articles 20 of FIGS. 11-17 are joined to each other at side seams 131 located at the transverse edges thereof.

As shown in FIGS. 11-17, and most clearly in FIGS. 11A, 12A, 13A, 14A, 15A, 16A and 17A, at least the front panel 150 of each embodied pant-type article 20 includes a first front layer 151, a second front layer 152 and at least two first leg elastics 153 located between said first 151 and second 152 front layers. The first front layer 151 corresponds to the first web 200 used in the methods described above, and may therefore include any material suitable for the first web 200. The second front layer 152 corresponds to the second web 300 used in the methods described above, and may therefore include any material suitable for the second web 300.

The at least two first leg elastics 153 are located symmetrically on either side of a longitudinal centre line (L1) of the pant-type article 20. The first leg elastics 153 are adapted to seal the leg openings 121 against the legs of the wearer. The first leg elastics 153 correspond to the discontinuous elastic threads 510 in the methods described above, and may therefore include any material suitable for such threads. The at least two first leg elastics 153 are located on either side of a longitudinal centre line (L1) of the pant-type article 20.

The first front layer 151 is defined by first 154 and second edges 155 which extend substantially in the transverse direction (T) of the pant-type article 20. These first 154 and second edges 155 of the first front layer 151 correspond to the first 203 and second 204 edges of the first web 200 used in the methods. The first edge 154 is that edge which is located closest to the crotch panel 181 of the pant-type article 20.

The rear panel 160 of the pant-type articles 20 of FIGS. 11-17 also includes a first rear layer 161, a second rear layer 162 and at least two second leg elastics 163 located between said first 161 and second 162 rear layers. The at least two second leg elastics 163 are located on either side of longitudinal centre line (L1) of the pant-type article 20.

FIGS. 11-17 show pant-type articles 20 having pairs of elastic threads 153, 163; however, it is also conceivable that a lesser or greater number of elastic threads 153, 163 are included. In particular, it is useful to have more elastic threads 163 in the rear panel 160.

The first rear layer 161 is defined by first 164 and second edges 165 which extend substantially in the transverse direction (T) of the pant-type article 20. The first edge 164 is that which is located closest to the crotch panel 181 of the pant-type article 20.

Common to all pant-type articles 20 of FIGS. 11-17 is that the first leg elastics 153 in the front panel 150 terminate at the point at which they meet the first edge 154 of said first front layer 151, and that the second leg elastics 163 in said rear panel 160 terminate at the point at which they meet the first edge 164 of said first rear layer 161. Typically, the leg elastics 153, 163 extend from the first edge 154, 164 of the first front or rear layer 151, 161 towards the side seams 131 of the article 20. The leg elastics 153, 163 are typically curved.

Suitably, the leg elastics 153, 163 do not overlap the absorbent packet 130 at all. It can therefore be preferred that the at least two first leg elastics 153 and said at least two second leg elastics 163 are located on either side of the absorbent packet 130 of the pant-type article 20 in the transverse direction (T).

The pant-type articles of FIGS. 14-17 are similar to those of FIGS. 11-13, except that they are made via the second method, in which first and third webs 200, 700 are laminated to a second web 300. In these cases, therefore, a single second layer 170 includes the second front layer 152, the second rear layer 162 and the crotch layer 180. FIGS. 14 and 14A show a pant-type article 20 with a single second layer 170 which does not include an absorbent packet 130, and in which the single second layer 170 lies towards the outside of the product. FIGS. 15 and 15A show a pant-type article 20 with a single second layer 170 which does not include an absorbent packet 130, and in which the single second layer 170 lies towards the inside of the product. Whether articles of FIG. 14 or FIG. 15 are made depends on which way the elasticated web 140 is folded during manufacture.

FIGS. 16 and 16A show a pant-type article 20 with a single second layer 170, and which includes an absorbent packet 130, in which the single second layer 170 lies towards the outside of the product. FIGS. 17 and 17A show a pant-type article 20 with a single second layer 170, and which includes an absorbent packet 130, in which the single second layer 170 lies towards the inside of the product. Whether articles of FIG. 16 or FIG. 17 are made depends on which way the absorbent packet 130 is applied to the elasticated web 140 during manufacture.

The pant-type articles 20 of the invention may include additional components such as waist elastics 135, body elastics 137 and standing gathers.

FIGS. 18-21 show absorbent articles 10 in the form of open diapers. FIGS. 18A-21A are cross-sectional views along the longitudinal centre lines (A-A) in FIGS. 18-21, respectively.

The absorbent articles 10 illustrated in FIGS. 18, 19 and 18A, 19A are formed by the methods described in relation to FIG. 6, and extend in the longitudinal (L) and transverse (T) directions, as shown.

Each of the absorbent articles 10 illustrated in FIGS. 18-19, includes a front panel 150 and a rear panel 160 and an absorbent packet 130. Each article also includes a crotch panel 181. The crotch panel 181 extends between the front panel 150 and the rear panel 160 in the longitudinal direction (L) of the absorbent article 10 and is joined to the front and rear panels 150, 160. The crotch panel 181 includes an absorbent packet 130 and optionally, a crotch layer 180.

The absorbent article 10 of FIGS. 18 and 18A includes both a crotch layer 180 and a core packet 130. The presence of the crotch layer 180 in the absorbent article 10 of FIGS. 18 and 18A can add mechanical strength, favourable aesthetic properties and desirable liquid-barrier properties to the article.

In certain embodiments, at least the crotch layer 180 extends between said front panel 150 and said rear panel 160 in the longitudinal direction (L) of the absorbent article 10 and is joined to said front and rear panels 150, 160. The absorbent packet 130 may only be joined to one of said front and rear panels 150, 160, or solely to the crotch layer 180, as desired. However, if no crotch layer 180 is present, the core packet must extend between said front panel 150 and said rear panel 160 and be joined thereto.

The absorbent article 10 of FIGS. 19 and 19A does not include a crotch layer 180, but instead, the front and rear panels 150, 160 are bridged solely via the core packet 130. In this case, it is suitable that the cover layer 134 of the absorbent core 133 which is to face the wearer's garment exhibits liquid-barrier properties.

At least one of said front and rear panels 150, 160 include fastening means 132. Suitable fastening means 132, and means and methods for their application are discussed above.

At least the front panel 150 includes a first front layer 151, a second front layer 152 and at least two first leg elastics 153 located between said first 151 and second 152 front layers. The at least two first leg elastics 153 are located on either side of a longitudinal centre line L1 of the absorbent article 10.

The first front layer 151 is defined by first 154 and second edges 155 which extend substantially in the transverse direction T of the absorbent article 10. The first 154 edge is that which is located closest to the crotch panel 181 of the absorbent article 10.

The rear panel 160 also includes a first rear layer 161, a second rear layer 162 and at least two second leg elastics 163 located between said first 161 and second 162 rear layers. The at least two second leg elastics 163 are located on either side of longitudinal centre line L1 of the absorbent article 10.

FIGS. 18-21 show absorbent articles 10 having pairs of elastic threads 153, 163; however, it is also conceivable that a lesser or greater number of elastic threads 153, 163 are included. In particular, it is useful to have more elastic threads 163 in the rear panel 160.

The first rear layer 161 is defined by first 164 and second edges 165 which extend substantially in the transverse direction T of the absorbent article 10. The first 164 edge is that which is located closest to the crotch panel 181 of the absorbent article 10.

Suitable materials for the layers 151, 152, 161, 162, absorbent packet 130 and the elastics 153, 163 are provided above for the pant-type articles 20 of the invention.

As shown in FIGS. 18-21, the first leg elastics 153 in the front panel 150 terminate at the point at which they meet the first edge 154 of said first front layer 151 while the second leg elastics 163 in the rear panel 160 terminate at the point at which they meet the first edge 164 of the first rear layer 161.

Suitably, the leg elastics 153, 163 do not overlap the absorbent packet 130 at all. It can therefore be preferred that the at least two first leg elastics 153 and said at least two second leg elastics 163 are located on either side of the absorbent packet 130 of the absorbent article 10 in the transverse direction (T).

The absorbent article 10 of FIGS. 20, 21, 20A and 21A is similar to those of FIGS. 18-19, except that it is made via the second method of the invention, in which first and third webs 200, 700 are laminated to a second web 300. In these cases, therefore, a single second layer 170 includes the second front layer 152, the second rear layer 162 and the crotch layer 180.

FIG. 20 shows an absorbent article 10 in which the absorbent packet 130 is located on the first 200 and third 700 webs during manufacture. The second web 300 (=single second layer 170) therefore lies on the face of the absorbent article 10 opposite to the absorbent packet 130. This arrangement provides the absorbent article 10 with a continuous outer face, comprised of the single second layer 170/second web 300.

Figure 21A:
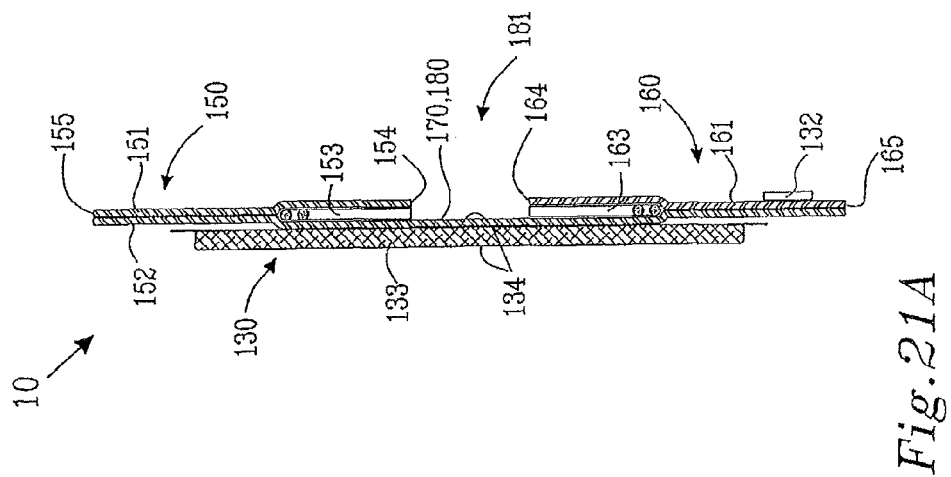
FIG. 21A is a cross-sectional view along line XXIA-XXIA of FIG. 21
Figure 21:
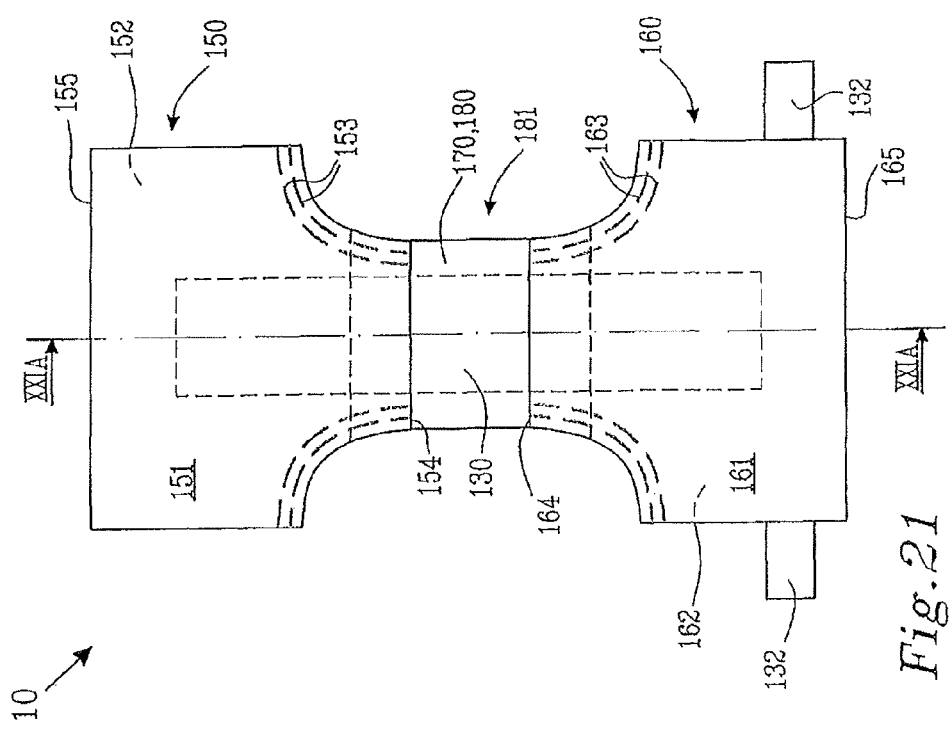
FIG. 21 shows an embodiment of an open diaper

FIG. 21 shows an absorbent article 10 in which the absorbent packet 130 is located on the second web 300 during manufacture. The second web 300 (=single second layer 170) therefore lies on the same face of the absorbent article 10 as the absorbent packet 130.

FIG. 20A is an expanded cross-sectional view along the line XXA-XXA in FIG. 20; i.e. through the absorbent article 10 along its length. FIG. 21A is an expanded cross-sectional view along the line XXIA-XXIA in FIG. 21; i.e. through the absorbent article 10 along its length.

The absorbent articles 10 of the invention may include additional components such as waist elastics 135, body elastics 137 and standing gathers.

The invention has been described with reference to a number of embodiments. However, the scope of the invention should not be considered as limited to the illustrated and described embodiments. Instead, features from certain embodiments may be combined at will with features from other embodiments, while remaining within the scope of the claims. The scope of the invention should be determined by the appended claims.

The invention claimed is:

1. A method for manufacturing pant-type articles, said method comprising the steps of:
   a. providing a first web, said first web having a primary extension in the machine direction, first and second faces and a first edge and a second edge, said first and second edges extending in the machine direction;
   b. providing a second web, said second web also having a primary extension in the machine direction, first and second faces and a first edge and a second edge, said first and second edges extending in the machine direction;
   c. applying a first adhesive to at least a portion of the first face of said first web;
   d. applying at least one elastic thread on at least the portion of said first face of said first web which comprises said first adhesive: wherein said at least one thread is applied in a pattern, said pattern oscillating in the cross-direction and extending in the machine direction, such that the pattern extends over the first edge of the first web to form loops in said elastic thread which project in the cross-direction from said first edge of said first web;
   e. securing the loops in a loop retaining element comprising at least one first and at least one second resilient belt which are located adjacent the first edge of said first web;
   f. applying the first face of said second web on the first face of said first web, and fixing said first and second webs together such that said at least one elastic thread is partly sandwiched between the first faces of said respective first and second webs;
   g. cutting the elastic thread substantially at each point at which the elastic thread crosses the first edge of said first web such that the loops become detached from the first web so as to thereby provide an elasticated web having discontinuous elastic threads, said elasticated web having first and second edges extending in the machine direction and said discontinuous elastic threads being sandwiched between the first faces of the respective first and second webs and extending to the first edge of said elasticated web;
   h. arranging first and second such elasticated webs adjacent one another and in a spaced relationship such that the first edges of each of said elasticated webs are located closest to one another and aligned substantially parallel to one another; said first and second elasticated webs being synchronised such that each discontinuous elastic thread in the first elasticated web is located opposite the corresponding discontinuous elastic thread in the second elasticated web;
   i. placing at least one of a fourth web or an absorbent packet so as to overlie at least a portion of at least one of the first or second elasticated webs, and fixing at least one of said fourth web or said absorbent packet to both first and second elasticated webs;
   j. cutting out leg regions of one or both elasticated webs and, if present, said fourth web; each leg region being defined substantially within said elasticated webs by the discontinuous elastic threads;
   k. folding the co-joined elasticated webs along a fold-line, so that the second edges of each elasticated web become arranged substantially adjacent one another and substantially parallel, with at least one of the fourth web located on the outside of the fold or the absorbent packet located on the inside of the fold;
   l. joining the first and second elasticated webs to each other along cutting lines, said cutting lines extending substantially in the cross-direction from the second edges of each elasticated web to the fold-line, said cutting lines being located substantially at the point at which the at least one discontinuous elastic thread is located furthest from the first edge of each elasticated web; to form side-seams; and
   m. cutting each elasticated web, and, if present, the fourth web, along the cutting lines such that first and second elasticated webs remain joined on either side of the cut, so as to provide pant-type articles.

2. The method according to claim 1, wherein steps d., e. and f. of the method occur substantially simultaneously in a single nip.

3. The method according to claim 1, wherein the second web is applied to the first web such that the first edge of the second web is substantially aligned with the first edge of the first web.

4. A method for manufacturing absorbent articles, said method comprising the steps of:
   a. providing a first web, said first web having a primary extension in the machine direction, first and second faces and a first edge and a second edge, said first and second edges extending in the machine direction;

b. providing a second web, said second web also having a primary extension in the machine direction, first and second faces and a first edge and a second edge, said first and second edges extending in the machine direction;

c. applying a first adhesive to at least a portion of the first face of said first web;

d. applying at least one elastic thread on at least the portion of said first face of said first web which comprises said first adhesive; wherein said at least one thread is applied in a pattern, said pattern oscillating in the cross-direction and extending in the machine direction, such that the pattern extends over the first edge of the first web to form loops in said elastic thread which project in the cross-direction from said first edge of said first web;

e. securing the loops in a loop retaining element comprising at least one first and at least one second resilient belt which are located adjacent the first edge of said first web;

f. applying the first face of said second web on the first face of said first web, and fixing said first and second webs together such that said at least one elastic thread is partly sandwiched between the first faces of said respective first and second webs;

g. cutting the elastic thread substantially at each point at which the elastic thread crosses the first edge of said first web such that the loops become detached from the first web so as to thereby provide an elasticated web having discontinuous elastic threads, said elasticated web having first and second edges extending in the machine direction and said discontinuous elastic threads being sandwiched between the first faces of the respective first and second webs and extending to the first edge of said elasticated web;

h. arranging first and second such elasticated webs adjacent one another and in a spaced relationship such that the first edges of each of said elasticated webs are located closest to one another and aligned substantially parallel to one another; said first and second elasticated webs being synchronised such that each discontinuous elastic thread in the first elasticated web is located opposite the corresponding discontinuous elastic thread in the second elasticated web;

i. placing an absorbent packet so as to overlie at least a portion of at least one of the first or second elasticated webs;

j. optionally, placing a fourth web so as to overlie the first edges of the first and second elasticated webs, and fixing at least one of said fourth web or said absorbent packet to both first and second elasticated webs;

k. cutting out leg regions of said fourth web and optionally at least one of said first or second elasticated webs; each leg region being defined substantially within said elasticated webs by the discontinuous elastic threads;

l. cutting the co-joined elasticated webs and, if present, the fourth web along cutting lines, said cutting lines extending substantially in the cross-direction from the second edge of one elasticated web to the second edge of the other elasticated web, said cutting lines being located substantially at the point at which the at least one discontinuous elastic thread is located furthest from the first edge of each elasticated web; and m. providing fastening means on at least one of said first and second elasticated webs; so as to provide absorbent articles.

5. The method according to claim 4, wherein steps d., e. and f. of the method occur substantially simultaneously in a single nip.

6. The method according to claim 4, wherein the second web is applied to the first web such that the first edge of the second web is substantially aligned with the first edge of the first web.

7. A method for manufacturing an elasticated web having discontinuous elastic threads, said method comprising the steps of:

a. providing a first web, said first web having a primary extension in the machine direction, first and second faces and a first edge and a second edge, said first and second edges extending in the machine direction;

b. providing a second web, said second web also having a primary extension in the machine direction, first and second faces and a first edge and a second edge, said first and second edges extending in the machine direction;

c. providing a third web said third web having a primary extension in the machine direction, first and second faces and a first edge and a second edge, said first and second edges extending in the machine direction;

d. arranging said third web to lie adjacent and substantially parallel with said first web, in a spaced arrangement with the first faces of said first and third webs facing the same direction, such that the first edges of the respective first and third webs are adjacent;

e. applying a first adhesive to at least a portion of the first face of said first web or to at least a portion of the first face of the second web;

f. applying a second adhesive to at least a portion of the first face of said third web or to at least a portion of the first face of the second web;

g. applying at least one first elastic thread on at least the portion of said first face of said first web or on at least the portion of said first face of said second web which comprises said first adhesive; wherein said at least one first thread is applied in a first pattern, said first pattern oscillating in the cross-direction and extending in the machine direction, h. applying at least one second elastic thread on at least the portion of said first face of said third web or to at least the portion of said first face of said second web which comprises said second adhesive; wherein said at least one second elastic thread is applied in a second pattern, said second pattern oscillating in the cross-direction and extending in the machine direction, i. applying a portion of the first face of said second web on the first face of said first web, and fixing said first and second webs together such that said at least one first elastic thread is partly sandwiched between the first faces of the respective first and second webs; such that the first pattern extends over the first edge of the first web to form first loops in said first elastic thread which project in the cross-direction from said first edge of said first web;

j. applying a portion of the first face of said second web on the first face of said third web, and fixing said third and second webs together such that said at least one second elastic thread is partly sandwiched between the first faces of the respective second and third webs; such that the second pattern extends over the first edge of the third web to form second loops in said second elastic thread which project in the cross-direction from said first edge of said third web; and such that said first and second patterns are synchronised such that the point in the machine direction at which the first elastic threads are located furthest from the first edge of the first web corresponds substantially to the point in the machine direction at which the second elastic threads are located furthest from the first edge of the third web;

k. securing the first loops of said first elastic threads in a first loop retaining element comprising at least one first resilient belt or belt portion and at least one second resilient belt or belt portion which are located adjacent the first edge of said first web;

l. securing the second loops of said second elastic threads in a second loop retaining element comprising at least one third resilient belt or belt portion and at least one fourth resilient belt or belt portion which are located adjacent the first edge of said third web;

m. cutting all the first elastic threads substantially at the point at which each first elastic thread crosses the first edge of said first web such that the first loops become detached from the first web; and n. cutting all the second elastic threads substantially at the point at which each second elastic thread crosses the first edge of said third web such that the second loops become detached from the third web;

wherein step d. can take place at any point in the process before step i. so as to provide the elasticated web having discontinuous elastic threads.

8. The method according to claim 7, wherein steps e.-l. of the method occur substantially simultaneously in a single nip.

9. The method according to claim 7, wherein a single wide resilient belt comprises the third resilient belt portion and the first resilient belt portion, and a single wide resilient belt comprises the fourth resilient belt portion and the second resilient belt portion.

10. A method for manufacturing pant-type articles, said method comprising the steps of:

a. carrying out the method according to claim 7 to provide the elasticated web having discontinuous elastic threads in which at least one first discontinuous elastic thread is sandwiched between the first faces of the respective first and second webs; and at least one second discontinuous elastic thread is sandwiched between the first faces of the respective third and second webs;

b. cutting out a leg region of the elasticated web defined substantially between discontinuous elastic threads of the first and third webs so as to form leg openings;

c. folding the elasticated web along a fold-line, so that first and second edges of the elasticated web become arranged substantially adjacent one another and substantially parallel, d. joining the folded elasticated web along cutting lines, said cutting lines extending substantially in the cross-direction from the first and second edges of the elasticated web to the fold-line, said cutting lines being located substantially at the point at which the discontinuous elastic threads are located furthest from the fold-line; to form side-seams; and e. cutting the elasticated web along cutting lines such that the elasticated web remains joined on either side of the cut;

wherein steps b. and c. can take place in any order, so as to thereby provide the pant-type articles.

11. The method according to claim 10, said method comprising the additional step of placing an absorbent packet so as to overlie at least a portion of at least one of the first web, the second web or the third web, and fixing said absorbent packet to at least one of said first, second or third webs; after step a., but before step c.

12. A method for manufacturing absorbent articles, said method comprising the steps of:

a. carrying out the method according to claim 7 to provide the elasticated web having discontinuous elastic threads in which at least one first discontinuous elastic thread is sandwiched between the first faces of the respective first and second webs; and at least one second discontinuous elastic thread is sandwiched between the first faces of the respective third and second webs;

b. placing an absorbent packet so as to overlie at least a portion of at least one of the first web, the second web or the third web, and fixing said absorbent packet to at least one of said first, second and/or third webs;

c. cutting out a region of the elasticated web defined substantially between discontinuous elastic threads of the first and third webs, so as to form leg openings;

d. providing a fastening element on said elasticated web; and e. cutting the elasticated web along cutting lines, said cutting lines extending substantially in the cross-direction from the first edge to the second edge of the elasticated web, said cutting lines being located substantially at the point at which the discontinuous elastic threads are located furthest from the first edges of the first and third webs; so as to provide absorbent articles.

13. An apparatus, comprising:

a first web supply element for supplying said first web;

a second web supply element for supplying said second web;

an elastic thread supply element for supplying said at least one elastic thread;

an adhesive supply element for supplying said first adhesive;

an elastic cutting element for cutting said at least one elastic thread;

an elasticated web supply element for supply of first and second elasticated webs, said first and second elasticated webs having first and second edges extending in the machine direction;

a fourth web supply element for supply of at least one of a fourth web or an absorbent packet supply element for supply of absorbent packets;

a leg region cutting element for cutting out leg regions;

a folding element for folding the co-joined elasticated webs;

a joining element for joining the first and second elasticated webs; and an elasticated web cutting element for cutting elasticated webs and, if present, the fourth web, wherein said adhesive supply element is arranged so as to apply a first adhesive to at least a portion of the first face of said first web;

wherein said elastic thread supply element is arranged so as to apply at least one elastic thread on at least the portion of said first face of said first web which comprises said first adhesive; wherein said at least one thread is applied in a pattern, said pattern oscillating in the cross-direction and extending in the machine direction, such that the pattern extends over the first edge of the first web to form loops in said elastic thread which project in the cross-direction from said first edge of said first web;

wherein said second web supply element is arranged so as to apply the first face of said second web on the first face of said first web, and fix said first and second webs together such that said at least one elastic thread is partly sandwiched between the first faces of the respective first and second webs;

wherein said elastic cutting element is arranged so as to cut all the elastic threads substantially at the point at which each elastic thread crosses the first edge of said first web such that the loops become detached from the first web;

wherein the apparatus additionally comprises a loop retaining element comprising at least one first and at least one second resilient belt located adjacent the first edge of said first web and which are adapted so as to secure the loops in a nip between said at least one first and said at least one second resilient belt in said loop retaining element;

wherein said elasticated web supply element is arranged so as to provide the first and second elasticated webs adjacent one another and in a spaced relationship such that the first edges of each of said elasticated webs are located closest to one another and aligned substantially parallel to one another; said first and second elasticated webs being synchronised such that each discontinuous elastic thread in the first elasticated web is located opposite the corresponding discontinuous elastic thread in the second elasticated web;

wherein said fourth web supply element for supply of the fourth web is arranged so as to place the fourth web so as to overlie the first edges of the first and second elasticated webs, and to fix said fourth web to both first and second elasticated webs;

wherein said absorbent packet supply element is arranged so as to place an absorbent packet so as to overlie at least a portion of the first or second elasticated webs, and to fix said absorbent packet to at least one of said first and second elasticated webs; such that at least one of said fourth web or said absorbent packet is fixed to both first and second elasticated webs;

wherein said leg region cutting element is arranged so as to cut out a leg region of one or both elasticated webs and, if present, said fourth web; each leg region being defined substantially by the discontinuous elastic threads so as to form leg openings;

wherein said folding element is arranged so as to fold the co-joined elasticated webs along a fold-line, so that the second edges of each elasticated web become arranged substantially adjacent one another and substantially parallel, with at least one of the fourth web located on the outside of the fold or the absorbent packet located on the inside of the fold;

wherein said joining element is arranged so as to join the first and second elasticated webs to each other along cutting lines, said cutting lines extending substantially in the cross-direction from the second edges of each elasticated web to the fold-line, said cutting lines being located substantially at the point at which the at least one discontinuous elastic thread is located furthest from the first edge of each elasticated web; to form side-seams; and wherein said elasticated web cutting element is arranged so as to cut each elasticated web and, if present, the fourth web along the cutting lines such that first and second elasticated webs remain joined on either side of the cut.

14. The apparatus according to claim 13, in which said first and second webs are fixed together in a single nip.

15. The apparatus according to claim 13, wherein
the first web supply element;
the second web supply element;
the elastic thread supply element for supplying at least one elastic thread;
the adhesive supply element;
the cutting element; and
the loop retaining element
are arranged peripherally about a single central cylinder.

16. An apparatus, comprising:
a first web supply element for supplying said first web;
a second web supply element for supplying said second web;
an elastic thread supply element for supplying said at least one elastic thread;
an adhesive supply element for supplying said first adhesive;
an elastic cutting element for cutting said at least one elastic thread;
an elasticated web supply element for supply of first and second elasticated webs, said first and second elasticated webs having first and second edges extending in the machine direction;
an absorbent packet supply element for supply of absorbent packets;
optionally, a fourth web supply element for supply of a fourth web;
a leg region cutting element for cutting out leg regions;
an elasticated web cutting element for cutting elasticated webs and, if present, the fourth web; and
a fastening supply element for supply of a fastening element, wherein said adhesive supply element is arranged so as to apply a first adhesive to at least a portion of the first face of said first web;

wherein said elastic thread supply element is arranged so as to apply at least one elastic thread on at least the portion of said first face of said first web which comprises said first adhesive; wherein said at least one thread is applied in a pattern, said pattern oscillating in the cross-direction and extending in the machine direction, such that the pattern extends over the first edge of the first web to form loops in said elastic thread which project in the cross-direction from said first edge of said first web;

wherein said second web supply element is arranged so as to apply the first face of said second web on the first face of said first web, and fix said first and second webs together such that said at least one elastic thread is partly sandwiched between the first faces of the respective first and second webs;

wherein said elastic cutting element is arranged so as to cut all the elastic threads substantially at the point at which each elastic thread crosses the first edge of said first web such that the loops become detached from the first web;

wherein the apparatus additionally comprises a loop retaining element comprising at least one first and at least one second resilient belt located adjacent the first edge of said first web and which are adapted so as to secure the loops in a nip between said at least one first and said at least one second resilient belt in said loop retaining element;

wherein said elasticated web supply element is arranged so as to provide the first and second elasticated webs adjacent one another and in a spaced relationship such that the first edges of each of said elasticated webs are located closest to one another and aligned substantially parallel to one another; said first and second elasticated webs being synchronised such that each discontinuous elastic thread in the first elasticated web is located opposite the corresponding discontinuous elastic thread in the second elasticated web;

wherein said absorbent packet supply element is arranged so as to place the absorbent packet so as to overlie at least a portion of the first or second elasticated webs;

wherein said fourth web supply element is arranged so as to place the fourth web so as to overlie the first edges of the first and second elasticated webs, and fixing at least one of said fourth web or said absorbent packet to both first and second elasticated webs;

wherein said leg region cutting element is arranged so as to cut out the leg region of one or both elasticated webs and, if present, said fourth web; each leg region being defined substantially by the discontinuous elastic threads so as to form leg openings;

wherein said elasticated web cutting element is arranged to cut the co-joined elasticated webs and, if present, the fourth web along cutting lines, said cutting lines extending substantially in the cross-direction from the second edge of one elasticated web to the second edge of the other elasticated web, said cutting lines being located substantially at the point at which the at least one discontinuous elastic thread is located furthest from the first edge of each elasticated web; and wherein said fastening supply element is arranged so as to provide the fastening element on at least one of said first and second elasticated webs.

17. The apparatus according to claim 16, in which said first and second webs are fixed together in a single nip.

18. The apparatus according to claim 16, wherein
the first web supply element;
the second web supply element;
the elastic thread supply element for supplying at least one elastic thread;
the adhesive supply element;
the cutting element; and
the loop retaining element
are arranged peripherally about a single central cylinder.

19. An apparatus, comprising:
a first web supply element for supplying said first web;
a second web supply element for supplying said second web;
a third web supply element for supplying said third web;
a first elastic thread supply element for supplying said at least one first elastic thread;
a second elastic thread supply element for supplying said at least one second elastic thread;
a first adhesive supply element for supplying said first adhesive;
a second adhesive supply element for supplying said second adhesive; and
a cutting element for cutting said first and second elastic threads;
wherein said first adhesive supply element is arranged so as to apply the first adhesive to at least a portion of the first face of said first web or to at least a portion of the first face of the second web;
wherein said first elastic thread supply element is arranged so as to apply the at least one first elastic thread on at least the portion of said first face of said first web or on at least the portion of said first face of said second web which comprises said first adhesive; wherein said at least one first elastic thread is applied in said first pattern oscillating in the cross-direction and extending in the machine direction,
wherein said second adhesive supply element is arranged so as to apply the second adhesive to at least a portion of the first face of the third web or to at least a portion of the first face of the second web;
wherein said second elastic thread supply element is arranged so as to apply the at least one second elastic thread on at least the portion of said first face of said third web or on at least the portion of said first face of said second web which comprises said second adhesive; wherein said at least one second elastic thread is applied in a said second pattern oscillating in the cross-direction and extending in the machine direction,
wherein said second web supply element is arranged so as to apply the first face of said second web on the first face of said first web and the first face of said third web, and fix said first and second webs together; and said third and said second webs together; such that said at least one first elastic thread is partly sandwiched between the first faces of the respective first and second webs; and said at least one second elastic thread is partly sandwiched between the first faces of the respective third and second webs; and such that the first pattern extends over the first edge of the first web to form the first loops in said first elastic threads which project in the cross-direction from said first edge of said first web; and such that the second pattern extends over the first edge of the third web to form the second loops in said second elastic threads which project in the cross-direction from said first edge of said third web; and such that said first and second patterns are synchronised such that the point in the machine direction at which the first elastic threads are located furthest from the first edge of the first web corresponds substantially to the point in the machine direction at which the second elastic threads are located furthest from the first edge of the third web;
wherein said cutting element is arranged so as to cut all the elastic threads substantially at the point at which each first elastic thread crosses the first edge of said first web such that the first loops become detached from the first web; and at the point at which each second elastic thread crosses the first edge of said third web; such that the second loops become detached from the third web; and
wherein the first loop retaining element is adapted so as to secure the first loops of the first elastic thread in a nip between said at least one first resilient belt or belt portion and said at least one second resilient belt or belt portion and the second loop retaining element is adapted so as to secure the second loops of the second elastic thread in a nip between said at least one third resilient belt or belt portion and said at least one fourth resilient belt or belt portion.

20. The apparatus according to claim 19, in which said first, second and third webs are fixed together in a single nip.

21. The apparatus according to claim 19, wherein a single wide resilient belt comprises the third resilient belt portion and the first resilient belt portion, and a single wide resilient belt comprises the fourth resilient belt portion and the second resilient belt portion.

22. The apparatus according to claim 19, wherein
the first web supply element for supplying said first web;
the second web supply element for supplying said second web;
the third web supply element for supplying said third web;
the first elastic thread supply element for supplying said at least one first elastic thread;
the second elastic thread supply element for supplying said at least one second elastic thread;
the first adhesive supply element for supplying said first adhesive;
the second adhesive supply element for supplying said second adhesive;
the cutting element for cutting said first and second elastic threads; and
the first and second loop retaining elements;
are arranged peripherally about a single central cylinder.

23. The apparatus according to claim 19, said apparatus additionally comprising:
- an elasticated web supply element for supply of said elasticated web having first and second edges extending in the machine direction;
- optionally, an absorbent packet supply element for supply of absorbent packets;
- a leg region cutting element for cutting out leg regions;
- a folding element for folding the elasticated web;
- a joining element for joining the elasticated web; and
- an elasticated web cutting element for cutting elasticated web,
- wherein said elasticated web supply element is arranged so as to provide the elasticated web having discontinuous elastic threads in which at least one first discontinuous elastic thread is sandwiched between the first faces of the respective first and second webs; and at least one second discontinuous elastic thread is sandwiched between the first faces of the respective third and second webs;
- wherein said absorbent packet supply element is arranged so as to place the absorbent packet so as to overlie at least a portion of at least one of the first web, the second web or the third web, and to fix said absorbent packet to at least one of said first, second and third webs;
- wherein said leg region cutting element is arranged so as to cut out the leg region of the elasticated web defined substantially between the discontinuous elastic threads of the first and third webs, so as to form leg openings;
- wherein said folding element is arranged so as to fold the elasticated web along a fold-line, so that the first and second edges of the elasticated web become arranged substantially adjacent one another and substantially parallel,
- wherein said joining element is arranged so as to join the folded elasticated web along cutting lines, said cutting lines extending substantially in the cross-direction from the first and second edges of the elasticated web to the fold-line, said cutting lines being located substantially at the point at which the discontinuous elastic threads are located furthest from the fold-line; to form side-seams;
- wherein said elasticated web cutting element is arranged so as to cut the elasticated web along the cutting lines such that the elasticated web remains joined on either side of the cut.

24. The apparatus according to claim 19, said apparatus additionally comprising:
- an elasticated web supply element for supply of said elasticated web having first and second edges extending in the machine direction;
- an absorbent packet supply element for supply of absorbent packets;
- a leg region cutting element for cutting out leg regions;
- an elasticated web cutting element for cutting elasticated web; and
- a fastening supply element for supply of a fastening element
- wherein said elasticated web supply element is arranged so as to provide the elasticated web having discontinuous elastic threads in which at least one first discontinuous elastic thread is sandwiched between the first faces of the respective first and second webs; and at least one second discontinuous elastic thread is sandwiched between the first faces of the respective third and second webs;
- wherein said absorbent packet supply element is arranged so as to place the absorbent packet so as to overlie at least a portion of at least one of the first web, the second web or the third web, and to fix said absorbent packet to at least one of said first, second and third webs;
- wherein said leg region cutting element is arranged so as to cut out the leg region of the elasticated web defined substantially between the discontinuous elastic threads of the first and third webs, so as to form leg openings;
- wherein said fastening supply element is arranged so as to provide the fastening element on said elasticated web;
- wherein said elasticated web cutting element is arranged so as to cut the elasticated web along cutting lines, said cutting lines extending substantially in the cross-direction from the first edge to the second edge of the elasticated web, said cutting lines being located substantially at the point at which the discontinuous elastic threads are located furthest from the first edges of the first and third webs.

* * * * *